(12) United States Patent
Stojanovic et al.

(10) Patent No.: US 10,155,940 B2
(45) Date of Patent: Dec. 18, 2018

(54) APTAMER METHODS AND COMPOSITIONS

(71) Applicant: The Trustees of Columbia University in the City of New York, New York, NY (US)

(72) Inventors: Milan N. Stojanovic, Fort Lee, NJ (US); Tilla S. Worgall, New York, NY (US); Kyungae Yang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/855,171

(22) Filed: Sep. 15, 2015

(65) Prior Publication Data

US 2016/0076021 A1    Mar. 17, 2016

Related U.S. Application Data

(63) Continuation-in-part of application No. PCT/US2014/029281, filed on Mar. 14, 2014.

(60) Provisional application No. 61/798,079, filed on Mar. 15, 2013.

(51) Int. Cl.
| | |
|---|---|
| *C07H 21/04* | (2006.01) |
| *C12N 15/10* | (2006.01) |
| *C12N 15/115* | (2010.01) |
| *C12N 15/11* | (2006.01) |
| *G01N 33/53* | (2006.01) |

(52) U.S. Cl.
CPC ........ *C12N 15/1048* (2013.01); *C12N 15/111* (2013.01); *C12N 15/115* (2013.01); *G01N 33/5308* (2013.01); *C12N 2310/16* (2013.01); *C12N 2320/10* (2013.01); *C12N 2320/13* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 5,543,293 A | 8/1996 | Gold et al. | |
| 5,756,291 A | 5/1998 | Griffin et al. | |
| 5,773,598 A | 6/1998 | Burke et al. | |
| 6,261,774 B1 | 7/2001 | Pagratis et al. | |
| 6,300,074 B1 | 10/2001 | Gold et al. | |
| 6,387,620 B1 | 5/2002 | Smith et al. | |
| 7,754,679 B2 | 7/2010 | Murthy | |
| 7,947,447 B2 | 5/2011 | Zichi et al. | |
| 8,105,982 B2 | 1/2012 | Doyle et al. | |
| 8,409,795 B2 | 4/2013 | Schneider et al. | |
| 2015/0147276 A1* | 5/2015 | Ingber et al. | C12N 15/111 |
| 2016/0287715 A1* | 10/2016 | Charles et al. | C12N 15/111 |

FOREIGN PATENT DOCUMENTS

| | | |
|---|---|---|
| WO | WO2005116255 | 12/2005 |
| WO | WO2013154735 | 10/2013 |

OTHER PUBLICATIONS

Abelow et al., Biomimetic glass nanopores employing aptamer gates responsive to a small molecule, 2010, Chem. Commun., vol. 46, pp. 7984-7986.
Albert et al., Cross-reactive chemical sensor arrays, 2000, Chem Rev., 2000, vol. 100, pp. 2595-2626.
Anzenbacher et al., A practical approach to optical cross-reactive sensor arrays, 2010, Chemical Society Reviews, vol. 39, pp. 3954-3979.
Baker et al., Widespread Genetic Switches and Toxicity Resistance Proteins for Fluoride, 2012 Science, vol. 335, pp. 233-235.
Balamurugan et al., Surface immobilization methods for aptamer diagnostic applications, 2008 Anal Bioanal Chem, vol. 390, pp. 1009-1021.
Brody et al., Aptamers as therapeutic and diagnostic agents, 2000, Reviews in Molecular Biotechnology, vol. 74, No. 1, pp. 5-13.
Buist, Set of simple side-room urine tests for detection of inborn errors of metabolism, 1968, British Medical Journal, vol. 2, pp. 745-749.
Burgstaller et al., Structural probing and damage selection of citrulline- and arginine-specific RNA aptamers identify base positions required for binding, 1995, Nucleic Acids Research, vol. 23, No. 23, pp. 4769-4776.
Buryak et al., A Chemosensor Array for the Colorimetric Identification of 20 Natural Amino Acids, 2005, J. Am. Chem. Soc., vol. 127, pp. 3700-3701.
Chace et al., Impact of Second-Tier Testing on the Effectiveness of Newborn Screening, 2010, Clinical Chemistry, vol. 56, No. 11, pp. 1653-1655.
Chen et al., Substractive SELEX against two heterogeneous target samples: Numerical simulations and analysis, 2007, Computers in Biology and Medicine, vol. 37, pp. 750-759.
Chin et al., A metal complex that binds α-amino acids with high and predictable stereospecificity, 1999, Nature, vol. 401, No. 6750, pp. 254-257.
Cho et al., In vitro selection of sialic acid specific RNA aptamer and its application to the rapid sensing of sialic acid modified sugars, 2013, Biotechnology & Bioengineering, vol. 110, No. 3, pp. 905-913.
Davis et al., Isolation of high-affinity GTP aptamers from partially structured RNA libraries, 2002, Proc. Natl. Acad. Sci. U.S.A., vol. 99, pp. 11616-11621.
Dietzen et al., The National Academy of Clinical Biochemistry Laboratory Medicine Practice Guidelines Follow-Up Testing for Metabolic Diseases Identified by Expanded Newborn Screening Using Tandem Mass Spectrometry; Executive Summary, 2009, Clinical Chemistry, vol. 55, No. 9, pp. 1615-1626.

(Continued)

*Primary Examiner* — Amy H Bowman
(74) *Attorney, Agent, or Firm* — Dentons US LLP

(57) ABSTRACT

Methods of selecting an aptamer that specifically binds to a target molecule complexed with a derivatization agent. Also disclosed are specific aptamers and methods of use thereof.

23 Claims, 17 Drawing Sheets

Specification includes a Sequence Listing.

(56) References Cited

OTHER PUBLICATIONS

Dillon et al., RNAI as an Experimental and Therapeutic Tool to Study and Regulate Physiological and Disease Processes, 2005, Annual Review of Physiology, vol. 67, pp. 147-173.
Dykxhoorn et al., The silent revolution: RNA interference as basic biology, research tool, and therapeutic, 2005, Annual Review of Medicine, vol. 56, pp. 401-423.
Elhai et al., Conjugal transfer of DNA to cyanobacteria, 1988, Methods in Enzymology, vol. 167, pp. 747-754.
Ellington et al., In vitro selection of RNA molecules that bind specific ligands, 1990, Nature, vol. 346, pp. 818-822.
Famulok et al., Functional aptamers and aptazymes in biotechnology, diagnostics, and therapy, 2007, Chemical Reviews, vol. 107, No. 9, pp. 3715-3743.
Famulok, Molecular recognition of amino acids by RNA-aptamers: an L-citrulline binding RNA motif and its evolution into an L-arginine binder, 1994, J. Am. Chem. Soc., vol. 116, No. 5, pp. 1698-1706.
Fang et al., Progress in Boronic Acid-Based Fluorescent Glucose Sensors, 2004, Journal of Fluorescence, vol. 14, No. 5, pp. 481-489.
Fanning et al., Gene-expressed RNA as a therapeutic: issues to consider, using ribozymes and small hairpin RNA as specific examples, 2006, Handb. Exp. Pharmacol., vol. 173, pp. 289-303.
Fenton et al., Chiral metal complexes 44. Enantiomeric discrimination in ternary cobalt (III) complexes of N,N-dimethyl-N,N-di(2-picolyl)-1S,2S-dianrinocyclohexane and α-amino acids; including the crystal structure of the S-prolinato complex, 1995, Inorganic Chimica Acta, vol. 236, pp. 109-115.
Fyro, Neonatal screening: life-stress scores in families given a false-positive result, 1988, Acta Paediatr Scand, vol. 77, pp. 232-238.
Geiger et al., RNA aptamers that bind L-arginine with sub-micromolar dissociation constants and high enantioselectivity, 1996, Nucleic Acids Research, vol. 24, No. 6, pp. 1029-1036.
Ghadessy et al., Directed evolution of polymerase function by compartmentalized self-replication, 2001, Proc Natl Acad Sci USA, vol. 98, No. 8, pp. 4552-4557.
Gold et al., Aptamer-based multiplexed proteomic technology for biomarker discovery, 2010, PloS One, vol. 5, No. e15004, 17 pages.
Green et al., Rational Approach to Minimal High-Resolution Cross-Reactive Arrays, 2006, Journal of American Chemical Society, vol. 128, pp. 15278-15282.
Guernion et al., Identifying bacteria in human mine: current practice and the potential for rapid, near-patient diagnosis by sensing volatile organic compounds, 2001, Clin. Chem. Lab. Med., vol. 39, pp. 893-906.
Gurian et al., Expanded Newborn Screening for Biochemical Disorders: The Effect of a False-Positive Result Pediatrics, 2006, vol. 117, No. 6, pp. 1915-1921.
Haddou et al., Achieving Large Color Changes in Response to the Presence of Amino Acids: A Molecular Sensing Ensemble with Selectivity for Aspartate, 2001, J. Am. Chem. Soc., vol. 123, pp. 11296-11297.
He et al., X-Aptamers: A Bead-Based Selection Method for Random Incorporation of Drug-like Moieties onto Next-Generation Aptamers for Enhanced Binding, 2012, Biochemistry, vol. 51, No. 42, pp. 8321-8323.
Helene, C. et al., Control of Gene Expression by Triple Helix-Forming Oligonucleotides, The Antigen Strategy, 1992, Annals New York Academy of Sciences, pp. 27-36.
Hess et al., Dependence of urine composition on the age and sex of healthy subjects, 1986, Clinica Chimica Acta, vol. 160, pp. 79-86.
Huber, Projection Pursuit, 1985, The Annals of Statistics, vol. 13, No. 2, pp. 435-475.
Huizenga et al., A DNA aptamer that binds adenosine and ATP, 1995, Biochemistry, vol. 34, pp. 656-665.
International Search Report and Written Opinion dated Aug. 11, 2014 in related PCT Application No. PCT/US14/29281 filed Mar. 14, 2014 (9 pages).
Jarosch et al., In vitro selection using a dual RNA library that allows primerless selection, 2006 Nucleic Acids Research, vol. 34, No. 12, 9 pages and Supplementary Information 2 pages, total pp. 11.
Jayasena, Aptamers: an emerging class of molecules that rival antibodies in diagnostics, 1999, Clinical Chemistry, vol. 45, No. 9, pp. 1628-1650.
Job et al., Chiral Recognition of Prochiral Centers. The (2S,9S)-2,9-Diamino-4 7-diazadecanecobalt(III) Mediated Decarboxylation of Aminoalkylmalonic Acids, 1974, Journal of Ameircan Chemical Society, vol. 96, No. 3, pp. 809-819.
Karnik et al., Tyrosinemia Type I : A Clinico-Laboratory Case Report, 2004, Indian Journal of Pediatrics, vol. 71, No. 10, pp. 929-932.
Kaspar et al., Urinary Amino Acid Analysis: A Comparison of iTRAQ®-LC-MS/MS, GC-MS, and Amino Acid Analyzer, 2009, Journal of Chromatography B, vol. 877, pp. 1838-1846.
Kato et al., In vitro selection of DNA aptamers which bind to cholic acid, 2000, Biochimica Biophysica Acta, vol. 1493, pp. 12-18.
Kato et al., Interaction of three-way DNA junctions with steroids, 2000, Nucleic Acids Research, vol. 28, No. 9, pp. 1963-1968.
Kawano et al., Rapid detection of a cocaine-binding atpamer using biological nanopores on a chip, 2011, Journal of the American Chemical Society, vol. 133, 4 pages, and Supplementary Information 8 pages, total 12 pages.
Kim et al., Characterization of Late-Onset Citrullinemia 1 in a Korean Patient: Confirmation by Argininosuccinate Synthetase Gene Mutation Analysis, 2006, Journal of Biochemistry and Molecular Biology, vol. 39,pp. 400-405.
Kurczynski et al., Maternal homocystinuria: studies of an untreated mother and fetus, 1980, Arch Dis Child, vol. 55, pp. 721-723.
Kvittingen, Hereditary tyrosinemai type I—an overview, 1986, Scand J Clin Lab Invest, vol. 46, pp. 27-34.
Kwon et al., The magnitude and challenge of false-positive newborn screening test results, 2000, Arch. Pediatr. Adolesc. Med., vol. 154, No. 7, pp. 714-718.
Lavigne et al., Sensing a paradigm shift in the field of molecular recognition: from selective to differential receptors, 2001, Angew. Chem. Int. Ed., vol. 40, pp. 3118-3130.
Lee et al., Biomarker discovery from the plasma proteome using multidimensional fractionation proteonics, 2006, Current Opinion in Chemical Biology, vol. 10, pp. 42-49.
Lee et al., Molecular diagnostic and drug delivery agents based on aptamer-nanomaterial conjugates, 2010, Advanced Drug Delivery Reviews, vol. 62, No. 6, pp. 592-605.
Legiewicz et al., A More Complex Isoleucine Aptamer with a Cognate Triplet, 2005, The Journal of Biological Chemistry, vol. 280, No. 20, pp. 19815-19822.
Levine et al., A mathematical Analysis of SELEX, 2007, Computational Biology and Chemistry, vol. 31, pp. 11-35.
Li et al., Selecting Aptamers for a Glycoprotein through the Incorporation of the Boronic Acid Moiety, 2008, J. Am. Chem Soc., vol. 130, No. 38, 3 pages, and Supplementary Information 20 pages, total 23 pages.
Lindner et al., Efficacy and outcome of expanded newborn screening for metabolic diseases—report of 10 years from South-West Germany, 2011, Orphanet Journal of Rare Diseases, vol. 6, No. 44, 10 pages.
Link et al., Beyond toothpicks: new methods for isolating mutant bacteria, 2007, Nature Reviews, vol. 5, No. 9, pp. 680-688.
Lipinski, Drug-like properties and the causes of poor solubility and poor permeability, 2000, Journal of Pharmacological and Toxicological Methods, vol. 44, pp. 235-249.
Liu et al., Aptamer-Based Origami Paper Analytical Device for Electrochemical Detection of Adenosine, 2012, Angew. Chem. Int. Ed., vol. 51, pp. 6925-6928.
Lowary et al., New DNA sequence rules for high affinity binding to histone octamer and sequence-directed nucleosome positioning, 1998, Journal of Molecular Biology, vol. 276, No. 1, pp. 19-42.
Lozupone et al., Selection of the simplest RNA that binds isoleucine, 2003, RNA, vol. 9, pp. 1315-1322.
Maher, DNA triple-helix formation: An approach to artificial gene repressors?, 1992, Bioassays, vol. 14, No. 12, pp. 807-815.

(56) References Cited

OTHER PUBLICATIONS

Majerfeld et al., A diminutive and specific RNA binding site for L-tryptophan, 2005, Nucleic Acids Research, vol. 33, No. 17, pp. 5482-5493.
Majerfeld et al., An RNA pocket for an aliphatic hydrophobe, 1994, Structural Biology, vol. 1, No. 5, pp. 287-292.
Majerfeld et al., Isoleucine:RNA sites with associated coding sequences, 1998, RNA, vol. 4, pp. 471-478.
Majerfeld et al., RNA affinity for molecular L-histidine; genetic code origins, 2005, J Mol Evol., vol. 61, No. 2, pp. 226-235.
Mandal et al., A glycine-dependent riboswitch that uses cooperative binding to control gene expression, 2004, Science, vol. 306, 6 pages, corrected data, 1 page and supplemental data, 13 pages, total pp. 20, Correction Information 1 page and Supplemental Information 13 pages, total pp. 34 pages.
Manimala et al., Tuning the Specificity of a Synthetic Receptor Using a Selected Nucleic Acid Receptor, 2004, J. Am Chem. Soc., vol. 126, pp. 16515-16519.
Mannironi et al., Molecular recognition of amino acids by RNA aptamers: The evolution into an L-tyrosine binder of a dopamine-binding RNA motif, 2000, RNA, vol. 6, pp. 520-527.
Matsumoto et al., A New Chemical Diagnostic Method for Inborn Errors of Metabolism by Mass Spectrometry—Rapid, Practical, and Simultaneous Urinary Metabolites Analysis, 1996, Mass Spectrometry Reviews, vol. 15, pp. 43-57.
Morton et al., Diagnosis and Treatment of Mapple Syrup Disease: A Study of 36 Patients, 2002, Pediatrics; vol. 109, No. 6, 12 pages.
Natale et al., A. Electronic nose analysis of urine samples containing blood, 1999, Physiol. Meas., vol. 20, pp. 377-384.
Nguyen et al., Indicator Displacement Assay, 2006, Coordination Chemistry Reviews, vol. 250, pp. 3118-3127.
Nimjee et al., Aptamers: an emerging class of therapeutics, 2005, Annual Review of Medicine, vol. 56, pp. 555-583.
Nutiu et al., In vitro selection of structure-switching signaling aptamers, 2005, Angew.Chem. Int. Ed., vol. 44, 5 pages and Supplemental Information 4 pages, total pp. 9.
Oglesbee et al., Second-tier test for quantification of alloisoleucine and branched-chain amino acids in dried blood spots to improve newborn screening for maple syrup urine disease (MSUD), 2008, Clinical Chemistry, vol. 54, No. 3, pp. 542-549.
Oliphant et al., Defining the sequence specificity of DNA-binding proteins by selecting binding sites from random-sequence oligonucleotides: analysis of yeast GCN4 proteins, 1989, Molecular and Cellular Biology, vol. 9, No. 7, pp. 2944-2949.
Palmer et al., Urinary excretion of arginino-succinic acid, 1973, Clinica Chimica Acta, vol. 47, pp. 443-448.
Patel et al., Structure, recognition and discrimination in RNA aptamer complexes with cofactors, amino acids, drugs and aminoglycoside antibiotics, 2000, Reviews in Molecular Biotechnology, vol. 74, pp. 39-60.
Pavlou et al., Use of an electronic nose system for diagnoses of urinary tract infections, 2002, Biosensors and Bioelectronics, vol. 17, pp. 893-899.
Pei et al., High-resolutions cross-reactive array for alkaloids, 2009, Chem. Com., pp. 3193-3195.
Purschke et al., An L-RNA-based aquaretic agent that inhibits vasopressin in vivo, 2006, Proc. Natl. Acad. Sci. USA, vol. 103, No. 13, pp. 5173-5178.
Pushparaj et al., Short Intefering RNA (siRNA) as a novel therapeutic, 2006, Clinical and Experimental Pharmacology and Physiology, vol. 33, pp. 504-510.
Rajendran et al., In vitro selection of molecular beacons, 2003, Nucleic Acids Research, vol. 31, No. 19, pp. 5700-5713.
Reynolds et al., Rational siRNA design for RNA interference, 2004, Nature Biotechnology, vol. 22, No. 3, pp. 326-330.
Robertson et al., Selection in vitro of an RNA enzyme that specifically cleaves single-stranded DNA, 1990, Nature, vol. 344, pp. 467-468.
Rochat et al., Cross-Reactive Sensor Arrays for the Detection of Peptides in Aqueous Solution by Fluorescence Spectroscopy, 2010, Chem. Eur. J., vol. 16, pp. 104-113.
Roeck et al., Electronic Nose: Current Status and Future Trends, 2008, Chemical Reviews, vol. 108, No. 2, pp. 705-725.
Sagner et al., Rapid filter assay for the detection of DNA polymerase activity: direct identification of the gene for the DNA polymerase from Thermus aquaticus, 1991, Gene, vol. 97, pp. 119-123.
Sanles-Sobrido et al., Highly Active Nanoreactors: Nanomaterial Encapsulation Based on Confined Catalysis, 2012, Angewandte Chemie, vol. 124, pp. 3943-3948.
Schauer et al., Cross-Reactive Optical Sensing Arrays, 2002, American Chemical Society, Symposium Series, vol. 825, Ch. 23, pp. 318-329.
Schuitt, Modified Nucleoside Triphosphate Applications: An Overview of the SELEX Process, 2002, TriLink Biotechnologies, 2 pages.
Schulze et al., Expanded newborn screening for inborn errors of metabolism by electrospray ionization-tandem mass spectrometry: results, outcome, and implications, 2003, Pediatrics, vol. 111, No. 6, pp. 1399-1406.
Seo et al., A mathematical analysis of multiple-target SELEX, 2010, Bulletin of Mathematical Biology, vol. 72, pp. 1623-1625.
Shangguan et al., Aptamers evolved from live cells as effective molecular probes for cancer study, 2006, PNAS, vol. 103, No. 32, pp. 11838-11843.
Stojanovic et al., Aptamer-based colorimetric sensor for cocaine, 2002, J. Am. Chem. Soc., vol. 124, No. 33, pp. 9678-9679.
Stojanovic et al., Aptamer-based folding fluorescent sensor for cocaine, 2001, J. Am. Chem. Soc., vol. 123, 4 pages, Supplemental Information 1 page, total 5 pages.
Stojanovic et al., Cross-reactive arrays based on three-way junctions, 2003, J. Am. Chem. Soc. vol. 125, No. 20, 5 pages, Supplemental Information No. 1, 3 pages, and Supplemental Information No. 2, 3 pages, total 11 pages.
Stojanovic, et al., Fluorescent sensors based on aptamer self-assembly, 2000, J. Am. Chem. Soc., vol. 122, 2 pages and Supplemental Information 1 page, total 3 pages.
Studier, Protein production by auto-induction in high-density shaking cultures, 2005, Protein Expression & Purification, vol. 41, pp. 207-234.
Tang et al., Tight Binding and Fluorescent Sensing of Oxalate in Water, 2008, J. Am. Chem. Soc., vol. 130, 2 pages and Supplemental Information 6 pages, total 8 pages.
Tarini et al., State newborn screening in the tandem mass spectrometry era: more tests, more false-positive results, 2006, Pediatrics; vol. 118, pp. 448-456.
Tombelli et al., Analytical applications of aptamers, 2005, Biosensors and Bioelectronics, vol. 20, pp. 2424-2434.
Tuerk et al., Systematic evolution of ligands by exponential enrichment: RNA ligands to bacteriophage T4 DNA polymerase, 1990, Science, vol. 249, pp. 505-510.
Turner et al., Electronic noses and disease diagnostics, 2004, Nature Reviews—Microbiology, vol. 2, pp. 161-166.
Usha et al., Newborn Screening—From Guthrie age to Genomic age, 2010, J. Obstet. Gynecol. India, vol. 60, pp. 210-220.
Vant-Hull et al., The mathematics of SELEX against complex targets, 1997, J. Mol. Biol., vol. 278, pp. 579-597.
Vaught, et al., Expanding the Chemistry of DNA for in Vitro Selection, 2010, J. Am. Chem. Soc., vol. 132, pp. 4141-4151.
Weng et al., Screening of aptamers on microfluidic systems for clinical applications, 2012, Sensors, vol. 12, pp. 9514-9529.
Yamaguchi et al., Asymmetric transformation of a-Amino acids promoted by optically active cobalt (III) complexes, 1980, Inorganic Chemistry, vol. 19, 7 pages and Supplemental Information 45 pages, total 52 pages.
Yang et al., Optimizing Cross-reactivity with Evolutionary Search for Sensors, 2012, Journal of the American Chemical Society, vol. 134, 6 pages and Supplemental Information 4 pages, total 10 pages.
Yang et al., Recognition and sensing of low-epitope targets via ternary complexes with oligonucleotides and synthetic receptors, 2014, Nature Chemistry, vol. 6, pp. 1003-1008.

(56) References Cited

OTHER PUBLICATIONS

Yarus, Amino Acids as RNA Ligands: A Direct-RNA-Template Theory for the Code's Origin, 1998, Journal of Molecular Evolution, vol. 47, pp. 109-117.
Zadeh et al., NUPACK: analysis and design of nucleic acid systems, 2011, Journal of Computational Chemistry 32: 170-173.
Zhou et al., Recent progress in fluorescent and colorimetric chemosensors for detection of amino acids, 2012, Chem. Soc. Rev., vol. 41, pp. 52-67.
Zuker, Mfold web server for nucleic acid folding and hybridization prediction, 2003, Nucleic Acids Research, vol. 31, No. 13, 10 pages and Supplemental Information 15 pages, total 25 pages.

* cited by examiner

A.

B.

organometallic receptors
(metal, on left, complexed to organic ligand, on right)

C.

D.

E.

A.

B.

SEQ ID NO: 81

C.

SEQ ID NO: 80
SEQ ID NO: 36

D.

E.

F.

G.

Kd ~ 60 nM

H.

*No cofactor*

Kd ~ 6 µM

I.

J.

A.

B.

SEQ ID NO: 85

C.

SEQ ID NO: 86

SEQ ID NO: 18

D.

E.

F.

G.

H.

I.

J.

K.

L.

M.

N.

A

B

SEQUENCE LISTING

<160> NUMBER OF SEQ ID NOS: 89

<210> SEQ ID NO 1
<211> LENGTH: 13
<212> TYPE: DNA
<213> ORGANISM: Artificial Sequence
<220> FEATURE:
<223> OTHER INFORMATION: synthetic DNA sequence; 5' primer end of
      library oligonucleotides

<400> SEQUENCE: 1
ctctcgggac gac                                                      13

<210> SEQ ID NO 2
<211> LENGTH: 8
<212> TYPE: DNA
<213> ORGANISM: Artificial Sequence
<220> FEATURE:
<223> OTHER INFORMATION: synthetic DNA sequence; 3' primer end of
      library oligonucleotides

<400> SEQUENCE: 2 gtcgtccc                                                             8

<210> SEQ ID NO 3
<211> LENGTH: 29
<212> TYPE: DNA
<213> ORGANISM: Artificial Sequence
<220> FEATURE:
<223> OTHER INFORMATION: synthetic DNA sequence; Aptamer against
      glucose-boronic acid complex; Short binding form

<400> SEQUENCE: 3
gacagccgag tgcattcaac agccgagtc                                     29

<210> SEQ ID NO 4
<211> LENGTH: 49
<212> TYPE: DNA
<213> ORGANISM: Artificial Sequence
<220> FEATURE:
<223> OTHER INFORMATION: synthetic DNA sequence; Glucose-BA_01

<400> SEQUENCE: 4
ctcgggacga cagccgagtt cagggattcc ctaacagccg agtcgtccc               49

<210> SEQ ID NO 5
<211> LENGTH: 49
<212> TYPE: DNA
<213> ORGANISM: Artificial Sequence
<220> FEATURE:
<223> OTHER INFORMATION: synthetic DNA sequence; Glucose-BA_07

<400> SEQUENCE: 5
ctcgggacga cagccgagtt atgacattca ataacagccg agtcgtccc        49

<210> SEQ ID NO 6
<211> LENGTH: 49
<212> TYPE: DNA
<213> ORGANISM: Artificial Sequence
<220> FEATURE:
<223> OTHER INFORMATION: synthetic DNA sequence; Glucose-BA_08

<400> SEQUENCE: 6
ctcgggacga ccagccgaga ttttgcataa aaacagccga ggtcgtccc        49

<210> SEQ ID NO 7
<211> LENGTH: 49
<212> TYPE: DNA
<213> ORGANISM: Artificial Sequence
<220> FEATURE:
<223> OTHER INFORMATION: synthetic DNA sequence; Glucose-BA_09

<400> SEQUENCE: 7
ctcgggacga ccagccgaga taggtcgttc tatcagccga ggtcgtccc        49

<210> SEQ ID NO 8
<211> LENGTH: 49
<212> TYPE: DNA
<213> ORGANISM: Artificial Sequence
<220> FEATURE:
<223> OTHER INFORMATION: synthetic DNA sequence; Glucose-BA_10

<400> SEQUENCE: 8
ctcgggacga caaccgagta ggatactaag catccagcgg agtcgtccc        49

<210> SEQ ID NO 9
<211> LENGTH: 49
<212> TYPE: DNA
<213> ORGANISM: Artificial Sequence
<220> FEATURE:
<223> OTHER INFORMATION: synthetic DNA sequence; Glucose-BA_11

<400> SEQUENCE: 9
ctcgggacga cagccgagga aacaaacttt tttccagccg agtcgtccc        49

<210> SEQ ID NO 10
<211> LENGTH: 49
<212> TYPE: DNA
<213> ORGANISM: Artificial Sequence
<220> FEATURE:
<223> OTHER INFORMATION: synthetic DNA sequence; Glucose-BA_12

<400> SEQUENCE: 10
ctcgggacga ccgcgggagc aatgcgatga cgaaggacgg ggtcgtccc        49

<210> SEQ ID NO 11
<211> LENGTH: 48
<212> TYPE: DNA
<213> ORGANISM: Artificial Sequence
<220> FEATURE:
<223> OTHER INFORMATION: synthetic DNA sequence; Glucose-BA_13

<400> SEQUENCE: 11
ctcgggacga ccggagctcc tgcgattgac taaaaggaag gtcgtccc         48

<210> SEQ ID NO 12
<211> LENGTH: 49
<212> TYPE: DNA

```
<213> ORGANISM: Artificial Sequence
<220> FEATURE:
<223> OTHER INFORMATION: synthetic DNA sequence; Glucose-BA_14

<400> SEQUENCE: 12
ctcgggacga cagccgagtc aaagtttaac ttgacagccg agtcgtccc                    49

<210> SEQ ID NO 13
<211> LENGTH: 49
<212> TYPE: DNA
<213> ORGANISM: Artificial Sequence
<220> FEATURE:
<223> OTHER INFORMATION: synthetic DNA sequence; Glucose-BA_15

<400> SEQUENCE: 13
ctcgggacga cggggaacgt tttcgtggat gagctggcga cgtcgtccc                    49

<210> SEQ ID NO 14
<211> LENGTH: 49
<212> TYPE: DNA
<213> ORGANISM: Artificial Sequence
<220> FEATURE:
<223> OTHER INFORMATION: synthetic DNA sequence; Glucose-BA_16

<400> SEQUENCE: 14
ctcgggacga cggggagag tattggatga ccgcagggac cgtcgtccc                     49

<210> SEQ ID NO 15
<211> LENGTH: 49
<212> TYPE: DNA
<213> ORGANISM: Artificial Sequence
<220> FEATURE:
<223> OTHER INFORMATION: synthetic DNA sequence; Glucose-BA_17

<400> SEQUENCE: 15
ctcgggacga cgggggaac attgtgatct cgttagagca cgtcgtccc                     49

<210> SEQ ID NO 16
<211> LENGTH: 51
<212> TYPE: DNA
<213> ORGANISM: Artificial Sequence
<220> FEATURE:
<223> OTHER INFORMATION: synthetic DNA sequence; GLUBA02

<400> SEQUENCE: 16
ctctcgggac gacggaccgt taggggagcc agtgcgcgat gacgtcgtcc c                 51

<210> SEQ ID NO 17
<211> LENGTH: 52
<212> TYPE: DNA
<213> ORGANISM: Artificial Sequence
<220> FEATURE:
<223> OTHER INFORMATION: synthetic DNA sequence; GLUBA09

<400> SEQUENCE: 17
ctctcgggac gacagccgag ttcagggact tccctaacag ccgagtcgtc cc                52

<210> SEQ ID NO 18
<211> LENGTH: 44
<212> TYPE: DNA
<213> ORGANISM: Artificial Sequence
<220> FEATURE:
<223> OTHER INFORMATION: synthetic DNA sequence; GLUBA09_M1

<400> SEQUENCE: 18
ctctcgggac gacagccgag ttgattcaac agccgagtcg tccc                         44
```

<210> SEQ ID NO 19
<211> LENGTH: 51
<212> TYPE: DNA
<213> ORGANISM: Artificial Sequence
<220> FEATURE:
<223> OTHER INFORMATION: synthetic DNA sequence; GLUBA17

<400> SEQUENCE: 19
ctctcgggac gacagccgag cactacatta gttgggcagc cgagtcgtcc c    51

<210> SEQ ID NO 20
<211> LENGTH: 51
<212> TYPE: DNA
<213> ORGANISM: Artificial Sequence
<220> FEATURE:
<223> OTHER INFORMATION: synthetic DNA sequence; GLUBAN3W10

<400> SEQUENCE: 20
ctctcgggac gacgaccgta ggggtagctg tatatgcgga tgagtcgtcc c    51

<210> SEQ ID NO 21
<211> LENGTH: 51
<212> TYPE: DNA
<213> ORGANISM: Artificial Sequence
<220> FEATURE:
<223> OTHER INFORMATION: synthetic DNA sequence; GLUBAN3W11

<400> SEQUENCE: 21
ctctcgggac gacaggggt aggggggcccg gactgttaag ggtgtcgtcc c    51

<210> SEQ ID NO 22
<211> LENGTH: 51
<212> TYPE: DNA
<213> ORGANISM: Artificial Sequence
<220> FEATURE:
<223> OTHER INFORMATION: synthetic DNA sequence; GLUBAN3W19

<400> SEQUENCE: 22
ctctcgggac gacgggacca accgggatga gcataagtgc gacgtcgtcc c    51

<210> SEQ ID NO 23
<211> LENGTH: 51
<212> TYPE: DNA
<213> ORGANISM: Artificial Sequence
<220> FEATURE:
<223> OTHER INFORMATION: synthetic DNA sequence; FrucBA02

<400> SEQUENCE: 23
ctctcgggac gacggctggc acgtttggtt caagaatgtg ggtgtcgtcc c    51

<210> SEQ ID NO 24
<211> LENGTH: 43
<212> TYPE: DNA
<213> ORGANISM: Artificial Sequence
<220> FEATURE:
<223> OTHER INFORMATION: synthetic DNA sequence; FrucBA02_M1

<400> SEQUENCE: 24
ctctcgggac gacggctggc acgttgaatg tgggtgtcgt ccc    43

<210> SEQ ID NO 25
<211> LENGTH: 51
<212> TYPE: DNA
<213> ORGANISM: Artificial Sequence
<220> FEATURE:

<223> OTHER INFORMATION: synthetic DNA sequence; FrucBA05

<400> SEQUENCE: 25
ctctcgggac gacggacaga ggttcgagcg tgcgctctag gaagtcgtcc c          51

<210> SEQ ID NO 26
<211> LENGTH: 51
<212> TYPE: DNA
<213> ORGANISM: Artificial Sequence
<220> FEATURE:
<223> OTHER INFORMATION: synthetic DNA sequence; GalacBA01

<400> SEQUENCE: 26
ctctcgggac gacccaggtg tcctgcttct cagtagtagg ttagtcgtcc c          51

<210> SEQ ID NO 27
<211> LENGTH: 51
<212> TYPE: DNA
<213> ORGANISM: Artificial Sequence
<220> FEATURE:
<223> OTHER INFORMATION: synthetic DNA sequence; GalacBA04

<400> SEQUENCE: 27
ctctcgggac gaccactacg catagtttct atcgccagga agggtcgtcc c          51

<210> SEQ ID NO 28
<211> LENGTH: 51
<212> TYPE: DNA
<213> ORGANISM: Artificial Sequence
<220> FEATURE:
<223> OTHER INFORMATION: synthetic DNA sequence; GalacBA06

<400> SEQUENCE: 28
ctctcgggac gaccgagtag gtgtcctgga tgcaggtttg gaggtcgtcc c          51

<210> SEQ ID NO 29
<211> LENGTH: 51
<212> TYPE: DNA
<213> ORGANISM: Artificial Sequence
<220> FEATURE:
<223> OTHER INFORMATION: synthetic DNA sequence; BAOnly01

<400> SEQUENCE: 29
ctctcgggac gaccaggtgg ggctgctcaa gtggaggttc ctcgtcgtcc c          51

<210> SEQ ID NO 30
<211> LENGTH: 51
<212> TYPE: DNA
<213> ORGANISM: Artificial Sequence
<220> FEATURE:
<223> OTHER INFORMATION: synthetic DNA sequence; BAOnly03

<400> SEQUENCE: 30
ctctcgggac gaccagaggg gcctcaaatg tggggtgttg ctcgtcgtcc c          51

<210> SEQ ID NO 31
<211> LENGTH: 38
<212> TYPE: DNA
<213> ORGANISM: Artificial Sequence
<220> FEATURE:
<223> OTHER INFORMATION: synthetic DNA sequence; Aptamer against
      Arginine-CpRh complex; Short binding form

<400> SEQUENCE: 31
gacgacacgg gcgtcccta tcacaaggag agtgagtc                          38

<210> SEQ ID NO 32
<211> LENGTH: 51
<212> TYPE: DNA
<213> ORGANISM: Artificial Sequence
<220> FEATURE:
<223> OTHER INFORMATION: synthetic DNA sequence; Arginine-CpRh_02

<400> SEQUENCE: 32
ctctcgggac gacgggtgtc cctgtggacc tgtacatagg agagtcgtcc c    51

<210> SEQ ID NO 33
<211> LENGTH: 51
<212> TYPE: DNA
<213> ORGANISM: Artificial Sequence
<220> FEATURE:
<223> OTHER INFORMATION: synthetic DNA sequence; Arginine-CpRh_03

<400> SEQUENCE: 33
ctctcgggac gacgcgggtg tcccttggta aaccaaggag agtgtcgtcc c    51

<210> SEQ ID NO 34
<211> LENGTH: 51
<212> TYPE: DNA
<213> ORGANISM: Artificial Sequence
<220> FEATURE:
<223> OTHER INFORMATION: synthetic DNA sequence; Arginine-CpRh_04

<400> SEQUENCE: 34
ctctcgggac gacggctagg agaggtgtcc gggtgtccca ggtgtcgtcc c    51

<210> SEQ ID NO 35
<211> LENGTH: 43
<212> TYPE: DNA
<213> ORGANISM: Artificial Sequence
<220> FEATURE:
<223> OTHER INFORMATION: synthetic DNA sequence; Arginine-CpRh_05

<400> SEQUENCE: 35
ctctcgggac gacccacgag agactccaaa cgattgccgt ccc    43

<210> SEQ ID NO 36
<211> LENGTH: 51
<212> TYPE: DNA
<213> ORGANISM: Artificial Sequence
<220> FEATURE:
<223> OTHER INFORMATION: synthetic DNA sequence; ARG01_Cp

<400> SEQUENCE: 36
ctctcgggac gacgacacgg gcgtcccttc acaaggagag tgagtcgtcc c    51

<210> SEQ ID NO 37
<211> LENGTH: 51
<212> TYPE: DNA
<213> ORGANISM: Artificial Sequence
<220> FEATURE:
<223> OTHER INFORMATION: synthetic DNA sequence; AspaCp01

<400> SEQUENCE: 37
ctctcgggac gacggcactt gttgcgtgaa gcgtatgcga atagtcgtcc c    51

<210> SEQ ID NO 38
<211> LENGTH: 51
<212> TYPE: DNA
<213> ORGANISM: Artificial Sequence
<220> FEATURE:
<223> OTHER INFORMATION: synthetic DNA sequence; AspaCp03

<400> SEQUENCE: 38
ctctcgggac gacgggccac gttttccagg tactttctaa ggggtcgtcc c       51

<210> SEQ ID NO 39
<211> LENGTH: 51
<212> TYPE: DNA
<213> ORGANISM: Artificial Sequence
<220> FEATURE:
<223> OTHER INFORMATION: synthetic DNA sequence; AspaCp04

<400> SEQUENCE: 39
ctctcgggac gacgggcctt cggtggctga gcatagcgat ggggtcgtcc c       51

<210> SEQ ID NO 40
<211> LENGTH: 51
<212> TYPE: DNA
<213> ORGANISM: Artificial Sequence
<220> FEATURE:
<223> OTHER INFORMATION: synthetic DNA sequence; CIT30N02_CpRh

<400> SEQUENCE: 40
ctctcgggac gacggcgggg aaacagctgc aaaatgtgga gtagtcgtcc c       51

<210> SEQ ID NO 41
<211> LENGTH: 51
<212> TYPE: DNA
<213> ORGANISM: Artificial Sequence
<220> FEATURE:
<223> OTHER INFORMATION: synthetic DNA sequence; GlutaCp02

<400> SEQUENCE: 41
ctctcgggac gacggcgggt gaatgcacac ttagcagaga gtagtcgtcc c       51

<210> SEQ ID NO 42
<211> LENGTH: 51
<212> TYPE: DNA
<213> ORGANISM: Artificial Sequence
<220> FEATURE:
<223> OTHER INFORMATION: synthetic DNA sequence; GlutaCp15

<400> SEQUENCE: 42
ctctcgggac gacggcgggg aaaggaccct agttcctggt gtagtcgtcc c       51

<210> SEQ ID NO 43
<211> LENGTH: 35
<212> TYPE: DNA
<213> ORGANISM: Artificial Sequence
<220> FEATURE:
<223> OTHER INFORMATION: synthetic DNA sequence; Aptamer against
      Glycine-CpRh complex; Short binding form

<400> SEQUENCE: 43
gacgggctag gcgtgggtgt aaaggcacag gggtc                         35

<210> SEQ ID NO 44
<211> LENGTH: 49
<212> TYPE: DNA
<213> ORGANISM: Artificial Sequence
<220> FEATURE:
<223> OTHER INFORMATION: synthetic DNA sequence; Glycine-CpRh_01

<400> SEQUENCE: 44
tcgggacgac gggctaggcg tgggtgtaaa ggcacagggg tcgtcccga          49

-continued

```
<210> SEQ ID NO 45
<211> LENGTH: 50
<212> TYPE: DNA
<213> ORGANISM: Artificial Sequence
<220> FEATURE:
<223> OTHER INFORMATION: synthetic DNA sequence; Gly-Cp sensor

<400> SEQUENCE: 45
ctctcgggac gacgggctag gcgtgggtgt aaaggcacag gggtcgtccc             50

<210> SEQ ID NO 46
<211> LENGTH: 51
<212> TYPE: DNA
<213> ORGANISM: Artificial Sequence
<220> FEATURE:
<223> OTHER INFORMATION: synthetic DNA sequence; Gly-Cp sensor+1bp

<400> SEQUENCE: 46
ctctcgggac gacgggctag gcgtgggtgt aaaggcacag gggtcgtccc g           51

<210> SEQ ID NO 47
<211> LENGTH: 51
<212> TYPE: DNA
<213> ORGANISM: Artificial Sequence
<220> FEATURE:
<223> OTHER INFORMATION: synthetic DNA sequence; GLYHW-CpRh 06

<400> SEQUENCE: 47
ctctcgggac gacgggtcag ttagaccgtg aggcttccga atagtcgtcc c           51

<210> SEQ ID NO 48
<211> LENGTH: 51
<212> TYPE: DNA
<213> ORGANISM: Artificial Sequence
<220> FEATURE:
<223> OTHER INFORMATION: synthetic DNA sequence; LeuCp01

<400> SEQUENCE: 48
ctctcgggac gacggcgggg gtcccagcgt tgcatggtgt gtagtcgtcc c           51

<210> SEQ ID NO 49
<211> LENGTH: 51
<212> TYPE: DNA
<213> ORGANISM: Artificial Sequence
<220> FEATURE:
<223> OTHER INFORMATION: synthetic DNA sequence; LeuCp04

<400> SEQUENCE: 49
ctctcgggac gacggcgggc gcgtgatcgg agagaaaggt gtagtcgtcc c           51

<210> SEQ ID NO 50
<211> LENGTH: 51
<212> TYPE: DNA
<213> ORGANISM: Artificial Sequence
<220> FEATURE:
<223> OTHER INFORMATION: synthetic DNA sequence; LeuCp17

<400> SEQUENCE: 50
ctctcgggac gacggcgggc gcgtatgtat atcataaggt gtagtcgtcc c           51

<210> SEQ ID NO 51
<211> LENGTH: 51
<212> TYPE: DNA
<213> ORGANISM: Artificial Sequence
<220> FEATURE:
<223> OTHER INFORMATION: synthetic DNA sequence; LysCp05
```

<400> SEQUENCE: 51
ctctcgggac gacgcggtgt ggatccctcg tagaaggagt agtgtcgtcc c                51

<210> SEQ ID NO 52
<211> LENGTH: 51
<212> TYPE: DNA
<213> ORGANISM: Artificial Sequence
<220> FEATURE:
<223> OTHER INFORMATION: synthetic DNA sequence; LysCpRh18

<400> SEQUENCE: 52
ctctcgggac gacgggtggg agcgattcga gctactcagg tatgtcgtcc c                51

<210> SEQ ID NO 53
<211> LENGTH: 51
<212> TYPE: DNA
<213> ORGANISM: Artificial Sequence
<220> FEATURE:
<223> OTHER INFORMATION: synthetic DNA sequence; PACpRh01

<400> SEQUENCE: 53
ctctcgggac gacggacgct aatcttacaa gggcgtagtg tatgtcgtcc c                51

<210> SEQ ID NO 54
<211> LENGTH: 51
<212> TYPE: DNA
<213> ORGANISM: Artificial Sequence
<220> FEATURE:
<223> OTHER INFORMATION: synthetic DNA sequence; PACpRh02

<400> SEQUENCE: 54
ctctcgggac gaccgccgat aatctcacaa gggcgtatca aagtcgtcc c                 51

<210> SEQ ID NO 55
<211> LENGTH: 51
<212> TYPE: DNA
<213> ORGANISM: Artificial Sequence
<220> FEATURE:
<223> OTHER INFORMATION: synthetic DNA sequence; PACpRh03

<400> SEQUENCE: 55
ctctcgggac gacgggtagg gatgtctaat cccggcggga gctgtcgtcc c                51

<210> SEQ ID NO 56
<211> LENGTH: 51
<212> TYPE: DNA
<213> ORGANISM: Artificial Sequence
<220> FEATURE:
<223> OTHER INFORMATION: synthetic DNA sequence; HPheA104

<400> SEQUENCE: 56
ctctcgggac gaccgcgttt cccaagaaag caagttttgg ttggtcgtcc c                51

<210> SEQ ID NO 57
<211> LENGTH: 51
<212> TYPE: DNA
<213> ORGANISM: Artificial Sequence
<220> FEATURE:
<223> OTHER INFORMATION: synthetic DNA sequence; HTrp03

<400> SEQUENCE: 57
ctctcgggac gaccgcggta gtcttaacct aaagcggtgt caggtcgtcc c                51

<210> SEQ ID NO 58
<211> LENGTH: 23

```
<212> TYPE: DNA
<213> ORGANISM: Artificial Sequence
<220> FEATURE:
<223> OTHER INFORMATION: synthetic DNA sequence; Aptamer against
      Tyrosine-CpRh complex; Short binding form

<400> SEQUENCE: 58
gacggcccga tctcagagta gtc                                              23

<210> SEQ ID NO 59
<211> LENGTH: 38
<212> TYPE: DNA
<213> ORGANISM: Artificial Sequence
<220> FEATURE:
<223> OTHER INFORMATION: synthetic DNA sequence; Tyrosine-CpRh_02

<400> SEQUENCE: 59
tctcgggacg acggcccgaa tgtgtaagta gtcgtccc                              38

<210> SEQ ID NO 60
<211> LENGTH: 39
<212> TYPE: DNA
<213> ORGANISM: Artificial Sequence
<220> FEATURE:
<223> OTHER INFORMATION: synthetic DNA sequence; Tyrosine-CpRh_03

<400> SEQUENCE: 60
tctcgggacg acggcccgat gttccagagt agtcgtccc                             39

<210> SEQ ID NO 61
<211> LENGTH: 42
<212> TYPE: DNA
<213> ORGANISM: Artificial Sequence
<220> FEATURE:
<223> OTHER INFORMATION: synthetic DNA sequence; Tyrosine-CpRh_04

<400> SEQUENCE: 61
tctcgggacg acggcccgat gatgtattcg agtagtcgtc cc                         42

<210> SEQ ID NO 62
<211> LENGTH: 37
<212> TYPE: DNA
<213> ORGANISM: Artificial Sequence
<220> FEATURE:
<223> OTHER INFORMATION: synthetic DNA sequence; Tyrosine-CpRh_05

<400> SEQUENCE: 62
ctcgggacga cggcccgtag atattagtag tcgtccc                               37

<210> SEQ ID NO 63
<211> LENGTH: 38
<212> TYPE: DNA
<213> ORGANISM: Artificial Sequence
<220> FEATURE:
<223> OTHER INFORMATION: synthetic DNA sequence; Tyrosine-CpRh_06

<400> SEQUENCE: 63
tctcgggacg acggcccgca ttaattagta gtcgtccc                              38

<210> SEQ ID NO 64
<211> LENGTH: 36
<212> TYPE: DNA
<213> ORGANISM: Artificial Sequence
<220> FEATURE:
<223> OTHER INFORMATION: synthetic DNA sequence; Tyrosine-CpRh_07

<400> SEQUENCE: 64
```
tctcgggacg acggcccgaa actgagtagt cgtccc                               36

<210> SEQ ID NO 65
<211> LENGTH: 39
<212> TYPE: DNA
<213> ORGANISM: Artificial Sequence
<220> FEATURE:
<223> OTHER INFORMATION: synthetic DNA sequence; Tyrosine-CpRh_08

<400> SEQUENCE: 65
tctcgggacg acggcccgag cactaggagt agtcgtccc                            39

<210> SEQ ID NO 66
<211> LENGTH: 37
<212> TYPE: DNA
<213> ORGANISM: Artificial Sequence
<220> FEATURE:
<223> OTHER INFORMATION: synthetic DNA sequence; Tyrosine-CpRh_09

<400> SEQUENCE: 66
tctcgggacg acgcccgat agtagagtag tcgtccc                               37

<210> SEQ ID NO 67
<211> LENGTH: 40
<212> TYPE: DNA
<213> ORGANISM: Artificial Sequence
<220> FEATURE:
<223> OTHER INFORMATION: synthetic DNA sequence; Tyrosine-CpRh_10

<400> SEQUENCE: 67
ctctcgggac gacggcccga gataatcaag tagtcgtccc                           40

<210> SEQ ID NO 68
<211> LENGTH: 41
<212> TYPE: DNA
<213> ORGANISM: Artificial Sequence
<220> FEATURE:
<223> OTHER INFORMATION: synthetic DNA sequence; Tyrosine-CpRh_11

<400> SEQUENCE: 68
ctctcgggac gacggcccga acatatgtaa gtagtcgtcc c                         41

<210> SEQ ID NO 69
<211> LENGTH: 41
<212> TYPE: DNA
<213> ORGANISM: Artificial Sequence
<220> FEATURE:
<223> OTHER INFORMATION: synthetic DNA sequence; Tyrosine-CpRh_12

<400> SEQUENCE: 69
ctctcgggac gacggcccga tatgtaatta gtagtcgtcc c                         41

<210> SEQ ID NO 70
<211> LENGTH: 51
<212> TYPE: DNA
<213> ORGANISM: Artificial Sequence
<220> FEATURE:
<223> OTHER INFORMATION: synthetic DNA sequence; Tyrosine-CpRh_13

<400> SEQUENCE: 70
ctctcgggac gacggcccga catcatcatc agtatataga gtagtcgtcc c              51

<210> SEQ ID NO 71
<211> LENGTH: 38
<212> TYPE: DNA

<213> ORGANISM: Artificial Sequence
<220> FEATURE:
<223> OTHER INFORMATION: synthetic DNA sequence; Tyr-CpRh (38nt)

<400> SEQUENCE: 71
ctctcgggac gacggcccga tctcagagta gtcgtccc                    38

<210> SEQ ID NO 72
<211> LENGTH: 51
<212> TYPE: DNA
<213> ORGANISM: Artificial Sequence
<220> FEATURE:
<223> OTHER INFORMATION: synthetic DNA sequence; HTyrs07

<400> SEQUENCE: 72
ctctcgggac gaccaagcga gtagtaacac ggcccgacac tgggtcgtcc c     51

<210> SEQ ID NO 73
<211> LENGTH: 51
<212> TYPE: DNA
<213> ORGANISM: Artificial Sequence
<220> FEATURE:
<223> OTHER INFORMATION: synthetic DNA sequence; Cu(II)_Phe01

<400> SEQUENCE: 73
ctctcgggac gacgaggctg gatgcattcg ccggatgttc gatgtcgtcc c     51

<210> SEQ ID NO 74
<211> LENGTH: 51
<212> TYPE: DNA
<213> ORGANISM: Artificial Sequence
<220> FEATURE:
<223> OTHER INFORMATION: synthetic DNA sequence; Cu(II)-Phe10

<400> SEQUENCE: 74
ctctcgggac gacaaggtcc ctttcgtaga tcgaggaagt attgtcgtcc c     51

<210> SEQ ID NO 75
<211> LENGTH: 49
<212> TYPE: DNA
<213> ORGANISM: Artificial Sequence
<220> FEATURE:
<223> OTHER INFORMATION: synthetic DNA sequence; Cu(II)-Phe10_49nt

<400> SEQUENCE: 75
ctctcgggac gacaggtccc tttcgtagat cgaggaagta tgtcgtccc        49

<210> SEQ ID NO 76
<211> LENGTH: 15
<212> TYPE: DNA
<213> ORGANISM: Artificial Sequence
<220> FEATURE:
<223> OTHER INFORMATION: Synthetic DNA Sequence

<400> SEQUENCE: 76
gtcgtcccga gagcc                                             15

<210> SEQ ID NO 77
<211> LENGTH: 35
<212> TYPE: DNA
<213> ORGANISM: Artificial Sequence
<220> FEATURE:
<223> OTHER INFORMATION: Synthetic DNA Sequence
<220> FEATURE:
<221> NAME/KEY: misc_feature
<222> LOCATION: (16)..(27)
<223> OTHER INFORMATION: n is a, c, g, or t

<400> SEQUENCE: 77
ggctctcggg acgacnnnnn nnnnnnngtc gtccc                                35

<210> SEQ ID NO 78
<211> LENGTH: 53
<212> TYPE: DNA
<213> ORGANISM: Artificial Sequence
<220> FEATURE:
<223> OTHER INFORMATION: Synthetic DNA Sequence
<220> FEATURE:
<221> NAME/KEY: misc_feature
<222> LOCATION: (16)..(45)
<223> OTHER INFORMATION: n is a, c, g, or t

<400> SEQUENCE: 78
ggctctcggg acgacnnnnn nnnnnnnnnn nnnnnnnnnn nnnngtcgt ccc              53

<210> SEQ ID NO 79
<211> LENGTH: 54
<212> TYPE: DNA
<213> ORGANISM: Artificial Sequence
<220> FEATURE:
<223> OTHER INFORMATION: Synthetic DNA Sequence

<400> SEQUENCE: 79
ggctctcggg acgacacgct cagccctcct ttcggggca gagtgggtcg tccc             54

<210> SEQ ID NO 80
<211> LENGTH: 13
<212> TYPE: DNA
<213> ORGANISM: Artificial Sequence
<220> FEATURE:
<223> OTHER INFORMATION: Synthetic DNA Sequence

<400> SEQUENCE: 80
gtcgtcccga gag                                                        13

<210> SEQ ID NO 81
<211> LENGTH: 36
<212> TYPE: DNA
<213> ORGANISM: Artificial Sequence
<220> FEATURE:
<223> OTHER INFORMATION: Synthetic DNA Sequence

<400> SEQUENCE: 81
gacgacacgg gcgtcccttc acaaggagag tgagtc                               36

<210> SEQ ID NO 82
<211> LENGTH: 14
<212> TYPE: DNA
<213> ORGANISM: Artificial Sequence
<220> FEATURE:
<223> OTHER INFORMATION: Synthetic DNA Sequence

<400> SEQUENCE: 82
ggtcgtcccg agag                                                       14

<210> SEQ ID NO 83
<211> LENGTH: 51
<212> TYPE: DNA
<213> ORGANISM: Artificial Sequence
<220> FEATURE:
<223> OTHER INFORMATION: Synthetic DNA Sequence

<400> SEQUENCE: 83

```
ctctcgggac gaccacggga tatcttcagg atggtggtaa ctggtcgtcc c        51
```

<210> SEQ ID NO 84
<211> LENGTH: 13
<212> TYPE: DNA
<213> ORGANISM: Artificial Sequence
<220> FEATURE:
<223> OTHER INFORMATION: Synthetic DNA Sequence

<400> SEQUENCE: 84

```
gtcgtcccga gag                                                  13
```

<210> SEQ ID NO 85
<211> LENGTH: 29
<212> TYPE: DNA
<213> ORGANISM: Artificial Sequence
<220> FEATURE:
<223> OTHER INFORMATION: Synthetic DNA Sequence

<400> SEQUENCE: 85

```
gacagccgag ttgattcaac agccgagtc                                 29
```

<210> SEQ ID NO 86
<211> LENGTH: 14
<212> TYPE: DNA
<213> ORGANISM: Artificial Sequence
<220> FEATURE:
<223> OTHER INFORMATION: Synthetic DNA Sequence

<400> SEQUENCE: 86

```
tgtcgtcccg agag                                                 14
```

<210> SEQ ID NO 87
<211> LENGTH: 38
<212> TYPE: DNA
<213> ORGANISM: Artificial Sequence
<220> FEATURE:
<223> OTHER INFORMATION: Synthetic DNA Sequence
<220> FEATURE:
<221> NAME/KEY: misc_feature
<222> LOCATION: (21)..(25)
<223> OTHER INFORMATION: n is a, c, g, or t

<400> SEQUENCE: 87

```
ctctcgggac gacggcccga nnnnngagta gtcgtccc                       38
```

<210> SEQ ID NO 88
<211> LENGTH: 53
<212> TYPE: DNA
<213> ORGANISM: Artificial Sequence
<220> FEATURE:
<223> OTHER INFORMATION: Synthetic DNA Sequence

<400> SEQUENCE: 88

```
ctctcgggac gaccgggtgg gagcgattcg agctactcag gtatggtcgt ccc      53
```

<210> SEQ ID NO 89
<211> LENGTH: 47
<212> TYPE: DNA
<213> ORGANISM: Artificial Sequence
<220> FEATURE:
<223> OTHER INFORMATION: Synthetic DNA Sequence

<400> SEQUENCE: 89

```
ctctcgggac gacggtgtgg atccctcgta gaaggagtag tcgtccc             47
```

APTAMER METHODS AND COMPOSITIONS

CROSS-REFERENCE TO RELATED APPLICATIONS

The present application is a Continuation in Part of International Application No. PCT/US14/29281 filed 14 Mar. 2014, which claims the benefit of U.S. Provisional Application Ser. No. 61/798,079 filed 15 Mar. 2013, each of which is incorporated herein by reference in its entirety.

STATEMENT REGARDING FEDERALLY SPONSORED RESEARCH OR DEVELOPMENT

This invention was made with government support under grants 1033288 and 1026592 awarded by the National Science Foundation and grant GM104960 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

Systematic evolution of ligands by exponential enrichment (SELEX) is a combinatorial technique in molecular biology for producing oligonucleotides of either single-stranded DNA or RNA that specifically bind to a target ligand or ligands. Such conventional procedures can be based on isolating binders from large libraries of random synthetic oligonucleotides. This method can produce strong binding aptamers to a desired ligand, but some ligands (e.g., glucose) have no known aptamers. This may occur because such molecule has no chemically functional groups that will bind the nucleotides. For example, there are no suitable aptamers (e.g., small, practical to synthesize, with high affinity) against sugars such as glucose, fatty acids or related long-chain lipids, or amino acids such as glycine or leucine.

SUMMARY OF THE INVENTION

Provided herein are methods and compositions for determining amino acids in dilute-and-measure assays directly.

Among the various aspects of the present disclosure is the provision of methods and compositions for determining amino acids in dilute-and-measure assays directly from bodily fluids through aptameric sensor/derivatization, complexation, and host-guest complex formation.

One aspect provides a method for isolating an aptamer. In some embodiments, the method includes providing a target molecule; providing a derivatization agent; contacting the target molecule and the derivatization agent to form a target complex; providing an oligonucleotide library comprising a plurality of aptamer candidates; contacting the target complex and the oligonucleotide library; and isolating an aptamer that binds to the target complex.

In some embodiments, isolating the aptamer that binds to the target complex comprises removal of aptamer candidates that do not bind to the target complex. In some embodiments, the method includes eluting the aptamer from the bound target complex under increasing stringency, and isolating an eluted aptamer having high affinity for the target complex. In some embodiments, the method includes systematic evolution of ligands by exponential enrichment (SELEX).

In some embodiments, the aptamer does not substantially bind the non-complexed target molecule. In some embodiments, the aptamer does not substantially bind the non-complexed derivatization agent. In some embodiments, the method includes counter-selecting an aptamer against the derivatization agent alone or against the target molecule alone.

In some embodiments, the oligonucleotide library includes randomly generated oligonucleotide sequences of a fixed length flanked by a constant 5' end and a constant 3' end, the constant 5' end and the constant 3' end functioning as a primer.

In some embodiments, the aptamer is a DNA, RNA, or XNA molecule. In some embodiments, the aptamer comprises at least about 15 oligonucleotides up to about 100 oligonucleotides. In some embodiments, the aptamer has an equilibrium constant (Kd) of about 1 pM up to about 10.0 µM; about 1 pM up to about 1.0 µM; about 1 pM up to about 100 nM; about 100 pM up to about 10.0 µM; about 100 pM up to about 1.0 µM; about 100 pM up to about 100 nM; or about 1.0 nM up to about 10.0 µM; about 1.0 nM up to about 1.0 µM; about 1 nM up to about 200 nM; about 1.0 nM up to about 100 nM; about 500 nM up to about 10.0 µM; or about 500 nM up to about 1.0 µM.

In some embodiments, the target molecule comprises a small molecule, a protein, or a nucleic acid. In some embodiments, the target molecule comprises a small molecule selected from the group consisting of a carbohydrate molecule, a fatty acid molecule, a steroid molecule, an amino acid, a lead-like small molecule, a drug-like small molecule, and a derivative or a combination thereof. In some embodiments, the target molecule comprises a carbohydrate molecule selected from the group consisting of glucose, dextrose, fructose, galactose, sucrose, maltose, lactose, polyol, polyhydric alcohol, polyalcohol, glycitol, methanol, glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol.

In some embodiments, the target molecule comprises a fatty acid molecule selected from the group consisting of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, and docosahexaenoic acid, or derivatives thereof. In some embodiments, the target molecule comprises a steroid molecule selected from the group consisting of a cholestane, a cholane, a pregnane, an androstane, a gonane, an estrane, cholesterol, estradiol, testosterone, progesterone, medrogestone, β-sitosterol, and dexamethasone. In some embodiment, the target molecule comprises a sphingolipid, such as sphinganine, sphingosine, phosphorylated sphingosine (e.g., sphingosine-1-phosphate), or methylated sphingosine, or a ceramide or sphingomyelin or ganglioside or phosphosphingolipid.

In some embodiments, the target molecule comprises an amino acid selected from the group consisting of histidine, isoleucine, leucine, lysine, methionine, phenylalanine, threonine, tryptophan, valine, alanine, arginine, asparagine, aspartic acid, cysteine, glutamic acid, glutamine, glycine, proline, serine, tyrosine, selenocysteine, pyrrolysine, lanthionine, 2-aminoisobutyric acid, dehydroalanine, N-formylmethionine, gamma-amino-butyric acid (GABA), hydroxyproline, carnitine, ornithine, S-adenosylmethionine, citrulline, beta alanine (3-aminopropanoic acid), canavanine, mimosine, aspartame, 5-hydroxytryptophan, L-dihydroxyphenylalanine, and eflornithine.

In some embodiments, the derivatization agent comprises a metal ion complex, a cyclic oligosaccharide, a boronic acid, or a resorcinol cyclic tetramer. In some embodiments, the target molecule comprises an amino acid and the derivatization agent comprises a metal ion complex. In some embodiments, the target molecule comprises a fatty acid, a steroid, a hydrophobic lead-like compound, or a hydrophobic drug-like compound and the derivatization agent comprises a cyclic oligosaccharide. In some embodiments, the target molecule comprises a carbohydrate and the derivatization agent comprises a boronic acid.

In some embodiments, the derivatization agent comprises Cp*Rh(III) or a metal ion complex selected from Ni(II), Cu(II), Zn(II), or Co(III) bound to a bidentate, tridentate, or tetradentate ligand. In some embodiments, the derivatization agent comprises a cyclic oligosaccharide, the cyclic oligosaccharide comprising a cyclodextrin derivative. In some embodiments, the derivatization agent comprises a boronic acid, the boronic acid comprising a bis-boronic acid, an aromatic boronic acid, an amino boronic acid, or an aromatic amino boronic acid.

In some embodiments, the method includes isolating an aptamer that binds to the target complex and has a nucleic acid sequence comprising one or more unpaired nucleic acid bases when the aptamer is folded into a double stranded configuration, wherein the one or more unpaired nucleic acid bases form a binding pocket such that the aptamer can bind the derivatization agent and the target molecule.

Another aspect provides an aptamer. In some embodiments, the aptamer has a nucleic acid sequence that includes SEQ ID NO: 3; SEQ ID NO: 4 (Glucose-BA_01); SEQ ID NO: 5 (Glucose-BA_07); SEQ ID NO: 6 (Glucose-BA_08); SEQ ID NO: 7 (Glucose-BA_09); SEQ ID NO: 8 (Glucose-BA_10); SEQ ID NO: 9 (Glucose-BA_11); SEQ ID NO: 10 (Glucose-BA_12); SEQ ID NO: 11 (Glucose-BA_13); SEQ ID NO: 12 (Glucose-BA_14); SEQ ID NO: 13 (Glucose-BA_15); SEQ ID NO: 14 (Glucose-BA_16); SEQ ID NO: 15 (Glucose-BA_17); SEQ ID NO: 16 (GLUBA02); SEQ ID NO: 17 (GLUBA09); SEQ ID NO: 18 (GLUBA09_M1); SEQ ID NO: 19 (GLUBA17); SEQ ID NO: 20 (GLUBAN3W10); SEQ ID NO: 21 (GLUBAN3W11); or SEQ ID NO: 22 (GLUBAN3W19), or a sequence at least 80% (e.g., at least 85%, 90%, 95%, 99%) identical thereto and binding glucose complexed with a bis-boronic derivatization agent.

In some embodiments, the aptamer has a nucleic acid sequence that includes SEQ ID NO: 23 (FrucBA02); SEQ ID NO: 24 (FrucBA02_M1); or SEQ ID NO: 25 (FrucBA05), or a sequence at least 80% (e.g., at least 85%, 90%, 95%, 99%) identical thereto and binding fructose complexed with a bis-boronic derivatization agent.

In some embodiments, the aptamer has a nucleic acid sequence that includes SEQ ID NO: 26 (GalacBA05); SEQ ID NO: 27 (GalacBA01); or SEQ ID NO: 28 (GalacBA06), or a sequence at least 80% (e.g., at least 85%, 90%, 95%, 99%) identical thereto and binding galactose complexed with a bis-boronic derivatization agent.

In some embodiments, the aptamer has a nucleic acid sequence that includes SEQ ID NO: 29 (BAOnly01); or SEQ ID NO: 30 (BAOnly03), or a sequence at least 80% (e.g., at least 85%, 90%, 95%, 99%) identical thereto and binding boronic acid.

In some embodiments, the aptamer has a nucleic acid sequence that includes SEQ ID NO: 31; SEQ ID NO: 32 (Arginine-Cp*Rh_02); SEQ ID NO: 33 (Arginine-Cp*Rh_03); SEQ ID NO: 34 (Arginine-Cp*Rh_04); SEQ ID NO: 35 (Arginine-Cp*Rh_05); or SEQ ID NO: 36 (ARG01_Cp), or a sequence at least 80% (e.g., at least 85%, 90%, 95%, 99%) identical thereto and binding arginine complexed with a Cp*Rh(III) derivatization agent.

In some embodiments, the aptamer has a nucleic acid sequence that includes SEQ ID NO: 37 (AspaCp01); SEQ ID NO: 38 (AspaCp03); or SEQ ID NO: 39 (AspaCp04), or a sequence at least 80% (e.g., at least 85%, 90%, 95%, 99%) identical thereto and binding asparagine complexed with a Cp*Rh(III) derivatization agent.

In some embodiments, the aptamer has a nucleic acid sequence that includes SEQ ID NO: 40 (CIT30N02_Cp*Rh), or a sequence at least 80% (e.g., at least 85%, 90%, 95%, 99%) identical thereto and binding citrulline complexed with a Cp*Rh(III) derivatization agent.

In some embodiments, the aptamer has a nucleic acid sequence that includes SEQ ID NO: 41 (GlutaCp02); or SEQ ID NO: 42 (GlutaCp15), or a sequence at least 80% (e.g., at least 85%, 90%, 95%, 99%) identical thereto and binding glutamine complexed with a Cp*Rh(III) derivatization agent.

In some embodiments, the aptamer has a nucleic acid sequence that includes SEQ ID NO: 43; SEQ ID NO: 44 (Glycine-Cp*Rh_01); SEQ ID NO: 45 (Gly-Cp); SEQ ID NO: 46 (Gly-Cp+1 bp); or SEQ ID NO: 47 (GLYHW-Cp*Rh06), or a sequence at least 80% (e.g., at least 85%, 90%, 95%, 99%) identical thereto and binding glycine complexed with a Cp*Rh(III) derivatization agent.

In some embodiments, the aptamer has a nucleic acid sequence that includes SEQ ID NO: 48 (LeuCp01); SEQ ID NO: 49 (LeuCp04); or SEQ ID NO: 50 (LeuCp17), or a sequence at least 80% (e.g., at least 85%, 90%, 95%, 99%) identical thereto and binding leucine complexed with a Cp*Rh(III) derivatization agent.

In some embodiments, the aptamer has a nucleic acid sequence that includes SEQ ID NO: 51 (LysCp05); or SEQ ID NO: 52 (LysCp*Rh18), or a sequence at least 80% (e.g., at least 85%, 90%, 95%, 99%) identical thereto and binding lysine complexed with a Cp*Rh(III) derivatization agent In some embodiments, the aptamer has a nucleic acid sequence that includes SEQ ID NO: 53 (PACp*Rh01); SEQ ID NO: 54 (PACp*Rh02); SEQ ID NO: 55 (PACp*Rh03); or SEQ ID NO: 56 (HPheAl04), or a sequence at least 80% (e.g., at least 85%, 90%, 95%, 99%) identical thereto and binding phenylalanine complexed with a Cp*Rh(III) derivatization agent In some embodiments, the aptamer has a nucleic acid sequence that includes SEQ ID NO: 73 (Cu(II)_Phe01); SEQ ID NO: 74 (Cu(II)-Phe10); or SEQ ID NO: 75 (Cu(II)-Phe10_49 nt), or a sequence at least 80% (e.g., at least 85%, 90%, 95%, 99%) identical thereto and binding phenylalanine complexed with a Cu(II) derivatization agent.

In some embodiments, the aptamer has a nucleic acid sequence that includes SEQ ID NO: 57 (HTrp03), or a sequence at least 80% (e.g., at least 85%, 90%, 95%, 99%) identical thereto and binding tryptophan complexed with a Cp*Rh(III) derivatization agent;

In some embodiments, the aptamer has a nucleic acid sequence that includes SEQ ID NO: 57 (HTrp03), or a sequence at least 80% (e.g., at least 85%, 90%, 95%, 99%)

identical thereto and binding tryptophan complexed with a Cp*Rh(III) derivatization agent; or In some embodiments, the aptamer has a nucleic acid sequence that includes SEQ ID NO: 58; SEQ ID NO: 59 (Tyrosine-Cp*Rh_02); SEQ ID NO: 60 (Tyrosine-Cp*Rh_03); SEQ ID NO: 61 (Tyrosine-Cp*Rh_04); SEQ ID NO: 62 (Tyrosine-Cp*Rh_05); SEQ ID NO: 63 (Tyrosine-Cp*Rh_06); SEQ ID NO: 64 (Tyrosine-Cp*Rh_07); SEQ ID NO: 65 (Tyrosine-Cp*Rh_08); SEQ ID NO: 66 (Tyrosine-Cp*Rh_09); SEQ ID NO: 67 (Tyrosine-Cp*Rh_10); SEQ ID NO: 68 (Tyrosine-Cp*Rh_11); SEQ ID NO: 69 (Tyrosine-Cp*Rh_12); SEQ ID NO: 70 (Tyrosine-Cp*Rh_13); SEQ ID NO: 71 (Tyr-Cp*Rh (38nt)); or SEQ ID NO: 72 (HTyrs07), or a sequence at least 80% (e.g., at least 85%, 90%, 95%, 99%) identical thereto and binding tyrosine complexed with a Cp*Rh(III) derivatization agent.

In some embodiments, the aptamer has a nucleic acid sequence that includes one or more unpaired nucleic acid bases when the aptamer is folded into a double stranded configuration. In some embodiments, the one or more unpaired nucleic acid bases form a binding pocket such that the aptamer can bind a derivatization agent and a target molecule. In some embodiments, the aptamer has a nucleic acid sequence that includes SEQ ID NO: 71 (Tyr-Cp*Rh (38nt)); SEQ ID NO: 53 (PACp*Rh01); SEQ ID NO: 40 (CIT30N02_Cp*Rh); SEQ ID NO: 41 (GlutaCp02); SEQ ID NO: 52 (LysCp*Rh18); SEQ ID NO: 51 (LysCp05); SEQ ID NO: 75 (Cu(II)-Phe10_49 nt); SEQ ID NO: 36 (ARG01_Cp); SEQ ID NO: 57 (HTrp03 aptamer); SEQ ID NO: 45 (Gly-Cp); SEQ ID NO: 38 (AspaCp03); SEQ ID NO: 47 (GLYHW-Cp*Rh06); SEQ ID NO: 50 (LeuCp17); SEQ ID NO: 53 (PACp*Rh01); SEQ ID NO: 73 (Cu(II)_Phe01); or SEQ ID NO: 56 (HPheAl04); or a sequence at least 80% (e.g., at least 85%, 90%, 95%, 99%) identical thereto and binding the target molecule complexed with the derivatization agent.

Another aspect provides a method of detecting a target molecule in a sample. In some embodiments, the method includes (a) providing a sample; (b) contacting the biological sample and a derivatization agent to form a target complex comprising the derivatization agent and a target molecule when the target molecule is present in the sample; (c) contacting the biological sample and (i) an aptamer selected according to methods described above or (ii) an aptamer described above to form an aptamer target complex when the target complex is present in the sample; and (d) detecting the aptamer target complex when present in the sample.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 3A is a chemical structure of tyrosine. FIG. 3B is an illustration of a motif isolated that binds to Cp*Rh(III)*Tyr, with conserved bases in bold. FIG. 3C is an illustration of the structure of sensors (where F represents fluorescein and D represents dabcyl) used to obtain results in FIG. 3D-F. FIG. 3D is a line and scatter plot of a sensor responding to concentrations of tyrosine in the presence of Cp*Rh(III) at constant 10 µM concentration. FIG. 3E is a line and scatter plot showing a sensor is selective for tyrosine over various other amino acids in the presence of 50 µM Cp*Rh(III) and aptamer sensors. FIG. 3F is a line and scatter plot of the sensor in serially diluted 1 mM tyrosine solution (blue), serum spiked with 1 mM tyrosine, then diluted (red), and healthy, fasting subject serum (black). A 10 µM concentration of Cp*Rh(III) was added to all samples to derivatize all bi- and tri-dentate ligands. At certain dilutions the difference between spiked and non-spiked serums were observed, despite presence of all interferences. The data shows that tyrosine can be detected in a dilute-and-measure assay.

FIG. 4A is a chemical structure of arginine. FIG. 4B is an illustration of a motif isolated that binds to Cp*Rh(III)*Arg, with conserved bases in bold. FIG. 4C is an illustration of the structure of sensors (where F represents fluorescein and D represents dabcyl) used to obtain results in FIG. 4D-F. FIG. 4D is a line and scatter plot of a sensor responding to concentrations of arginine in the presence of Cp*Rh(III) at constant 50 µM concentration. FIG. 4E is a line and scatter plot showing a sensor is selective for arginine over various other amino acids in the presence of 50 µM Cp(Rh(III)) and aptameric sensor. FIG. 4F is a line and scatter plot of the sensor in serially diluted 1 mM arginine solution (blue), serum spiked with 1 mM arginine, then diluted (red), and healthy, fasting subject serum (black). A 10 µM concentration of Cp*Rh(III) was added to all samples to derivatize all bi- and tri-dentate ligands. At certain dilutions the difference between spiked and non-spiked serums were observed, despite presence of all interferences. The data shows that arginine can be detected in a dilute-and-measure assay at clinically relevant concentrations. FIG. 4G shows a motif isolated that binds to Cp*Rh(III)*Phe with Kd of about 60 nm. FIG. 4H shows a motif that binds Phe (i.e., without cofactor) with Kd of about 6 µM. FIG. 4I shows RFU as a function of amino acid (Phe, Trp, Tyr) concentration for the motif of FIG. 4G. FIG. 4J shows RFU as a function of amino acid (Phe) concentration for the motif of FIG. 4H.

FIG. 7A shows a metal complex/ion binding motif for an aptamer that binds nucleic acids. FIG. 7B shows SEQ ID NO:87, which is the Tyr selective aptamer Tyr-Cp*Rh (38nt) (SEQ ID NO: 71), where NNNNN is replaced with TCTCA FIG. 7C shows Phe cross-reactive Trp aptamer PACp*Rh01 (SEQ ID NO: 53). FIG. 7D shows citrulline non-selective aptamer CIT30N02_Cp*Rh (SEQ ID NO: 40). FIG. 7E shows Gln selective aptamer GlutaCp02 (SEQ ID NO: 41). FIG. 7F shows Lys non-selective aptamer LysCp*Rh18 (SEQ ID NO: 88). FIG. 7G shows Lys selective aptamer LysCp05 (SEQ ID NO: 89). FIG. 7H shows Phe cross-reactive Trp aptamer Cu(II)-Phe10_49nt (SEQ ID NO: 75).

FIG. 8A shows the binding motif for a plurality of unpaired bases. FIG. 8B shows Arg selective ARG01_Cp aptamer (SEQ ID NO: 36). FIG. 8C shows Trp selective HTrp03 aptamer (SEQ ID NO: 57).

FIG. 9A shows Gly selective aptamer Gly-Cp sensor (SEQ ID NO: 46). FIG. 9B shows Asn selective aptamer AspaCp03 (SEQ ID NO: 38). FIG. 9C shows Gly non-specific aptamer GLYHW-Cp*Rh06 (SEQ ID NO: 47).

FIG. 11A depicts the structure of an aptamer reactive for Phe and cross-reactive for Trp. FIG. 11B is a scatter and line plot showing aptamer detected Phe concentration (µM) as a function of time (hr) in serum samples from capillary blood of a female subject (TPW) and a male subject (MNS) having an oral load of 100 mg/kg at time zero.

FIG. 12A shows Cu(II)_Phe01 aptamer (SEQ ID NO: 73) reactive for Phe. FIG. 12B shows a scatter and line plot for RFU as a function of amino acid concentration (µM) for phenylanine, tyrosine, tryptophan, and glycine using the aptamer of FIG. 12A, where Phe specificity is demonstrated. FIG. 12C shows HPheAl04 aptamer (SEQ ID NO: 56) reactive for Phe. FIG. 12D shows a scatter and line plot for RFU as a function of amino acid concentration (µM) for phenylanine, tryptophan, and tyrosine, using the aptamer of FIG. 12C, where Phe specificity is demonstrated.

DETAILED DESCRIPTION OF THE INVENTION

Figure 1A:
FIG. 1A is an illustration of a generic scheme of complexation between a receptor (e.g., organometallic or synthetic receptor) and its target (e.g., small molecules target).

The present disclosure is based, at least in part, on the discovery of aptamers against boronic acid-sugar complexes and amino acid-Cp*Rh(III) complexes. Described herein is in situ derivatization SELEX for isolation of high-affinity and high-specificity, low complexity aptameric sensors (see Examples). Thus is provided an ability to detect in solution-phase difficult to measure analytes.

According to approaches described herein, one can perform in situ derivatization of challenging targets with known organic receptors (e.g., a metal ion complex, such as Cp*Rh (III), for amino acids; cyclodextrin derivatives for fatty acids; boronic acids for glucose or other sugars) and perform selection that can target specifically complexes with these receptors, yielding high-affinity aptamers.

For example, a mixture of nucleic acid molecules (e.g., candidate aptamers, such as a library of DNA molecules) are allowed to bind a target molecule (e.g., a protein, peptide, or small molecule displaying nucleophilic groups) in the presence of a derivatization agent, such as an organometallic reagent (e.g., modified Cp*Rh or Pt complexes), where the derivatization agent binds both a nucleic acid molecule and the target molecule. Tight multicomponent complexes can be isolated and amplified through standard protocols (e.g., SELEX). The identified aptamer can be useful as a tightly binding analytical reagent.

Accordingly, both derivatization agents or targets themselves can be selected against during selection of the complex. These procedures can yield aptamers against challenging targets where conventional approaches would likely fail.

Conventional approaches, such as systematic evolution of ligands by exponential enrichment (SELEX), are not always effective against challenging targets having no chemically functional groups that will bind nucleotides. The present disclosure can provide for functional aptamers for challenging targets. Aptamers selected according to the present disclosure can be obtained by complexing in situ a target ligand with various metal ions, sugars, or acids. Such an approach allows for successful production of aptamers for challenging targets, e.g., glucose or amino acids, as described herein. Compositions and methods described herein can be useful, for example, in clinical chemistry or for control of nucleic acid-based nanostructures.

In some embodiments, a nucleic acid molecule (e.g., DNA) in the presence of organometallic compound is coordinated by metal, while organic components stick out. If a library of DNA molecules is present, members will form many complexes in equilibrium. Organic components of organometallic complex, remaining valences (coordination sites) on metal, and nucleic acid molecule (e.g., DNA) all can then form a complex with target. Such a complex can be isolated in conventional ways (e.g., traditional or solution-phase SELEX). A result can be a nucleic acid aptamer (e.g., DNA) that is enhanced in binding by organometallic components. Two or more organometallic components can bind in an aptamer, and many different complexes can be used at the same time in mixtures.

Aptamers, or oligonucleotide-based receptors as described herein, provide unique advantages as analytical tools. For example, an aptamer can be incorporated in simple and rapid mix-and-measure assays or readily attached to a surface e.g., suitable for integration in biosensors.

The present disclosure provides the ability to determine amino acids in dilute-and-measure assay directly from bodily fluids through aptameric sensor/in-situ derivatization protocol. Some embodiments provide methods for determination of amino acids or other bi- and tri-dentate analytes in dilute-and-measure assays using in situ derivatization with organometallic reagents and aptameric sensors specific for particular derivatives. Prior to the present disclosure, there was thought to be no generally available and easy to use specific, quantitatively suitable assay. Conventionally, amino acids were determined in complex multi-step procedures requiring specialized instrumentation. The present disclosure can overcome these limitations and others, such as interferences, associated with conventional approaches.

Approaches described herein can introduce complexity to a target molecule and specifically target the resulting derivatized target to select a small to medium aptamer; as opposed to selecting a large, complex aptamer against a simple target or pre-incorporating (i.e., co-opting) a cofactor (e.g., an organic receptor) inside the aptamer (which may not yield increase, and would likely lead to a decrease, of sensitivity of original receptor because binding of aptamer to receptor might compete with binding of ligand to receptor).

Derivatization Agent

As described herein, a derivatization agent can be combined with a target molecule to form in situ a complex capable of binding an aptamer. In some embodiments, an aptamer can bind two or more derivatization agents (see e.g., FIG. 1F). In some embodiments, two or more derivatization agents and resulting complexes can be included in a mixture. The complex can be stable or in equilibrium with free derivatization agent and target analyte.

A derivatization agent can be a metallic, organic, or an organometallic receptor. For example, a derivatization agent can be a metal ion, metal ion complex, a cyclic oligosaccharide, or a boronic acid.

Metal ion or metal ion complex.

A derivatization agent can include a metal ion or metal ion complex. A metal ion or metal ion complex derivatization agent can be complexed with an amino acid to select an aptamer thereto. For example, a metal ion complex derivatization agent (e.g., Cp*Rh(III)) can be complexed with glycine to select an aptamer thereto. As another example, a metal ion complex derivatization agent (e.g., Cp*Rh(III)) can be complexed with tyrosine to select an aptamer thereto. As another example, a metal ion derivatization agent (e.g., Cu(II)) can be complexed with phenylalanine to select an aptamer thereto.

For example, a derivatization agent can include or be Ni(II), Cu(II), Zn(II), Co(III), Pt or most any other metal, optionally with a bidentate, tridentate, or tetradentate ligand binding to it (e.g., Co(II) with tetradentate ligand) (see generally, Chin et al. 1999 Nature 401(6750), 254-257; Job et al. 1974 J. Am. Chem. Soc. 96, 809-819; Yamaguchi et al. 1980 Inorg. Chem. 19, 2010-2016; Fenton et al. 1995 Inorg. Chim. Acta 236, 109-115; Greenstein et al. 1996 Chemistry of the Amino Acids Vol. 1, 594, Wiley and Sons, New York). For example, a derivatization agent can be Ni(II), Cu(II), Zn(II), Co(III), or most any other metal, with a bidentate, tridentate, or tetradentate ligand binding to it. As another example, a metal ion derivatization agent can be Cu(II). As another example, a derivatization agent can include a metal ion complex comprising an alkali metal (e.g., lithium, sodium, potassium, rubidium, cesium, or francium), an alkaline earth metal (e.g., beryllium, magnesium, calcium, strontium, barium, or radium), a transition metal (e.g., zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum, gold, mercury, rutherfordium, dubnium, seaborgium, bohrium, hassium, or copernicium), a post-transition metal (e.g., aluminum, gallium, indium, tin, thallium, lead, bismuth, or polonium), a lanthanide metal (e.g., lanthanum, cerium, praseodymium, neodymium, promethium, samarium, europium, gadolinium, terbium, dysprosium, holmium, erbium, thulium, ytterbium, or lutetium), an actinide metal (e.g., actinium, thorium, protactinium, uranium, neptunium, plutonium, americium, curium, berkelium, californium, einsteinium, fermium, mendelevium, nobelium, or lawrencium), or another type of metal (e.g., meitnerium, darmstadtium, roentgenium, ununtrium, flerovium, ununpentium, livermorium, germanium, arsenic, antimony, or astatine). The metal ion can be bound to a bidentate, tridentate, or tetradentate ligand to form a derivatization agent. Ligands suitable for binding a metal are known in the art. An exemplary ligand is a cyclopentadienyl or a pentamethylcyclopentadienyl.

Organic or Organometallic Component.

A derivatization agent can include an organic or organometallic component. The metal ion can be bound to a bidentate, tridentate, or tetradentate ligand to form a derivatization agent. Ligands suitable for binding a metal are known in the art. An exemplary ligand is a cyclopentadienyl (Cp) or a pentamethylcyclopentadienyl (Cp*). The pentamethylcyclopentadienyl ligand (Cp*) is a ligand in organometallic compounds arising from the binding of the five ring-carbon atoms in $C_5Me_5\text{-}$, or Cp*-, to metals.

For example, a metal ion complex derivatization agent can be Cp*-X, where X is a metal (e.g., Rh). For example, a metal ion complex derivatization agent can be Cp*Rh(III) (see e.g., Example 2; Example 3).

As another example, a metal ion complex derivatization agent can be Cp-X, where X is a metal and CP is cyclopentadienyl or a Cp derivative.

As another example, a metal ion complex derivatization agent can be an Fp2 or Fp2-X (e.g., where Fp2 is a fip dimer, cyclopentadienyliron dicarbonyl dimer, $Cp_2Fe_2(CO)_4$).

Linker.

A derivatization agent can have a linker between the metal ion and the organic component. A linker can be, for example, an organic molecule with at least one end having a functional group. Various linker groups are known in the art; except as otherwise specified, compositions described herein can include state of the art linker groups. For example, a state of the art linker molecule can be any such molecule capable of coupling a metal ion and an organic component. A linker group can include one or more of the following exemplary functional groups: carboxylic acid or carboxylate groups (e.g., Fmoc-protected-2,3-diaminopropanoic acid, ascorbic acid), silane linkers (e.g., aminopropyltrimethoxysilane (APTMS)), or dopamine. A linker group, such as carboxylic acid, dopamine, or silane (or another state of the art linker group), can provide missing coordination sites (e.g., two oxygen coordination sites) for binding. Exemplary linking groups include, but are not limited to, carboxylic acid or carboxylate groups, Fmoc-protected-2,3-diaminopropanoic acid, ascorbic acid, silane linkers, aminopropyltrimethoxysilane (APTMS), or dopamine. Other linkers can include alkane, alkene, or alkyne linkers of various size (e.g., n=2, 3, 4, 5, 6, 7, 8, 9, or 10, or more). A linker can include chemical motifs such as disulfides, hydrazones, or peptides (e.g., cleavable), or thioethers (e.g., noncleavable). A linker can include maleimide, or sulfhydryl reactive groups, or succinimidyl esters.

For example, a metal ion complex derivatization agent can be Cp*-CH$_{2(n)}$X, where X is a metal (e.g., a metal described above) and n is at least 1 (e.g., 2, 3, 4, 5, 6, 7, 8, 9, 10, or more). —CH$_2$ linkers of various lengths can be used. As another example, a metal ion complex derivatization agent can be Cp*-CH$_2$CH$_2$X, where X is a metal (e.g., a metal described above).

Cyclic Oligosaccharide.

A derivatization agent can be a cyclic oligosaccharide. A derivatization agent can be a cyclodextrin or cyclodextrin derivative. A derivatization agent can be a cyclic oligosaccharide with hydrophobic cavities. For example, a derivatization agent can be an α-cyclodextrin (i.e., a six-membered sugar ring molecule), a β-cyclodextrin (i.e., a seven-membered sugar ring molecule), or a γ-cyclodextrin (i.e., an eight-membered sugar ring molecule), or a derivative thereof. A derivatization agent can be a cyclodextrin derivative. For example, a derivatization agent can be an α-cyclodextrin, a β-cyclodextrin, or a γ-cyclodextrin having on either or both rims one or hydroxyl groups derivatized with other groups. Availability of multiple reactive hydroxyl groups can be used to increase functionality of a cyclodextrin by substituting them (i.e., derivatizing them).

A cyclodextrin or cyclodextrin derivative can have at least 5 glucopyranoside (e.g., α-D-glucopyranoside) units linked 1, 4. For example, a cyclodextrin or cyclodextrin derivative can have 5, 6, 7, 8, 9, 10, 11, 12, 13, 14, 15, 16, 17, 18, 19, 20, 21, 22, 23, 24, 25, 26, 27, 28, 29, 30, 31, 32, or more, glucopyranoside units.

A derivatization agent can be a cyclodextrin derivative. A cyclodextrin derivative can be, for example, an α-cyclodextrin, a β-cyclodextrin, or a γ-cyclodextrin. For example, a derivatization agent can be an α-cyclodextrin, a β-cyclodextrin, or a γ-cyclodextrin having on either or both rims one or hydroxyl groups displayed. Availability of multiple reactive hydroxyl groups can increase functionality of a cyclodextrin. Functional groups used to derivatize hydroxyl groups can contain basic groups, such as imidazoles, pyridines, metal ion complexes, acidic groups, such as carboxylic acids, sulfates, or photoreactive groups. A cyclic oligosaccharide derivatization agent can be complexed with, for example, a fatty acid, steroid, or hydrophobic drug to select an aptamer thereto. In some embodiments, a cyclic oligosaccharide derivatization agent can be complexed with a fatty acid to select an aptamer thereto.

Organoborane.

A derivatization agent can be an organoborane. A derivatization agent can be a boronic acid. A boronic acid is understood to be an alkyl or aryl substituted boric acid containing a carbon-boron bond and is understood to belong to the larger class of organoboranes. In some embodiments, a boronic acid can form reversible covalent complexes with molecules such as sugars, amino acids, hydroxamic acids, etc., or molecules with Lewis base donor functional groups such as alcohol, amine, or carboxylate. The chemistry involved in binding a boronic acid to a target molecule, such as a saccharide, is understood in the art and can be adapted accordingly for use described herein (see generally, Fang et al. 2004 J Fluorescence 14(5), 481-489).

Exemplary boronic acids suitable as a derivatization agent include, but are not limited to an aromatic boronic acid or amino boronic acid. An aromatic boronic acid can includes phenyl, naphty, anthrylboronic acids, pyrenyl, or any other aromatic group. A boronic acid or an aromatic boronic acid can further include an amino group. For example, an aromatic boronic acid can have an amino group is positioned in a 1,5-relationship with the boronic acid.

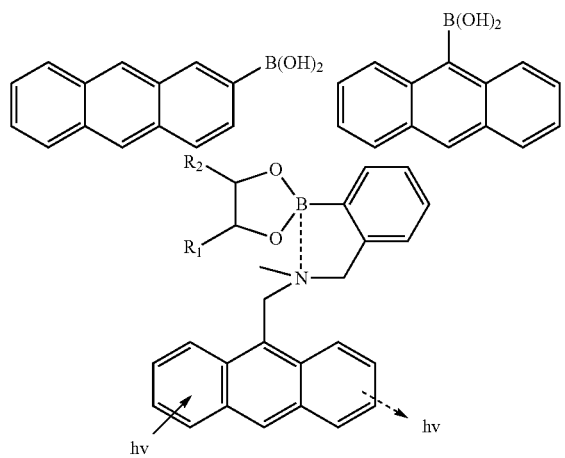

A derivatization agent comprising a boronic acid can include more than one boronic acid group or an aromatic boronic acid can include more than one boronic acid group or more than one aromatic group. For example, two aromatic acids can be connected via a linker or boronic, e.g., as depicted below.

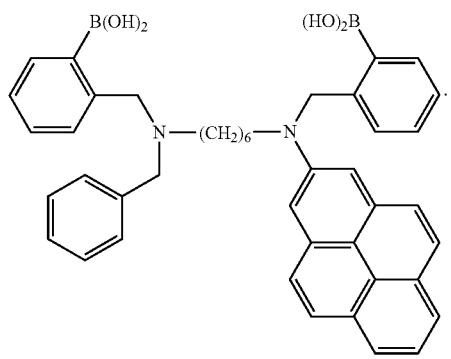

An exemplary boronic acid derivatization agent can be:

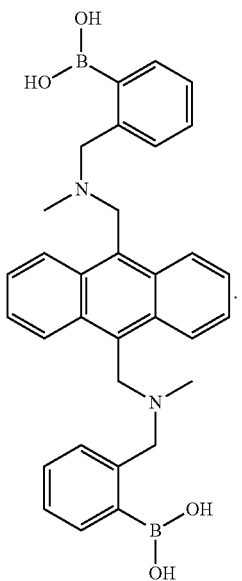 [SMILES: CN(Cc1ccccc1B(O)O)Cc1c2ccccc2c(CN(C)Cc2ccccc2B(O)O)c2ccccc12]

The above exemplary boronic acid derivatization agent can interact with a sugar, such as glucose, as follows:

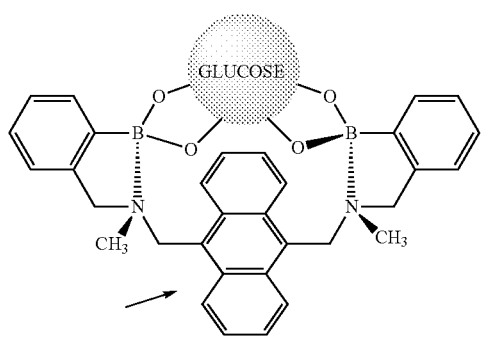

As described herein, a boronic acid derivatization agent can be complexed with a sugar to select an aptamer thereto. For example, a boronic acid derivatization agent can be complexed with glucose to select an aptamer thereto. As another example, a bis-boronic receptor can be a derivatization agent complexed with glucose to select an aptamer thereto (see e.g., Example 4, FIG. 5).

Target Molecule

As disclosed herein, a target molecule can be combined with a derivatization agent to form a complex, and an aptamer can be raised against such complex. A target molecule can be, for example, a small molecule, a protein, or a nucleic acid, or structures or compositions containing any of these. For example, a target molecule can be a protein, peptide, or small molecule displaying one or more nucleophilic groups. As another example, a target molecule can be a small molecule selected from a carbohydrate molecule, a fatty acid molecule, an amino acid, or a derivative or a combination thereof.

A target molecule can occur in solution or attached to a substrate. For example, a target molecule can be a sugar molecule on the surface of a cell.

Amino Acid Target Molecule.

A target molecule can be an amino acid or an analog or derivative thereof. Shown herein is analysis of specific amino acids (e.g., tyrosine and arginine) by in situ derivatization with Cp*Rh(III) and an aptamer measuring the complex formation (see e.g., Example 2; Example 3). For example, an amino acid target molecule can be complexed with a metal ion derivatization agent (e.g., Cp*Rh(III)) and an aptamer can be selected against such complex. Results showed an unexpected extremely high affinity selection. Such high affinity is sufficient for serum analysis and demonstrates a novel and unexpected dilute-and-measure assay of amino acids.

An amino acid is understood as an organic compound having amine (—$NH_2$) and carboxylic acid (—COOH) functional groups, along with a side-chain specific to each amino acid. A target molecule can be any of the about 500 known amino acids (see generally, W et al. 1983 Chem. Int. Ed. Engl. 22(22), 816-828). A target molecule can be an alpha- (α-), beta- (β-), gamma- (γ-) or delta- (δ-) amino acid. A target molecule can be an aliphatic, acyclic, aromatic, hydroxyl-containing, or sulfur-containing amino acid. An amino acid analog or derivative can be, for example, an amino alcohol or an aminophosphonic acid.

A target molecule can be a proteinogenic amino acid. For example, a target molecule can be an amino acid selected from histidine, isoleucine, leucine, lysine, methionine, phenylalanine, threonine, tryptophan, valine, alanine, arginine, asparagine, aspartic acid, cysteine, glutamic acid, glutamine, glycine, proline, serine, tyrosine, selenocysteine, or pyrrolysine. As another example, a target molecule can be tyrosine (see e.g., Example 2). As another example, a target molecule can be arginine (see e.g., Example 3).

A target molecule can be an essential amino acid, such as histidine, isoleucine, leucine, lysine, methionine, phenylalanine, threonine, tryptophan, or valine.

A target molecule can be a non-essential amino acid, such as alanine, arginine, asparagine, aspartic acid, cysteine, glutamic acid, glutamine, glycine, ornithine, proline, serine, or tyrosine.

A target molecule can be a non-proteinogenic amino acid. For example, a target molecule can be an amino acid selected from lanthionine, 2-aminoisobutyric acid, dehydroalanine, N-formylmethionine, gamma-amino-butyric acid (GABA), hydroxyproline, carnitine, ornithine, S-adenosylmethionine, citrulline, beta alanine (3-aminopropanoic acid), canavanine, mimosine, or aspartame.

A target molecule can be an amino acid derivative, such as 5-hydroxytryptophan, L-dihydroxyphenylalanine, or eflornithine.

In some embodiments, the target molecule can be an amino acid and the corresponding binding aptamer has a nucleic acid sequence with one or more unpaired bases such that a metal complex can bind a pocket formed by the one or more unpaired bases and also binds the target amino acid. For example, the following formulas depict a binding site formed by the G-A mismatch surrounded by binding base pairs (e.g., G-C, G-T, A-T, A-U or analogs).

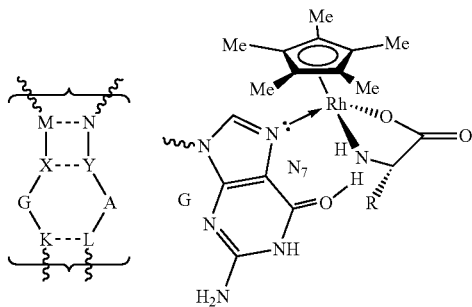

An unbound nucleic acid pocket can appear in a folding program (see e.g., FIG. 7B-FIG. 7E). An unbound nucleic acid pocket does not have to appear in a folding program but can be recognized by its sequences (compare FIG. 7F-G). An unbound nucleic acid pocket can bind Cp*Rh (compare FIG. 7B-G), but can also bind other metals (compare Cu2+ in FIG. 7H).

Sugar Target Molecule.

Shown herein is highly specific glucose sensing by a nucleic acid aptamer (see e.g., Example 4). Results showed an unexpected high affinity of selected aptamers. This is in contrast to prior conventional approaches which have been unable to select an aptamer that recognized glucose.

A target molecule can be a sugar. A target molecule can be a carbohydrate. A target molecule can be a saccharide. A target molecule can be a monosaccharide, including but not limited to glucose, dextrose, fructose, or galactose. For example, a target molecule can be glucose (see e.g., Example 4). As another example, a glucose target molecule can be complexed with a boronic acid derivatization agent (e.g., bis-boronic acid) and an aptamer can be selected against such complex.

A target molecule can be a disaccharide, including but not limited to sucrose (glucose and fructose), maltose (glucose and glucose), or lactose (galactose and glucose). A target molecule can be a hydrogenated form of carbohydrate, whose carbonyl group (aldehyde or ketone, reducing sugar) has been reduced to a primary or secondary hydroxyl group. A target molecule can be a sugar alcohol, such as a polyol, polyhydric alcohol, polyalcohol, or glycitol. A target molecule can be a sugar alcohol, such as methanol, glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, or polyglycitol, or disaccharide combinations thereof. For example, an aptamer raised against a complex of erythritol complexed with a derivatization agent can be used to detect erythritol excreted in urine of a subject.

Lipid Target Molecule.

As described herein, an aptamer can be raised against a lipid target molecule, such as fatty acids, steroids, sphingollipids, or phospholipids complexed with a derivatization agent.

For example, an aptamer can be raised against a fatty acid molecule complexed with a cyclodextrin derivative derivatization agent. A fatty acid is understood as a carboxylic acid with a long aliphatic tail (chain), which is either saturated or unsaturated. A target molecule can be a naturally-occurring fatty acid molecule. A target molecule can be a naturally-occurring fatty acid molecule having at least about 4 up to about 28 carbon atoms. A target molecule can be a fatty acid molecule derived from a monoglyceride, diglyceride, triglyceride, phospholipid, sphingolipid, or ganglioside. A target molecule can be a free fatty acid molecule.

A target molecule can be a short-chain fatty acid (e.g., fatty acid with aliphatic tails of fewer than six carbons, such as butyric acid); a medium-chain fatty acid (e.g., a fatty acid with aliphatic tails of 6-12 carbons, which can form medium-chain triglycerides); a long-chain fatty acid (e.g., fatty acids with aliphatic tails 13 to 21 carbons); or very long chain fatty acids (e.g., fatty acids with aliphatic tails longer than 22 carbons).

A target molecule can be a saturated fatty acid molecule. For example, a target molecule can be a saturated fatty acid molecule selected from caprylic acid, capric acid, lauric acid, myristic acid, palmitic acid, stearic acid, arachidic acid, behenic acid, lignoceric acid, or cerotic acid, or derivatives thereof.

A target molecule can be an unsaturated fatty acid molecule. For example, a target molecule can be an unsaturated fatty acid molecule selected from myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, or docosahexaenoic acid, or derivatives thereof. As another example, a target molecule can be an unsaturated fatty acid molecule selected from linolenic acid (LA), a-linolenic acid (ALA), eicosapentaenoic acid (EPA), or docosahexaenoic acid (DHA).

A target molecule can be a steroid molecule. A steroid is understood as a type of organic compound containing a characteristic arrangement of four cycloalkane rings joined to each other. A target molecule can be, for example, a steroid molecule selected from a cholestane, a cholane, a pregnane, an androstane, a gonane, or an estrane. A target molecule can be, for example, a steroid molecule selected from cholesterol, estradiol, testosterone, progesterone, medrogestone, β-sitosterol, or dexamethasone.

A target molecule can be a sphingolipid or a phospholipid. For example, a target molecule can be a sphingosine-phosphate, sphingomyeline, ganglioside, or phosphatidylcholine.

Other Small Molecules.

A target molecule can be a small molecule. As described herein, an aptamer can be raised against a small molecule complexed with a derivatization agent. A small molecule target having relatively few native features that would otherwise raise a large or complex aptamer can be especially suited for the approach described herein. For example, a target molecule can be a catechol (e.g., dopamine and L-DOPA (L-3,4-dihydroxyphenylalanine)).

A target molecule can be a lead-like small molecule or a drug-like small molecule. For example, a target molecule can be a hydrophobic lead-like or a hydrophobic drug-like molecule. A lead-like small molecule is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like small molecule is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249).

Formation of Complex

As described herein, formation of a complex between a target molecule and a derivatization agent allows selection of a specific, high affinity aptamer to the complex.

A target molecule and a derivatization agent can be combined in any suitable fashion (e.g., in solution) to allow the derivatization agent to derivatize (e.g., non-specifically) a functional group present. For example, a target molecule and a derivatization agent can be combined in solution to allow the derivatization agent to derivatize (e.g., non-specifically derivatize) a functional group present (e.g., any functional group present).

An aptamer can bind at high affinity to the complex of target molecule and derivatization agent. In some embodiments, an aptamer does not bind to target molecule or derivatization agent alone.

In some embodiments an aptamer can bind to a derivatization agent with lesser affinity than to the complex of target molecule and derivatization agent. In some embodiments an aptamer can bind to a target molecule with lesser affinity than to the complex of target molecule and derivatization agent. In some embodiments an aptamer can bind to a derivatization agent or target molecule with lesser affinity than to the complex of target molecule and derivatization agent. In some embodiment, an aptamer does not substantially bind to a target molecule and can bind to derivatization agent in a different conformation than with the complex.

In some embodiments, an aptamer may not form a stable stem in the presence of derivatization agent, but can form a stable stem upon addition of complex.

Thus is provided a novel and unexpected ability to dilute-and-measure analyte.

Selection of Aptamer

Described herein is a direct protocol for isolation of high-affinity oligonucleotide-based sensors (e.g., aptameric) reporting small molecules complexed in situ with their synthetic receptors. Various embodiments of the protocol can allow isolation of oligonucleotides responsive to targets that have previously resisted attempts to identify aptamers against them (see e.g., Example 1). For example, using methods described herein, oligonucleotides responding to either high or low concentrations of glucose were selected, a result not previously achieved under conventional approaches (see e.g., Example 4).

Aptamer selection processes against unmodified target molecules are well known (see generally, Oliphant et al. 1989 Mol. Cell Biol. 9, 2944-2949; Tuerk and Gold 1990 Science 249, 505-510; Ellington and Szostak 1990 Nature 346, 818-822). Such conventional processes include systematic evolution of ligands by exponential enrichment (SELEX); selected and amplified binding site (SAAB) or cyclic amplification and selection of targets (CASTing). Except as otherwise noted herein, therefore, the process of the present disclosure can be carried out in accordance with such processes. For example, conventional aptamer selection technique may be used against the novel complex of a derivatization agent and a target molecule (as described herein) rather than against merely the conventional non-modified target. For example, kinetic capillary electrophoresis can be used for the selection of aptamers (e.g., smart aptamers).

The present disclosure provides a viable alternative to a conventional approach of pursuing high affinity, high complexity receptors for simple small molecules. Rather, as described herein, it can be advantageous for isolation of suitable aptamers to increase the complexity of targets via in situ, dynamic, or reversible complexation of the target with a derivatization agent (e.g., a reversible derivatization agent). Such complexation can provide additional epitopes for interactions with potential aptamers and these aptamers can be less structurally complex given the added complexity of the target.

Furthermore, aptamers specifically binding to the complex can be isolated rather than those binding individual components of the complex. Thus is provided, in various embodiments, methods for identifying small to medium sized aptamers against simple small molecules with otherwise few epitopes by turning such simple small molecules into high affinity ligands through derivatization.

Aptamer selection can include providing a large oligonucleotide library, e.g., of randomly generated sequences of fixed length flanked by constant 5' and 3' ends that can serve as primers. Sequences in the library can be exposed to a complex of a derivatization agent and a target molecule, and those sequences that do not bind the target can be removed (e.g., by affinity chromatography). Sequences can be eluted and amplified by PCR to prepare for subsequent rounds of selection in which the stringency of elution conditions can be increased to identify desirable (e.g., tightest-binding) sequences.

In some embodiments, an RNA library can be used to omit the constant primer regions (which may stabilize secondary structures that are unstable when formed by the random region alone), thereby increasing ease of removal after the selection process because they stabilize secondary structures that are unstable when formed by the random region alone (see generally, Jarosch et al. 2006 Nucleic Acids Res 34(12), e86).

In some embodiments, explicit counter-selection of aptamers against derivatization agent alone or against target molecule alone can be performed.

Selections can be performed in a media containing a desired sample type (e.g., urine, serum, etc.) for both selection and counter-selection, which can minimize the variability of these matrices and account for interferences. Selection conditions and added cofactors can increase the affinity of aptamers (e.g., for amino acids without side-chains that display strong epitopes).

The present disclosure overcomes various problems with conventional aptamer selection. One obstacle to broad conventional use of aptamers in bioanalysis is that various small molecule targets are missing epitopes that can effectively interact with nucleic acids (e.g., hydrophobic surfaces and positively charged functionalities), and this in turn leads to the need for highly complex aptamers, inaccessible through conventional SELEX protocols. For example, glucose is a small molecule for which no aptamers have ever been reported in peer-reviewed literature, despite its significance and commercial value.

Even where a small molecule target has some moiety against which, at least in principle, an aptamer can be raised (e.g., naturally occurring oligonucleotide receptors against minimalist targets poor with epitopes, such as fluoride anion and glycine, see generally Mandal et al. 2004 Science 306, 275-279; Baker et al. 2012 Science 335(6065), 233-235), such natural receptors have substantial informational complexity, measured by a number of bases needed to define their highly structured binding sites. Conventional approaches, such as in vitro selection and amplification (SELEX) methods used to select aptamers from random oligonucleotide libraries, are not well suited for isolation of structurally complex aptamers. And, even when a conventionally selected aptamer against a difficult small molecule target is available, its affinity can be too low to be analytically useful. Furthermore, conventional tools to optimize aptamer affinity are lacking (cf. affinity-maturation process for antibodies).

Various approaches described herein are distinguished from conventional protocols. Prior work involved use of organic synthetic receptors as cofactors for aptamers, in which a tartarate-citrate receptor based on boronic acid was incorporated in aptamers with a goal of impacting it's selectivity (see e.g., Manimala et al. 2004 J. Am. Chem. Soc. 126, 16515-16519). But a resulting aptamer-receptor complex in this prior study had lesser affinity to tartarate and citrate than the receptor itself, while its selectivity indeed changed due to these different drops in affinity. Furthermore, in that prior study, both receptor and receptor target complexes induced similar conformational changes in aptamer at the equally low concentrations (20 μM), indicating similar binding affinities.

Embodiments of the present disclosure differ from prior studies in at least several ways.

In some embodiments, counter-selection of aptamers against a derivatization agent alone or against a target molecule alone can be used in, with, or after the process of aptamer selection for the complex of derivatization agent and target molecule (see e.g., FIG. 1). A counter-selection step can disfavor incorporation of a receptor (e.g., of the derivatization agent alone or the target molecule alone) into an aptameric sensor on its own or can lead to an increase of analytical sensitivity or can lead to a different mode of sensing with cofactor alone. Reasoning supporting such an approach is at least as follows. If an aptamer incorporates a derivatization agent prior to its binding to the target molecule, there may be no reason to assume that functionalities in the derivatization agent that are binding to the aptamer will not be binding to the target molecule as well. In other words, binding to the derivatization agent alone may be competing with binding to the target molecule, which may result in decreased affinity. If an aptamer binds substantially only to the complex of derivatization agent and target molecule after such complex is formed, and if it binds tightly, it can stabilize formation even at very low concentration. Thus, in the presence of an excess of receptor, aptamer can detect and stabilize very low concentrations of ligands (i.e., target molecules complexed with derivatization agent).

In some embodiments, elution from a solid-state bound target is not performed during selection. Rather, affinity elution can be performed from a library attached to a solid state with a target molecule, not via a displacement of target molecule with a non-target from a complex of target molecule and derivatization agent. This change can avoid selection pressure against high-affinity interactions with a complex of target molecule and derivatization agent or can lead to an increase in affinity.

Aptamer

As described herein, an aptamer can be identified against a complex of a derivatization agent and a target molecule. An aptamer, as the term is used herein, is understood as a nucleic acid species engineered through repeated rounds of selection (e.g., in vitro selection) to bind to a target molecule, such as small molecules, proteins, nucleic acids, cells, tissues, or organisms.

For those small molecules for which aptamer have been previously successfully isolated, such as amino acids, various embodiments of the method described herein can provide significantly superior affinity or reduced aptamer size, or both.

Before, during, or after recognition of a target molecule, an aptamer can bind by complementary nucleic acid base pairing, which can create a secondary structure, such as a short helical arm or a single stranded loop. A combination of these secondary structures can result in the formation of a tertiary structures, which can allow an aptamer to bind to a target molecule via van der Waals forces, hydrogen bonding, or electrostatic interaction (similar to an antibody binding to an antigen). When such tertiary structure forms, some, most, or all of the aptamer can fold into a complex (e.g., a stable complex) with the target molecule forming an aptamer-target complex. This three-dimensional structure can allow an aptamer to function like an antibody, which contrasts to conventional thinking which held that polynucleic acids were merely linear, information holding structures.

An aptamer can be a nucleic acid aptamer. An aptamer can be a DNA aptamer. A DNA aptamer can be relatively more stable, cheaper, and easier to produce than an RNA aptamer. An aptamer can be an RNA aptamer. An RNA aptamer can have a relatively more diverse three-dimensional structure than a DNA aptamer. An aptamer can be an XNA aptamer. An aptamer can be a smart aptamer, selected with a pre-defined equilibrium constants ($K_d$), rate constants ($k_{off}$, $k_{on}$), and thermodynamic ($\Delta H$, $\Delta S$) parameters of aptamer-target interaction.

An aptamer described herein can be modified, e.g., to resist degradation in a sample. For example, sugar modifications of nucleoside triphosphates can render a resulting aptamer resistant to nucleases found in serum. As another example, changing a 2'OH group of ribose to a 2'F or 2'NH$_2$ group can yield an aptamer having increased stability or a longer half-life, such as in blood-containing sample or in an in vitro or in vivo environment (see e.g., Brody and Gold 2000 Rev Molec Biol 74(1), 5-13). As another example, conjugating an aptamer to a higher molecular weight vehicle can increase stability or half-life in an in vitro or in vivo environment. As another example, an aptamer can be conjugated to a nanomaterial.

An aptamer as described herein can be at least about 15 oligonucleotides. An aptamer as described herein can be up to about 100 oligonucleotides. For example, an aptamer as described herein can be at least about 15 oligonucleotides up to about 100 oligonucleotides. As another example, an aptamer as described herein can be at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more oligonucleotides. It is understood that recitation of each of these individual values includes ranges there between.

Nucleic acid sequences for exemplary aptamers are provided herein. It is understood that an aptamer can have a nucleic acid sequence according to the discrete exemplary sequence provided, or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) a target molecule complexed with a derivatization agent. One of ordinary skill will understand that certain regions of the aptamer are more robust with respect to nucleic acid substitution. For example, stem regions of a secondary or tertiary structure of an aptamer may have reduced impact on target molecule binding, and so, nucleic acid substitutions in these regions can be more freely made. In contrast, secondary or tertiary structure regions of an aptamer associated with binding to target molecules may be more sensitive, and so, may require more conservative substitutions or fewer substitutions. Similarly, regions of an aptamer important or critical to certain secondary or tertiary structural features may be more sensitive, and so, may require more conservative substitutions or fewer substitutions. In some embodiments, nucleic acid sequence identity can be lower in stem regions (e.g., at least about 80%, at least about 85%, or at least about 90%) compared to regions associated with binding a target molecule or regions important or critical to secondary or tertiary structural features (e.g., at least about 90%, at least about 95%, or at least about 99%).

An aptamer as described herein can have an equilibrium constant Kd of about 1 pM up to about 100 µM. An aptamer having a Kd as low as about 1 pM to about 100 pM can be with respect to a target molecule, such as a sugar, natively on a surface, such as a cell surface. An aptamer as described herein can have an equilibrium constant Kd of about 1 pM up to about 10.0 µM. As another example, an aptamer as described herein can have an equilibrium constant Kd of about 1 pM up to about 10.0 µM; about 1 pM up to about 1.0 µM; about 1 pM up to about 100 nM; about 100 pM up to about 10.0 µM; about 100 pM up to about 1.0 µM; about 100 pM up to about 100 nM; or about 1.0 nM up to about 10.0 µM; about 1.0 nM up to about 1.0 µM; about 1 nM up to about 200 nM; about 1.0 nM up to about 100 nM; about 500 nM up to about 10.0 µM; or about 500 nM up to about 1.0 µM.

As another example, an aptamer as described herein can have an equilibrium constant Kd of about 1 pM, about 50 pM, about 100 pM, about 150 pM, about 200 pM, about 250 pM, about 300 pM, about 350 pM, about 400 pM, about 450 pM, about 500 pM, about 550 pM, about 600 pM, about 650 pM, about 700 pM, about 750 pM, about 800 pM, about 850 pM, about 900 pM, about 950 pM, about 1 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 250 nM, about 300 nM, about 350 nM, about 400 nM, about 450 nM, about 500 nM, about 550 nM, about 600 nM, about 650 nM, about 700 nM, about 750 nM, about 800 nM, about 850 nM, about 900 nM, about 950 nM, about 1 µM, about 10 µM, about 20 µM, about 30 µM, about 40 µM, about 50 µM, about 60 µM, about 70 µM, about 80 µM, about 90 µM, or about 100 µM. It is understood that ranges between different combinations of Kd listed above are contemplated.

Unpaired Bases.

An aptamer as described herein can have a nucleic acid sequence with one or more unpaired nucleic acid bases. An aptamer with one or more unpaired nucleic acid bases can form a binding pocket providing for binding of the target molecule and the derivatization agent. For example, an aptamer with one or more unpaired nucleic acid bases can bind a derivatization agent and an amino acid target molecule. As another example, an aptamer with one or more unpaired nucleic acid bases can bind a metal ion complex derivatization agent (e.g., Cp*Rh(III)) and an amino acid target molecule. An example of a metal-complex binding motif of an aptamer with one or more unpaired nucleic acid bases and binding of Cp*Rh(III) and an amino acid is as follows:

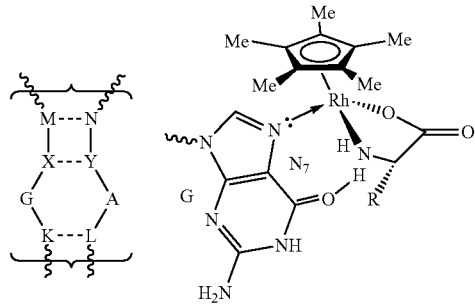

In the above motif, the binding site formed by the G-A mismatch surrounded by binding base pairs (e.g., G-C, G-T, A-T, A-U or analogs).

Figures 7A, 7B, 7C, 7D:
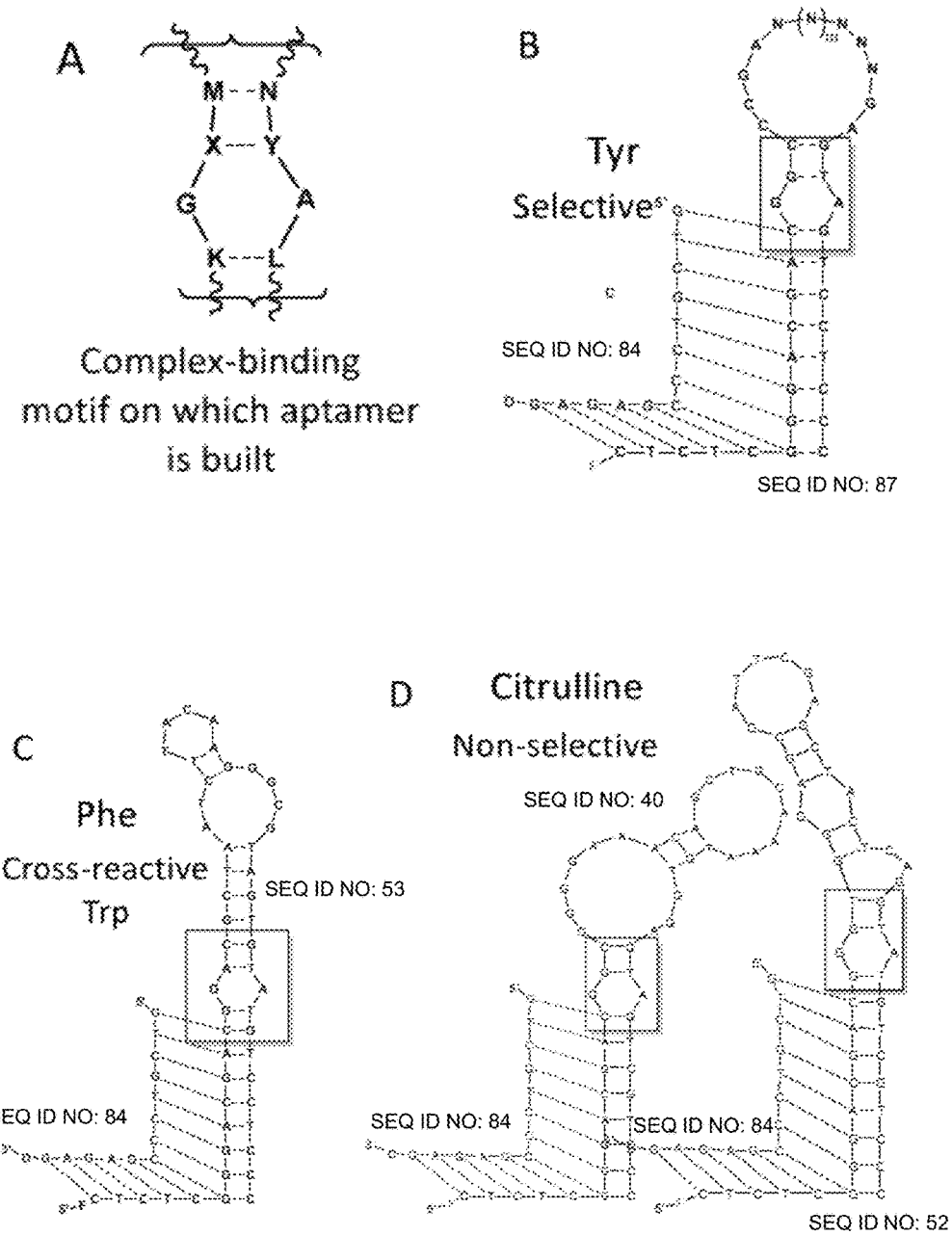
FIG. 7A-FIG. 7H are a series of chemical structures showing aptamers having at least one unpaired base forming a pocket that binds a metal complex or an amino acid target molecule.
Figures 7E, 7F, 7G, 7H:
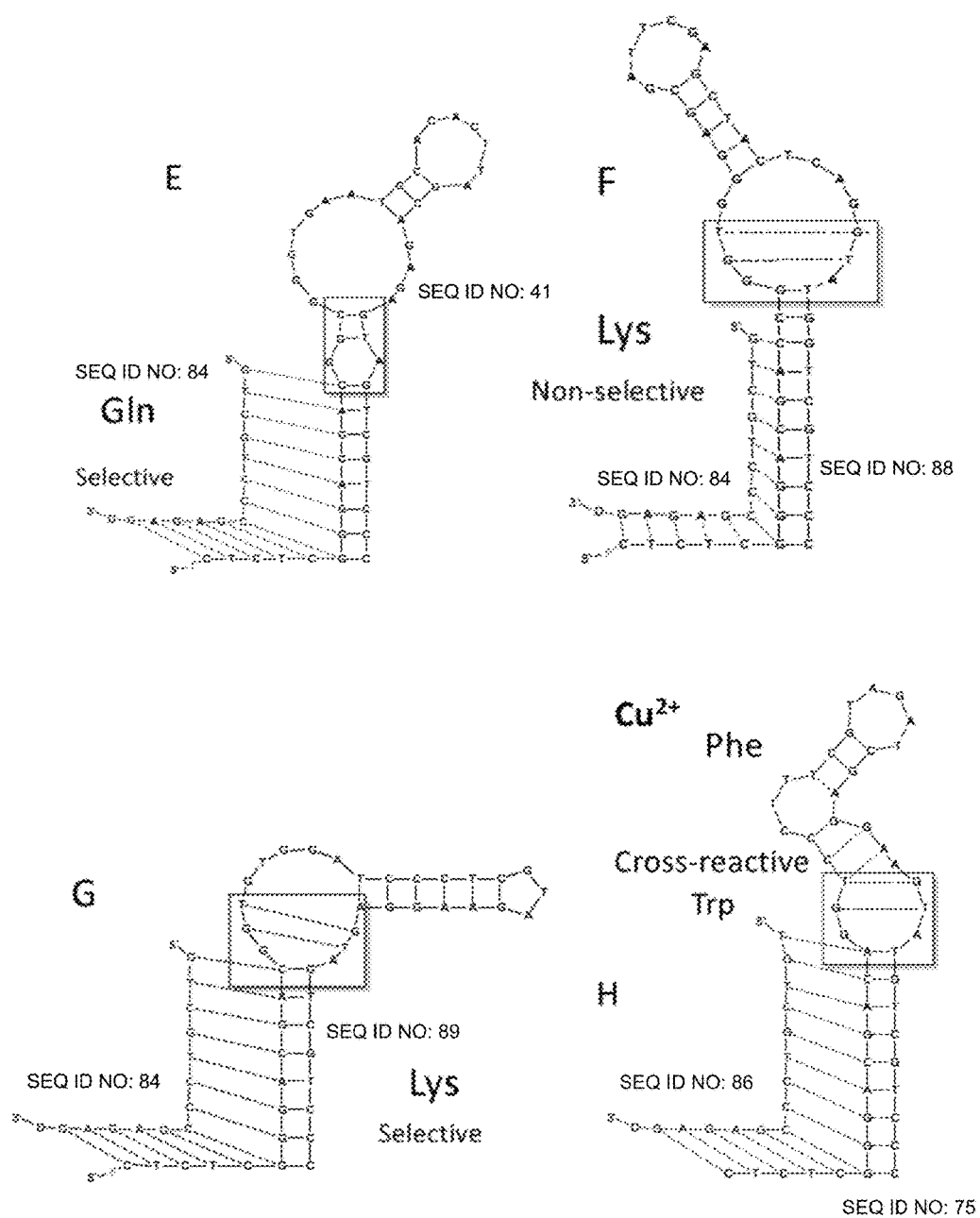
Figures 8A, 8B, 8C:
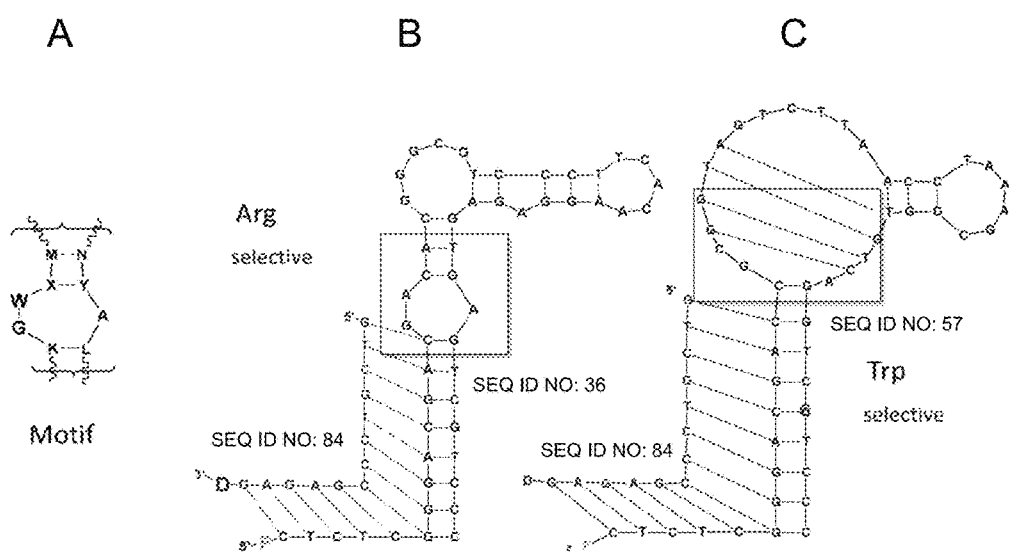
FIG. 8A-FIG. 8C is a series of chemical structures showing aptamers having at least two unpaired bases forming a pocket that binds a metal complex or an amino acid target molecule.
Figures 9A, 9B, 9C:
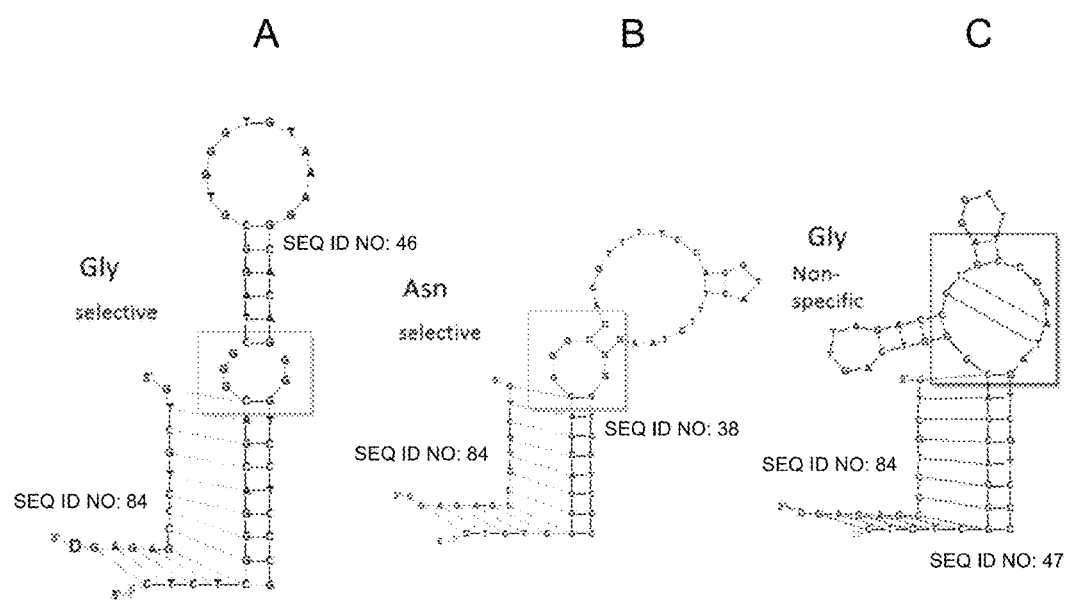
FIG. 9A-FIG. 9C is a series of chemical structures showing aptamers having a plurality of unpaired bases forming a pocket that binds a metal complex or an amino acid target molecule.
Figures 10A, 10B:
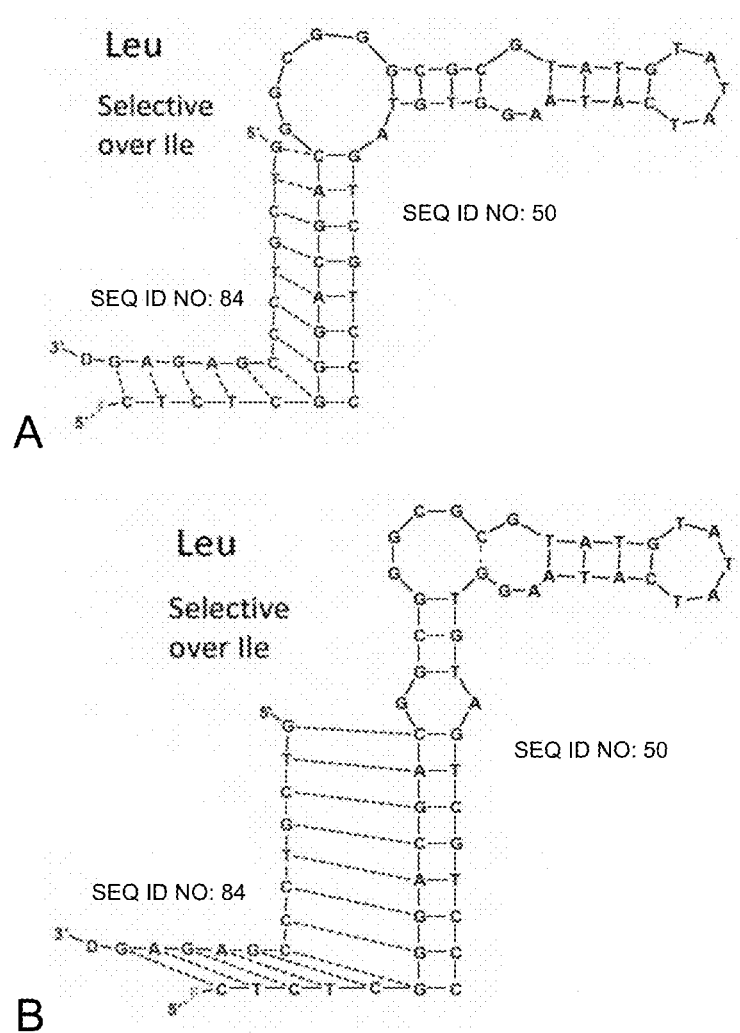
FIG. 10A-FIG. 10B is a series of chemical structures showing multiple folding configurations of LeuCp17 aptamer (SEQ ID NO: 50) selective for Leu over Ile having a plurality of unpaired bases forming a plurality of pockets (compare FIG. 10A and FIG. 10B), one of more of which pockets can bind a metal complex and also an amino acid target molecule. A Cp*Rh(III) can bind more than one site, such as additional G's that can be targeted.
Figure 11A:
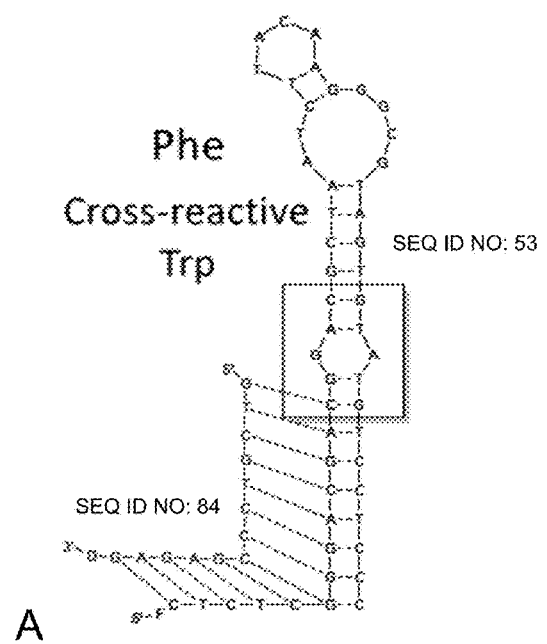
FIG. 11A-FIG. 11B is a chemical structure of PACp*Rh01 aptamer (SEQ ID NO: 53) reactive for Phe and cross-reactive for Trp and a scatter and line plot showing use thereof.
Figure 12A:
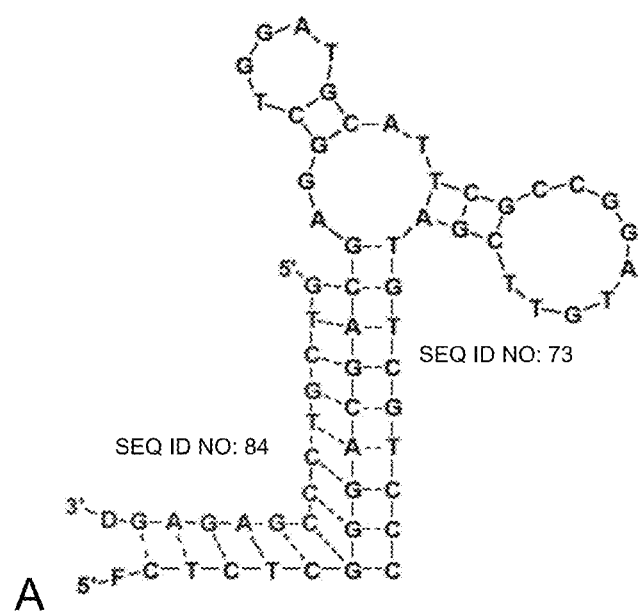
FIG. 12A-FIG. 12D is a series of aptamer structures and scatter and line plots showing use thereof.
Figure 12B:
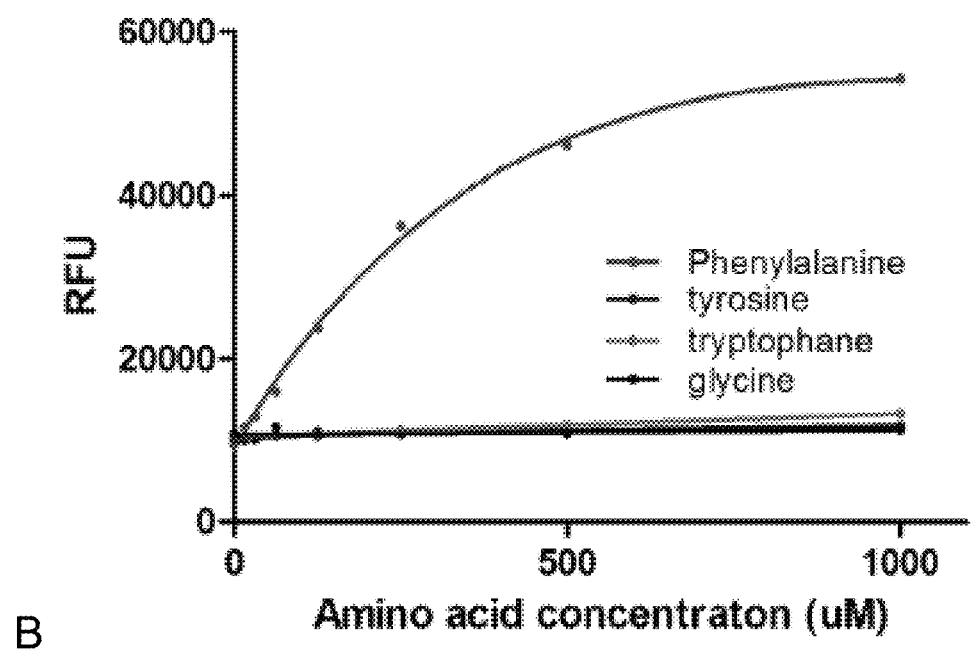
Figure 12C:
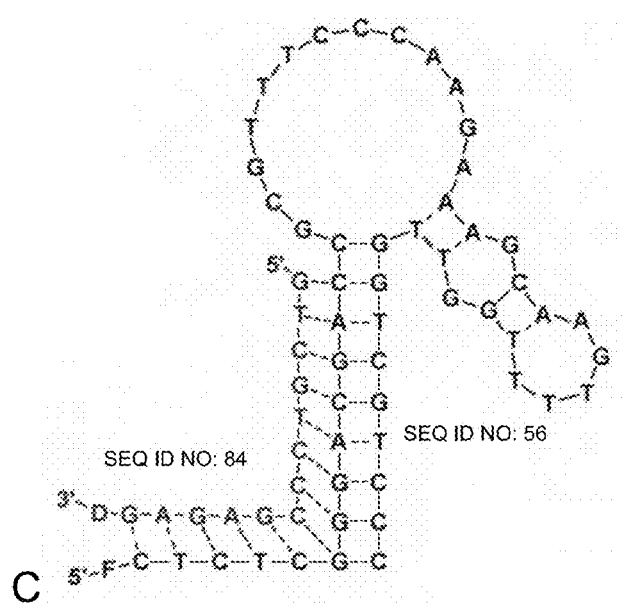

Other examples of an aptamer with one or more unpaired nucleic acid bases are: Tyr selective aptamer Tyr-Cp*Rh (38nt) (SEQ ID NO: 71) as shown in FIG. 7B; Phe cross-reactive Trp aptamer PACp*Rh01 (SEQ ID NO: 53) as shown in FIG. 7C; citrulline non-selective aptamer CIT30N02_Cp*Rh (SEQ ID NO: 40) as shown in FIG. 7D; Gln selective aptamer GlutaCp02 (SEQ ID NO: 41) as shown in FIG. 7E; Lys non-selective aptamer LysCp*Rh18 (SEQ ID NO: 52) as shown in FIG. 7F; Lys selective aptamer LysCp05 (SEQ ID NO: 51) as shown in FIG. 7G; Phe cross-reactive Trp aptamer Cu(II)-Phe10_49 nt (SEQ ID NO: 75) as shown in FIG. 7H; Arg selective ARG01_Cp aptamer (SEQ ID NO: 36) as shown in FIG. 8B; Trp selective HTrp03 aptamer (SEQ ID NO: 57) as shown in FIG. 8C; Gly selective aptamer Gly-Cp sensor (SEQ ID NO: 45) as shown in FIG. 9A; Asn selective aptamer AspaCp03 (SEQ ID NO: 38) as shown in FIG. 9B; Gly non-specific aptamer GLYHW-Cp*Rh06 (SEQ ID NO: 47) as shown in FIG. 9C; LeuCp17 aptamer selective for Leu over Ile (SEQ ID NO: 50) as shown in FIG. 10; PACp*Rh01 aptamer reactive for Phe and cross-reactive for Trp (SEQ ID NO: 53) as shown in FIG. 11A; Phe reactive Cu(II)_Phe01 aptamer (SEQ ID NO: 73) as shown in FIG. 12A; or Phe reactive HPheAl04 aptamer (SEQ ID NO: 56) as shown in FIG. 12C.

An unbound nucleic acid pocket can appear in a folding program (see e.g., FIG. 7B-E). An unbound nucleic acid pocket does not have to appear in a folding program but can be recognized by its sequences (compare FIG. 7F-G). An unbound nucleic acid pocket can bind Cp*Rh (compare FIG. 7B-G), but can also bind other metals (compare Cu²⁺ in FIG. 7H).

Aptamers Specific for Monosaccharide-Derivatization Complex.

An aptamer as described herein can have a nucleic acid sequence comprising SEQ ID NO: 3. An aptamer comprising SEQ ID NO: 3 can bind the target molecule glucose complexed with a bis-boronic derivatization agent. Aptamers specific for the glucose-boronic acid complex can have a nucleic acid sequence comprising: SEQ ID NO: 4 (Glucose-BA_01); SEQ ID NO: 5 (Glucose-BA_07); SEQ ID NO: 6 (Glucose-BA_08); SEQ ID NO: 7 (Glucose-BA_09); SEQ ID NO: 8 (Glucose-BA_10); SEQ ID NO: 9 (Glucose-BA_11); SEQ ID NO: 10 (Glucose-BA_12); SEQ ID NO: 11 (Glucose-BA_13); SEQ ID NO: 12 (Glucose-BA_14); SEQ ID NO: 13 (Glucose-BA_15); SEQ ID NO: 14 (Glucose-BA_16); SEQ ID NO: 15 (Glucose-BA_17); SEQ ID NO: 16 (GLUBA02); SEQ ID NO: 17 (GLUBA09); SEQ ID NO: 18 (GLUBA09_M1); SEQ ID NO: 19 (GLUBA17); SEQ ID NO: 20 (GLUBAN3W10); SEQ ID NO: 21 (GLUBAN3W11); or SEQ ID NO: 22 (GLUBAN3W19), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) glucose complexed with a bis-boronic derivatization agent.

Aptamers specific for the fructose-boronic acid complex can have a nucleic acid sequence comprising: SEQ ID NO: 23 (FrucBA02); SEQ ID NO: 24 (FrucBA02_M1); or SEQ ID NO: 25 (FrucBA05), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) fructose complexed with a bis-boronic derivatization agent.

Aptamers specific for the galactose-boronic acid complex can have a nucleic acid sequence comprising: SEQ ID NO: 26 (GalacBA_05); SEQ ID NO: 27 (GalacBA_01); or SEQ ID NO: 28 (GalacBA_06), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) galactose complexed with a bis-boronic derivatization agent.

Aptamers Binding to Boronic Acid.

Aptamers specific for boronic acid (e.g., a shinkai sensor) can have a nucleic acid sequence comprising: SEQ ID NO: 29 (BAOnly01); or SEQ ID NO: 30 (BAOnly03), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) boronic acid.

Aptamers Binding to Amino Acids.

An aptamer as described herein can bind (e.g., selectively or non-selectively) arginine complexed with a Cp*Rh(III) derivatization agent. An aptamer as described herein can have a nucleic acid sequence comprising SEQ ID NO: 31. An aptamer comprising SEQ ID NO: 13 can bind the target molecule arginine complexed with a Cp*Rh(III) derivatization agent. An aptamer binding to an arginine-Cp*Rh(III) complex can have a nucleic acid sequence comprising: SEQ ID NO: 32 (Arginine-Cp*Rh_02); SEQ ID NO: 33 (Arginine-Cp*Rh_03); SEQ ID NO: 34 (Arginine-Cp*Rh_04); SEQ ID NO: 35 (Arginine-Cp*Rh_05); or SEQ ID NO: 36 (ARG01_Cp), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) arginine complexed with a Cp*Rh(III) derivatization agent.

An aptamer as described herein can bind (e.g., selectively or non-selectively) asparagine complexed with a Cp*Rh(III) derivatization agent. An aptamer binding to an asparagine-Cp*Rh(III) complex can have a nucleic acid sequence comprising: SEQ ID NO: 37 (AspaCp01); SEQ ID NO: 38 (AspaCp03); or SEQ ID NO: 39 (AspaCp04), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) asparagine complexed with a Cp*Rh(III) derivatization agent.

An aptamer as described herein can bind (e.g., selectively or non-selectively) citrulline complexed with a Cp*Rh(III) derivatization agent. An aptamer binding to a citrulline-Cp*Rh(III) complex can have a nucleic acid sequence comprising SEQ ID NO: 40 (CIT30N02_Cp*Rh), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) citrulline complexed with a Cp*Rh(III) derivatization agent.

An aptamer as described herein can bind (e.g., selectively or non-selectively) glutamine complexed with a Cp*Rh(III) derivatization agent. An aptamer binding to a glutamine-Cp*Rh(III) complex can have a nucleic acid sequence comprising SEQ ID NO: 41 (GlutaCp02); or SEQ ID NO: 42 (GlutaCp15), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) glutamine complexed with a Cp*Rh(III) derivatization agent.

An aptamer as described herein can bind (e.g., selectively or non-selectively) glycine complexed with a Cp*Rh(III) derivatization agent. An aptamer as described herein can have a nucleic acid sequence comprising SEQ ID NO: 43. An aptamer comprising SEQ ID NO: 43 can bind the target molecule glycine complexed with a Cp*Rh(III) derivatization agent. An aptamer binding to an glycine-Cp*Rh(III) complex can have a nucleic acid sequence comprising: SEQ ID NO: 44 (Glycine-Cp*Rh_01); SEQ ID NO: 45 (Gly-Cp); SEQ ID NO: 46 (Gly-Cp+1 bp); or SEQ ID NO: 47 (GLYHW-Cp*Rh 06), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) glycine complexed with a Cp*Rh(III) derivatization agent.

An aptamer as described herein can bind (e.g., selectively or non-selectively) leucine complexed with a Cp*Rh(III) derivatization agent. An aptamer binding to a leucine-Cp*Rh(III) complex can have a nucleic acid sequence comprising: SEQ ID NO: 48 (LeuCp01); SEQ ID NO: 49 (LeuCp04); or SEQ ID NO: 50 (LeuCp17), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) leucine complexed with a Cp*Rh(III) derivatization agent.

An aptamer as described herein can bind (e.g., selectively or non-selectively) lysine complexed with a Cp*Rh(III) derivatization agent. An aptamer binding to a lysine-Cp*Rh(III) complex can have a nucleic acid sequence comprising: SEQ ID NO: 51 (LysCp05); or SEQ ID NO: 52 (LysCp*Rh18), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) lysine complexed with a Cp*Rh(III) derivatization agent.

An aptamer as described herein can bind (e.g., selectively or non-selectively) phenylalanine complexed with a Cp*Rh(III) derivatization agent. An aptamer binding to a phenylalanine-Cp*Rh(III) complex can have a nucleic acid sequence comprising: SEQ ID NO: 53 (PACp*Rh01); SEQ ID NO: 54 (PACp*Rh02); SEQ ID NO: 55 (PACp*Rh03); or SEQ ID NO: 56 (HPheAl04), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) phenylalanine complexed with a Cp*Rh(III) derivatization agent.

An aptamer as described herein can bind (e.g., selectively or non-selectively) phenylalanine complexed with a Cu(II) derivatization agent. An aptamer binding to a phenylalanine-Cu(II) complex can have a nucleic acid sequence comprising: SEQ ID NO: 73 (Cu(II)_Phe01); SEQ ID NO: 74 (Cu(II)-Phe10); or SEQ ID NO: 75 (Cu(II)-Phe10_49 nt), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) phenylalanine complexed with a Cu(II) derivatization agent.

An aptamer as described herein can bind (e.g., selectively or non-selectively) tryptophan complexed with a Cp*Rh(III) derivatization agent. An aptamer binding to a tryptophan-Cp*Rh(III) complex can have a nucleic acid sequence comprising: SEQ ID NO: 57 (HTrp03), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) tryptophan complexed with a Cp*Rh(III) derivatization agent.

An aptamer as described herein can bind (e.g., selectively or non-selectively) tyrosine complexed with a Cp*Rh(III) derivatization agent. An aptamer as described herein can have a nucleic acid sequence comprising SEQ ID NO: 58. An aptamer comprising SEQ ID NO: 58 can bind the target molecule tyrosine complexed with a Cp*Rh(III) derivatization agent. An aptamer binding to an tyrosine-Cp*Rh(III) complex can have a nucleic acid sequence comprising: SEQ ID NO: 59 (Tyrosine-Cp*Rh_02); SEQ ID NO: 60 (Tyrosine-Cp*Rh_03); SEQ ID NO: 61 (Tyrosine-Cp*Rh_04); SEQ ID NO: 62 (Tyrosine-Cp*Rh_05); SEQ ID NO: 63 (Tyrosine-Cp*Rh_06); SEQ ID NO: 64 (Tyrosine-Cp*Rh_07); SEQ ID NO: 65 (Tyrosine-Cp*Rh_08); SEQ ID NO: 66 (Tyrosine-Cp*Rh_09); SEQ ID NO: 67 (Tyrosine-Cp*Rh_10); SEQ ID NO: 68 (Tyrosine-Cp*Rh_11); SEQ ID NO: 69 (Tyrosine-Cp*Rh_12); SEQ ID NO: 70 (Tyrosine-Cp*Rh_13); SEQ ID NO: 71 (Tyr-Cp*Rh (38nt)); or SEQ ID NO: 72 (HTyrs07), or a sequence at least 80% identical thereto (e.g., at least 85%, at least 90%, at least 91%, at least 92%, at least 93%, at least 94%, at least 95%, at least 96%, at least 97%, at least 98% or at least 99%) and binding (e.g., selective or non-selective) tyrosine complexed with a Cp*Rh(III) derivatization agent.

Diagnostics

Aptamers described herein can be used in diagnostic applications.

Various embodiments of the method can address specific bioanalytical needs, such as mix-and-measure assays of diagnostic increases in small molecules in challenging biological matrices. The simplicity and general applicability of methods described herein or broad availability of synthetic receptors for small molecules provide applications of aptamers in clinical chemistry that have not been previously possible.

Conventional aptamer diagnostic protocols can be adapted by an artisan of ordinary skill for use with aptamers disclosed herein. Generally, an additional step includes mixing a sample containing or suspected of containing a target molecule with a derivatization agent so as to form a complex. Such complex can then be detected with an aptamer disclosed herein according to a conventional assay. Thus is provided a mix-and-measure modification that can be made to assays for detection of small molecule targets in challenging biological matrices.

Aptamer usage in diagnostics is well known (see generally, Jayasena 1999 Clin Chem 45(9), 1628-1650; Mascini 2009 Aptamers in Bioanalysis, Wiley-Interscience, $1^{st}$ Ed., ISBN-10: 0470148306). Except as otherwise noted herein, therefore, the process of the present disclosure can be carried out in accordance with such processes.

An aptamer described herein can be immobilized on a surface suitable for diagnostic applications, such as gold films, gold particles, silicates, silicon oxides, polymers, metallic substrates, biocoatings including avidin or avidin derivatives, quantum dots, carbon nanotubes, superparamagnetic iron oxide nanoparticles, or carbohydrates (see generally, Balamurugan et al. 2008 Anal Bioanal Chem 390, 1009-1021; Famulok et al. 2007 Chemical Reviews 107(9), 3715-3743; see generally, Lee et al. 2010 Advanced Drug Delivery Systems 62(6), 592-605). Chemical protocols for covalent attachment of aptamers to functionalized surfaces is understood in the art and such protocols can be adapted for aptamers disclosed herein. For example, an aptamer of the present disclosure can be attached to a solid surface array.

An aptamer described herein can be used in conjunction with a fluorescent, colorimetric, magnetic resonance imaging, or electrochemical sensor or protocol (see generally, Lee et al. 2010 Advanced Drug Delivery Systems 62(6), 592-605).

An aptamer described herein can be used to detect a target molecule in a sample. A sample can be a biological sample. A sample can be a biological sample from a subject. The subject can be an animal subject, including a mammal, such as horses, cows, dogs, cats, sheep, pigs, mice, rats, monkeys, hamsters, guinea pigs, and chickens, and humans. For example, the subject can be a human subject.

A biological sample can be a fluid sample or a solid sample. A biological sample can be a urine sample, a saliva sample, a blood sample, a serum sample, a plasma sample, an amniotic fluid sample, a cerebrospinal fluid sample, a sweat sample, an exhaled breath condensate sample, or a solid tissue sample. For example, the sample can be a blood sample, such as a peripheral blood sample. As another example, a sample can be a urine sample.

For example, an aptamer described herein can be used as an amino acid marker. Such amino-acid specific aptamer can be used to detect an amino acid in a biological sample (e.g., a urine sample).

An aptamer described herein can be used to detect a target molecule associated with a disease or condition. Diagnostic methods using an aptamer described herein can be performed on a subject having, diagnosed with, suspected of having, or at risk for developing a disease or condition associated with a target molecule. A determination of the need for diagnosis can be assessed by a history and physical exam consistent with the disease or condition at issue. Conventional diagnostic protocols of a disease or disorder associated with a target molecule can be adapted accordingly to use aptamers as disclosed herein.

Amino acids that are diagnostic or contribute to diagnosis for specific disorders are known in the art (see generally, Blau 2004 Physician's Guide to the Laboratory Diagnosis of Metabolic Diseases, 2d Ed., Springer, ISBN-10: 354042542X). Methods described herein for isolating an aptamer specific for an amino acid can be directed towards an amino acid known to be diagnostic or contribute to diagnosis for specific disorders. An aptamer isolated according the approach described herein can be used to detect an amino acid in a sample, thereby providing or contributing to a diagnosis for the associated disease or disorder.

For example, an aptamer described herein can be used as a diagnostic of a congenital disease associated with the target molecule. As another example, a tyrosine-specific aptamer can be used to diagnose tyrosinemia in a subject. As another example, an aptamer specific for the amino acid citrulline can be used to diagnose or aid in the assessment of small intestinal function (e.g., transplant recipients, including graft-vs-host disease). As another example, an aptamer specific for the carbohydrate galactose can be used to diagnose or aid in the diagnosis of several forms of galactosemia.

Furthermore, an aptamer developed as described herein can be used to monitor an amino acid associated with a disease or disorder and to measure compliance. For example, several amino acid disorders are known to be treated by specific diets and aptamers described herein can provide a tools allowing a subject or caregiver to monitor the efficacy of a specific diet. As another example, aptamers specific for valine, leucine, or isoleucine (branched chain amino acids) can be used for evaluation of nutritional status (e.g., dietary supplement used by athletes).

Several inborn errors of amino acid metabolism can be treated by special diets that either restrict protein intake (e.g., urea cycle defects, phenylketonuria, tryosinemia, glycine cleavage deficiency and others) or supplement amino acids (e.g., 3-phosphoglycerate dehydrogenase deficiency, MELAS syndrome and others). Conventional treatment involves weekly or monthly determination of amino acid profiles and there are no methods or tools that allow monitoring individual amino acids on a daily basis (cf. glucose profiles in diabetes). Aptamers described herein and sensitive to the amino acid associated with such inborn errors of amino acid metabolism can be used to monitoring individual amino acids on an hourly, daily, weekly, monthly, or yearly basis. Exemplary inborn errors of amino acid metabolism are provided in the TABLE 1.

| Disease | Change to Small Molecule Indicative of Diagnosis |
| --- | --- |
| Phenylketonuria, (several types) | Phenylalanine, tyrosine |
| Tyrosinemia - (several types, newborn immaturity and inborn errors Hawksinuria | Tyrosine, succinylacetone, methionine |
| Glycine cleavage system deficiency | Glycine |
| 3-Phosphoglycerat dehydrogenase deficiency | Glycine |
| Proprionicacidemia | Glycine |
| Methylmalonicacidemia | Glycine/methionine |
| Histidinemia | Histidine |
| MSUD (Maple syrup urine disease) several forms | Leucine, valine, isoleucine alloisoleucine, |
| Isovaleric academia | Leucine, glycine |
| Homocystinuria (Cystathionine beta-synthase deficiency, folate and B12 metabolism) | Homocysteine, methionine |
| Urea cycle defects (several types) | Citrulline, arginine, Argininosuccinate, Orotic acid, Ammonia |
| Citrullinemia type 2 (citrindefiency) | Citrulline, galactose |

A method based on aptamers developed as described herein can improve current diagnostic approaches in clinically relevant conditions, extend diagnostic capacity to low-prevalence conditions that remain undiagnosed due to economic and technical reasons, uncover yet unrecognized alterations in metabolism, or be used in monitoring the general health of populations. Such methods can be effective when a health issue is characterized through a truly gross shift in patterns of metabolite families, typical for serious metabolic problems, such as metabolic disorders due to genetic polymorphisms (inborn errors). Gross shifts of dominant components in the range of micro-to-millimolar concentrations can be well suited for analysis as described herein, including urinalysis for metabolic errors. Furthermore, analysis described herein (e.g., via arrays) can be useful in other biological fluids, such as serum, saliva, amniotic fluid, and CSF.

Over 98% of newborns in the US participate in a comprehensive program for mass screening for inborn errors of metabolism on blood spots; this process, made relatively fast and inexpensive by tandem mass spectroscopy coupled with computer analysis, covers 30+ inborn errors of metabolism, treatable if caught at early stages, and 20+ untreatable conditions. While newborn screening is an undeniable success in developed countries, serious problems remain. For example, the rate of false positives can be as high as 1.3%, with the positive predictive value of the test ranging from 3% (meaning 97% of positives are false) to 50%, depending on individual states (overall leading to estimated 200,000 false positives each year in the US).

Approaches described herein can diagnose or monitor inborn errors that interfere with metabolic processes involving amino acids. If identified early, the most serious consequences of these errors, such as mental retardation, can be prevented, e.g., by careful changes in diet and by providing supplements/drugs. The National Academy of Clinical Biochemistry stresses in its "Practice Guidelines to Follow-up Testing for Metabolic Diseases Identified in Newborn Screening" that a comprehensive amino-acid analysis provides relevant and timely contribution to the differential diagnosis, with most tests for amino acids performed in serum. The current analytical standard for amino acid analysis in urine is post-derivatization cation exchange chromatography with photometric detection of ninhydrin adducts; iTRAQ®-LC-MS/MS, and post-derivatization GC-MS are being studied as alternatives.

In some embodiments, diagnostic methods disclosed herein may not fully eliminate the need for chromatography and other diagnostic steps (e.g., genetic). But such diagnostic methods can give a rapid single-step option for sorting out cases identified initially as low-to-moderate risk; thus, as a fast second-tier confirmatory test, it can allow early focus on correct diagnosis, and, if false positive is established, it can provide important relief to a subject.

In post-prandial periods in patients with metabolic disorders that interfere with utilization of amino acids, there can be a transient strong elevation above the renal reabsorption threshold of relevant metabolites in plasma. This can result in spillage into urine, useful to confirm the initial diagnosis or result in analysis of acidic components in urine as part of a differential diagnosis. To preserve homeostasis, unnecessary or toxic compounds are rapidly excreted, thus, increases in urine can be more dramatic than in blood.

In metabolic errors, the shifts in patterns of amino acids can be gross for screened diseases. For example, it is known that in primary aminoacidopathies: (i) in tyrosinemia type 1, changes in concentrations of tyrosine in urine were >20-fold (2000 µmol/g creatinine); branched chain amino acids change only minimally; (ii) in homocystinuria (e.g., cystathionine beta synthase deficiency), it is known that homocystine becomes detectable in urine (from ~0 to about 100 µmol/g creatinine); (iii) in urea cycle disorders, e.g., citrullinemia (ASD) and argininosuccinicaciduria (ALD) (of interest for late onset as well), it is known that citrulline in urine increases more than 50-fold from <200 to >10,000 µmol/g creatinine) and argininosuccinicate from ND to >1000 µmol/g creatinine; (iv) in MSUD at day 3, it is known that leucine (also other branched-chain amino acids) increases >10-fold in serum (e.g., from <200 to ~2000 µM) with expected spillage into urine; any detection of alloisoleucine in either urine or serum (ND to av. 200 μM) is known to be indicative of the diagnosis. In each of these cases, an aptamer can be developed, as described herein, to be sensitive to a metabolite above and thus contribute to diagnosis of the associated disease or disorder.

Provided below is a list of specific diseases and conditions associated with a disruption of levels of an amino acid. Methods described herein for isolating an aptamer specific for an amino acid can be directed towards an amino acid known to be diagnostic or contribute to diagnosis for a specific disease or disorder appearing in the table below. An aptamer isolated according the approach described herein can be used to detect an amino acid in a sample, thereby providing or contributing to a diagnosis for the associated disease or disorder appearing in TABLE 2.

TABLE 2

Pathological values/differential diagnosis of inborn errors

| Amino acid | Source | Value | Value | Disorder(s) |
|---|---|---|---|---|
| All amino acids | U | ↑ | H | Classic galactosemia |
| All amino acids | U | ↑ | H | Fanconi syndrome |
| All amino acids | U | ↑ | H | Fumarylacetoacetase deficiency (Tyrosinemia I) |
| All amino acids | U | ↑ | H | Glutamylcysteine synthetase deficiency |
| All amino acids | U | ↑ | H | Hereditary fructose intolerance |
| All amino acids | U | ↑ | H | Lowe syndrome |
| All amino acids | U | ↑ | H | Vitamin D-dependent rickets |
| Neutral amino acids | U | ↑ | H | Hartnup disorder |
| Alanine | B | ↑ | H | Hyperammonemic syndromes |
| Alanine | B | ↑ | H | Mitochondrial disorders |
| Alanine | B | ↑ | H | Pyruvate/lactate disorders |
| β-alanine | B, U | ↑ | H | β-Alaninemia |
| β-alanine | CSF | ↑ | H | GABA-transaminase deficiency |
| β-alanine | U | ↑ | H | Methylmalonate semialdehyde dehydrogenase deficiency |
| β-alanine | U | ↑ | H | Pyrimidine disorders |
| Allo-isoleucine | B, U | ↑ | H | $E_3$ Lipoamide dehydrogenase deficiency |
| Allo-isoleucine | U | ↑ | H | Ethylmalonic aciduria |
| Allo-isoleucine | B, U | ↑ | H | Maple syrup urine disease |
| α-aminoadipic acid | U | ↑ | H | α-Aminoadipic/α-ketoadipic aciduria |
| α-aminoadipic acid | U | ↑ | H | Kearns-Sayre syndrome |
| β-aminoisobutyric acid | U | ↑ | H | β-Alaninemia |
| β-aminoisobutyric acid | U | ↑ | H | β-Aminoisobutyric acid aminotransferase deficiency (benign genetic marker) |
| δ-Aminolevulinic acid | U | ↑ | H | Hereditary tyrosinemia I |
| Argnine | B | ↓ | L | Creatine deficiency |
| Arginine | U | ↑ | H | Cystinuria |
| Arginine | U | ↑ | H | Dibasic aminoaciduria |
| Arginine | B | ↓ | L | HHH syndrome |
| Arginine | B | ↑ | H | Hyperargininemia |
| Arginine | U | ↑ | H | Lysinuric protein intolerance |
| Arginine | B | ↓ | L | Ornithine aminotransferase deficiency (gyrate atrophy) |
| Argininosuccinate | B, U, AF | ↑ | H | Argininosuccinic aciduria (argininosuccinate lyase deficiency) |
| Aspartic acid | U | ↑ | H | Dicarboxylic aminoaciduria |
| Aspartylglucosamine | B, U | ↑ | H | Aspartylglucosamidase deficiency |
| Carnosine | U | ↑ | H | Carnosinemia |
| Citrulline | B | ↑ | H | Argininosuccinic aciduria (argininosuccinate lyase deficiency) |
| Citrulline | B | ↑ | H | Citrullinemia |
| Citrulline | B | ↓ | L | δ-Pyrroline-5-carboxylate synthase deficiency |
| Citrulline | B | ↓ | L | Lysinuric protein intolerance |
| Citrulline | B | ↓ | L | NAGS, CPS, OTC deficiencies |
| Citrulline | B | ↑ | H | Pyruvate carboxylase deficiency type B |
| Citrulline | B | ↓ | L | Respiratory chain disorders |
| Citrulline | B, U | ↑ | H | Saccharopinuria |
| Cystathionine | B, U | ↑ | H | Cobalamin disorder |
| Cystathionine | B, U | ↑ | H | Cystathionase deficiency |
| Cystathionine | B, U | ↑ | H | Cystathionine β-synthase deficiency |
| Cystathionine | B, U | ↑ | H | Methylene tetrahydrofolate reductase deficiency |
| Cystine | U | ↑ | H | Cystinuria |
| Cystine | U | ↑ | H | Hyperlysinemia |
| Cystine | U | ↑ | H | Hyperornithinemia |
| Cystine | U | ↑ | H | Lysinuric protein intolerance |
| Cystine | B | ↓ | L | Molybdenum cofactor deficiency |
| Cystine | B | ↓ | L | Sulfite oxidase deficiency |
| Ethanolamine | U | ↑ | H | Ethanolaminosis |
| Formiminoglutamic acid | U | ↑ | H | Formiminoglutamic aciduria |
| GABA | B, U | ↑ | H | β-Alaninemia |
| GABA | CSF, B, U | ↑ | H | GABA transaminase deficiency |
| Glutamic acid | U | ↑ | H | Dicarboxylic aminoaciduria |
| Glutamic acid | P | ↑ | H | Glutamic acidemia |

TABLE 2-continued

Pathological values/differential diagnosis of inborn errors

| Amino acid | Source | Value | Value | Disorder(s) |
|---|---|---|---|---|
| Glutamine | CSF | ↑ | H | Adenosine deaminase deficiency |
| Glutamine | B, U | ↑ | H | CPS & OTC deficiencies |
| Glutamine | B, U, CSF | ↑ | H | Hyperammonemic syndromes |
| Glutamine | B | ↓ | L | Maple syrup urine disease |
| Glutathionine | U | ↑ | H | γ-Glutamyl transpeptidase deficiency |
| Glycine | U, B, CSF | ↑ | H | Cobalamin disorders |
| Glycine | U, B, CSF | ↑ | H | D-Gyceric aciduria |
| Glycine | U | ↑ | H | Familial renal iminoglycinuria |
| Glycine | U | ↑ | H | Hyperprolinemia I & II |
| Glycine | U, B, CSF | ↑ | H | Methylmalonic acidemia |
| Glycine | U, B, CSF | ↑ | H | Nonketotic hyperglycinemia |
| Glycine | U, B, CSF | ↑ | H | Propionic acidemia |
| Glycine | B, CSF | ↓ | L | Serine deficiency disorders |
| Glycylproline | U | ↑ | H | Prolidase deficiency |
| Hawkinsin | U | ↑ | H | Hawkinsinuria |
| Histidine | B, U | ↑ | H | Histidinemia |
| Homoarginine | B, U | ↑ | H | Hyperlysinemia |
| Homocarnosine | CSF | ↑ | H | Homocarnosinosis |
| Homocitrulline | U | ↑ | H | HHH syndrome |
| Homocitrulline | B, U | ↑ | H | Saccharopinuria |
| Homocyst(e)ine | U | ↑ | H | Adenosine deaminase deficiency |
| Homocyst(e)ine | B, U | ↑ | H | Cobalamin disorders |
| Homocyst(e)ine | B, U | ↑ | H | Cystathionine β-synthase deficiency |
| Homocyst(e)ine | B, U | ↑ | H | Folate disorders |
| Homocyst(e)ine | B | ↑ | H | Methionine adenosyltransferase deficiency |
| Homocyst(e)ine | B | ↑ | H | Nonketotic hyperglycinemia |
| Homocysteine-cysteine disulfide | B | ↑ | H | Cystathionine β-synthase deficiency |
| Homocysteine-cysteine disulfide | U | ↑ | H | Cystinuria |
| Homocysteine-cysteine disulfide | B | ↑ | H | Hyperhomocysteinemia |
| Hydroxylysine | U | ↑ | H | Hydroxylysinuria |
| Hydroxyproline | U | ↑ | H | Familial renal iminoglycinuria |
| Hydroxyproline | U | ↑ | H | Hydroxyprolinuria |
| Hydroxyproline | U | ↑ | H | Hyperprolinemia I & II |
| Imidodipeptides | U | ↑ | H | Prolidase deficiency |
| Isoleucine | B, U | ↑ | H | $E_3$ Lipoamide dehydrogenase deficiency |
| Isoleucine | B, U | ↑ | H | Maple syrup urine disease |
| Leucine | B, U | ↑ | H | $E_3$ Lipoamide dehydrogenase deficiency |
| Leucine | B, U | ↑ | H | Maple syrup urine disease |
| Lysine | B | ↓ | L | Creatine deficiency |
| Lysine | U | ↑ | H | Cystinuria |
| Lysine | U | ↑ | H | Dibasic aminoaciduria |
| Lysine | B | ↓ | L | HHH syndrome |
| Lysine | B, U | ↑ | H | Hyperlysinemia |
| Lysine | U | ↑ | H | Lysinuric protein intolerance |
| Lysine | B | ↓ | L | Ornithine aminotransferase deficiency (gyrate atrophy) |
| Lysine | B | ↑ | H | Pyruvate carboxylase deficiency type B |
| Lysine | B, U | ↑ | H | Saccharopinuria |
| β-Mercaptolactate-cysteine disulfide | U | ↑ | H | β-mercaptolactate-cysteine disulfiduria |
| Methionine | P, CSF | ↑ | H | Adenosine deaminase deficiency |
| Methionine | B | ↓ | L | Cobalamin disorders |
| Methionine | B, U | ↑ | H | Cystathionine β-synthase deficiency |
| Methionine | B | ↑ | H | Hypermethioninemias |
| Methionine | CSF | ↓ | L | Methylenetetrahydrofolate reductase deficiency |
| Methionine sulfoxide | B | ↑ | H | Cystathionine β-synthase deficiency |
| Methionine sulfoxide | B | ↑ | H | Hypermethioninemias |
| Ornithine | B | ↑ | H | Creatine deficiency |
| Ornithine | U | ↑ | H | Cystinuria |
| Ornithine | B | ↓ | L | Δ-Pyrroline-5-carboxylate synthase deficiency |
| Ornithine | U | ↑ | H | Dibasic aminoaciduria |
| Ornithine | B | ↑ | H | HHH syndrome |
| Ornithine | U | ↑ | H | Hyperlysinemia |
| Ornithine | U | ↑ | H | Lysinuric protein intolerance |
| Ornithine | B | ↑ | H | Ornithine aminotransferase deficiency (gyrate atrophy) |
| Phenylalanine | B | ↑ | H | Hereditary tyrosinemia I |
| Phenylalanine | B, U | ↑ | H | Hyperphenylalaninemia |
| Phenylalanine | B | ↑ | H | Neonatal transient tyrusinemia |
| Phenylalanine | B, U | ↑ | H | PKU |
| Phenylalanine | B, U | ↑ | H | Pterin disorders |
| Phosphoethanolamine | U | ↑ | H | Hypophosphatasia (rickets) |

TABLE 2-continued

Pathological values/differential diagnosis of inborn errors

| Amino acid | Source | Value | Value | Disorder(s) |
|---|---|---|---|---|
| o-Phosphohydroxylysine | U | ↑ | H | o-Phosphohydroxylysinuria |
| Pipecolic acid | B | ↑ | H | Hyperlysinemia |
| Pipecolic acid | U | ↑ | H | Hyperprolinemia II |
| Pipecolic acid | B, U | ↑ | H | Peroxisomal disorders |
| Proline | B | ↓ | L | Δ-Pyrroline-5-carboxylate synthase deficiency |
| Proline | U | ↑ | H | Familial renal iminoglycinuria |
| Proline | B, U | ↑ | H | Hyperprolinemia I & II |
| Proline | B | ↑ | H | Pyruvate carboxylase deficiency type B |
| Saccharopine | B, U | ↑ | H | Saccharopinuria |
| Sarcosine | B, U | ↑ | H | Glutaric acidemia II |
| Sarcosine | B, U | ↑ | H | Mitochondrial disorders |
| Sarcosine | B, U | ↑ | H | Sarcosinemia |
| Serine | B | ↓ | L | Cystathionine β-synthase deficiency |
| Serine | B, CSF | ↓ | L | Serine deficiency disorders |
| S-Sulfocysteine | B, U | ↑ | H | Molybdenum cofactor deficiency |
| S-Sulfocysteine | B, U | ↑ | H | Sulfite oxidase deficiency |
| Taurine | U | ↑ | H | β-Alaninemia |
| Taurine | U | ↑ | H | Molybdenum cofactor deficiency |
| Taurine | U | ↑ | H | Sulfite oxidase deficiency |
| Tryptophan | U | ↑ | H | Tryptophanuria |
| Tyrosine | B, U | ↑ | H | 4-Hydroxyphenylpyruvate dioxygenase deficiency (Tyrosinemia III) |
| Tyrosine | B, U | ↑ | H | 4-Hydroxyphenylpyruvate oxidase deficiency |
| Tyrosine | B, U | ↑ | H | Fumarylacctoaectase deficiency (Tyrosinemia I) |
| Tyrosine | B, U | ↑ | H | Neonatal transient tyrosinemia |
| Tyrosine | B | ↓ | L | PKU |
| Tyrosine | B | ↓ | L | Pterin disorders |
| Tyrosine | B, U | ↑ | H | Tyrosine aminotransferase deficiency (Tyrosinemia II) |
| Valine | B, U | ↑ | H | E3 Lipoamide dehydrogenase deficiency |
| Valine | B, U | ↑ | H | Hypervalinemia |
| Valine | B, U | ↑ | H | Maple syrup urine disease |

B, blood;
U, urine;
CSF, cerebrospinal fluid;
H, high;
L, low.

Diagnostic methods discussed above can be useful for urine samples. Urine is presently understood to be a complex matrix for analysis, dependent on kidney filtration and reabsorption efficacy, often requiring collection of 24-hour urines, often under professional supervision in metabolic wards. Aside from standardization against creatinine, many analytes require deconjugation procedures, derivatizations, extraction, or solid state isolation steps. Methods described herein can replace traditionally challenging procedures, typically used for confirmatory second-tier assays, with simple and rapid protocols suitable for routine use "next-to-subject".

In the context of newborn screening, urinalysis has been validated based on post-derivatization GC-MS with standard additions for more than 130 different inborn metabolic inflictions (see Matsumoto 1996 Mass Spectrometry Reviews 15, 43-57). Methods described herein can avoid the more laborious and complicated GC-MS analysis. Such a break through is provided by aptameric sensors, with their ability to transduce adaptive binding into a signal, described herein.

In healthy urine, sets of two specific or optimized differentially responsive aptameric sensors can have very similar ratios of responses; in urines with gross shifts, these ratios can change dramatically, regardless of renal filtration. For example, aside from the detection of allo-isoleucine, the diagnosis of MSUD is conventionally made based on the ratio of leucine and isoleucine to phenylalanine in chromatographs of derivatives. According to compositions and methods described herein, the same effect can be achieved in a single-step measurement.

Molecular Biology

Design, generation, and testing of the variant nucleotides having the above required percent identities and retaining a required aptameric activity is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide variants having, for example, at least 90-99% identity (e.g., 95%) to a reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. Deletion is the replacement of a nucleic acid by a direct bond. Positions for deletions include the termini and linkage positions. Insertions are introductions of nucleic acids into the chain, a direct bond formally being replaced by one or more nucleic acids. Nucleic acid sequence can be modulated with the help of art-known computer simulation programs.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to target molecule, derivatization agent, aptamer, or materials or reagents for identification or isolation of an aptamer. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein serves as a shorthand method of referring individually to each separate value falling within the range. Unless otherwise indicated herein, each individual value is incorporated into the specification as if it were individually recited herein. Similarly, it is understood that recitation of ranges of values herein serves as a shorthand method of referring to ranges between each of the recited values.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Selection Principles

The following example describes the selection protocol. A solution-phase protocol was used as the starting point for selection to identify aptameric sensors for steroids suitable for cross-reactive arrays [12-14]. A receptor*target complex is used to selectively interact with the aptamer (see e.g., FIG. 1B).

Figure 1B:
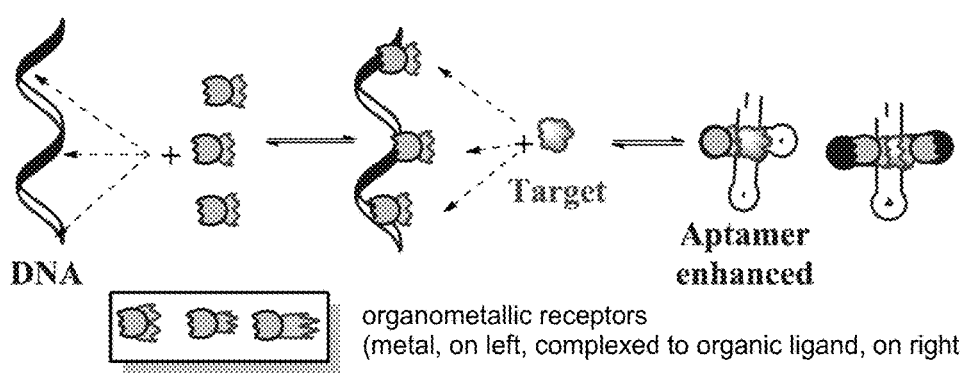
FIG. 1B is an illustration of a generic scheme of complexation between a receptor (e.g., organometallic receptor including metal and organic ligand) and its target (e.g., DNA), with further binding of enhanced aptamer.
Figure 1C:
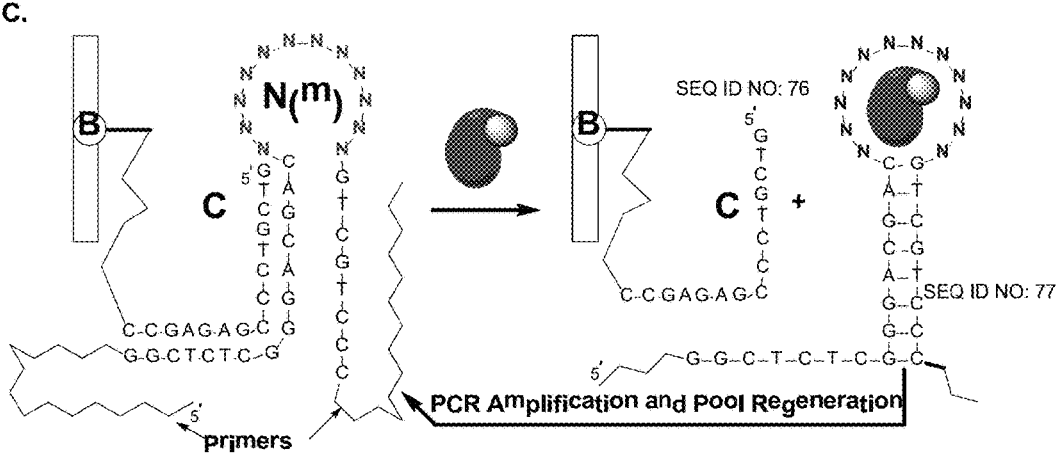
FIG. 1C is an illustration of the selection, where the targeting receptor is in the presence of a large excess of target.
Figure 1D:
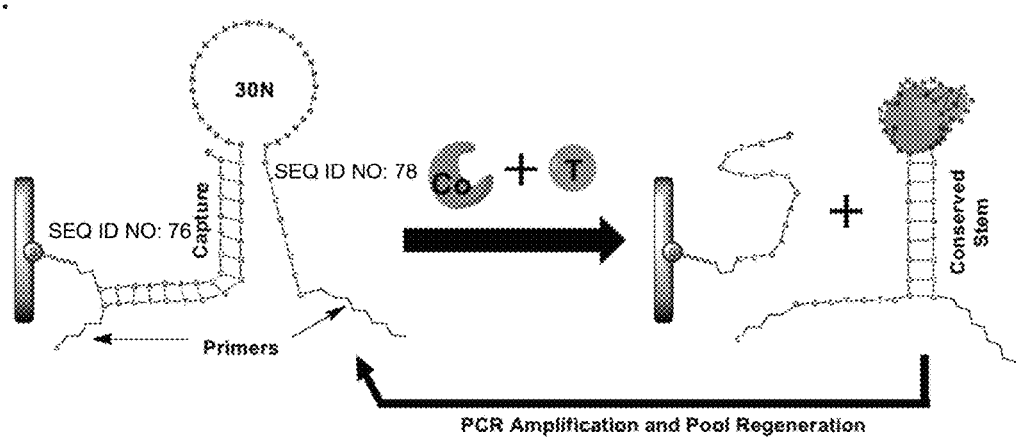
FIG. 1D is similar to FIG. 1A with 30N.
Figure 1E:
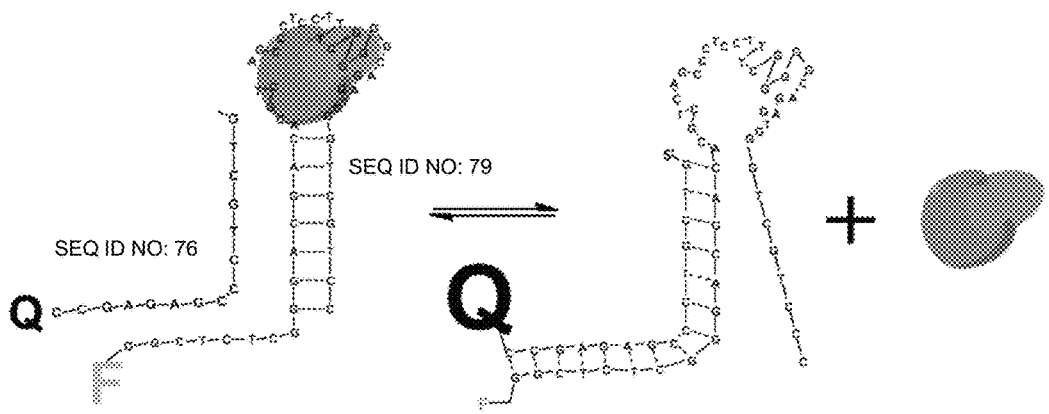
FIG. 1E shows equilibrium relationship between receptor and target.

A capture oligonucleotide, complementary to the part of the primer of a library of random oligonucleotides is displayed within the affinity matrix in a chromatography column. A capture oligonucleotide is shown in FIG. 1B, where C is attached to streptavidin column via biotin—B—at 3' end. A library of random oligonucleotides is shown in FIG. 1B, where N(m) represents a random region of m bases, with m being any number between 1 and 100. Bases shown in FIG. 1B are primer regions used for PCR.

The capture strand is used to immobilize the library members and solution-phase target(s) is applied during the affinity elution step. Aptameric structures within this library that interact with target molecule(s) in a way that promotes the formation of a stem competing with the capture oligonucleotide (i.e., displacing the capture oligonucleotide) will be preferably eluted from the column and, thus, favored during the selection process. The method is very convenient as it directly yields aptamers in an easy-to-test sensor form at the end of the selection[15,16].

Here, synthetic receptors are added to the affinity elution step in the presence of an excess of target molecule itself, to push the equilibrium towards the formation of complex between receptor and target, while also counter-selecting against target and receptor individually. This procedure results in favoring the elution of aptamers that interact (form the stem) selectively with the complex (see e.g., FIG. 1A-B).

Example 2: Aptameric Sensor with Tyrosine as Target

The following example describes the high-affinity and high-specificity, low complexity aptameric sensors, targeting tyrosine.

Figures 3A, 3B, 3C, 3D, 3E, 3F:
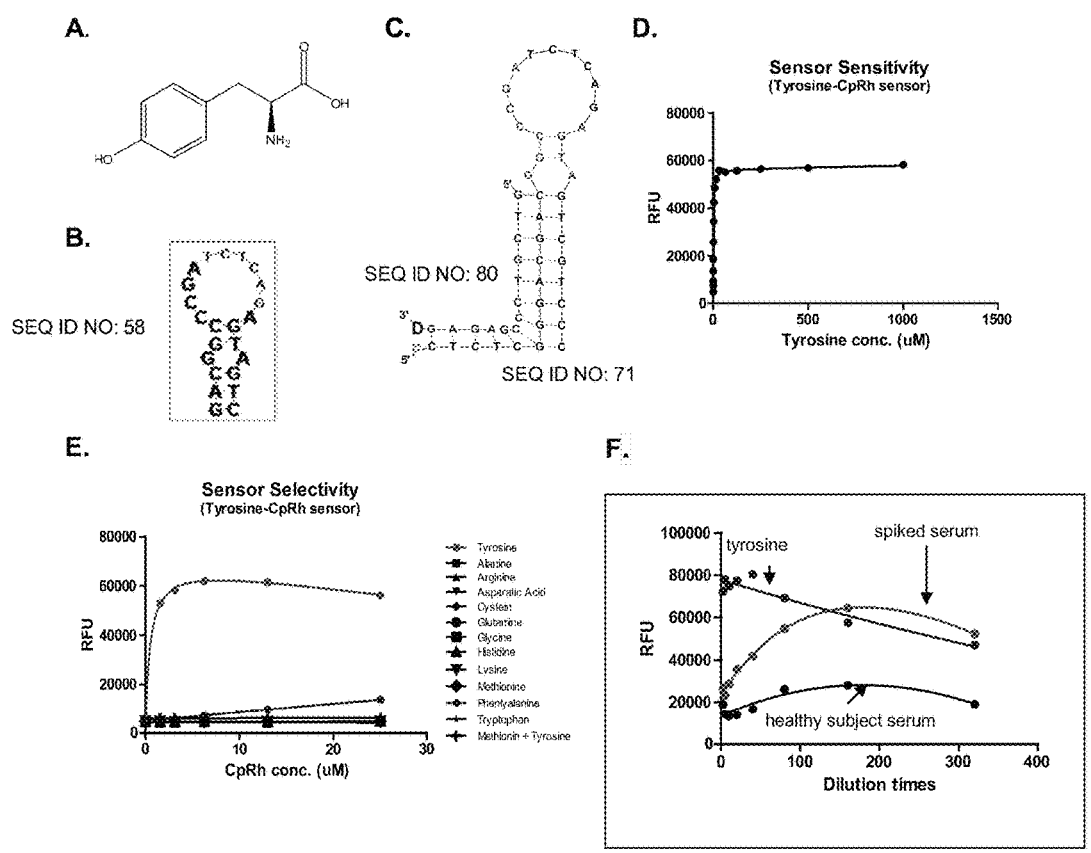
FIG. 3A-FIG. 3F is a series of chemical structures and line and scatter plots showing the detection of tyrosine in dilute-and-measure assay at clinically relevant concentrations.
Figure 4A:
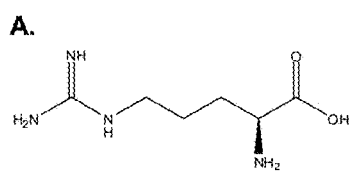
FIG. 4A-FIG. 4J is a series of chemical structures and line and scatter plots showing the detection of arginine in dilute-and-measure assay at clinically relevant concentrations.
Figure 4B:
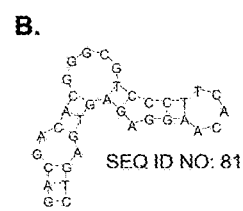
Figure 4C:
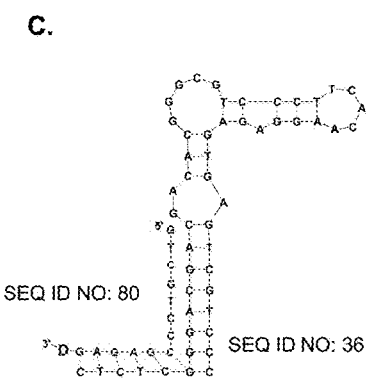
Figure 4D:
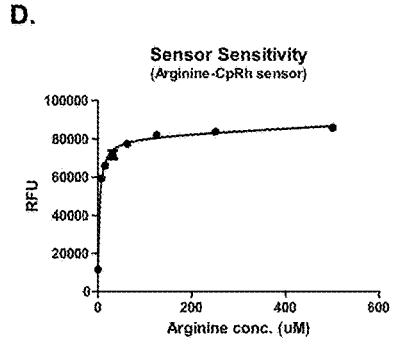
Figure 4E:
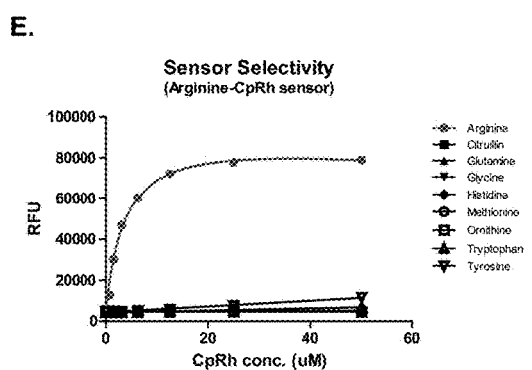
Figure 4F:
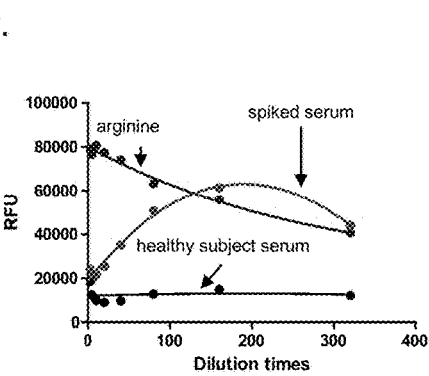
Figure 4G:
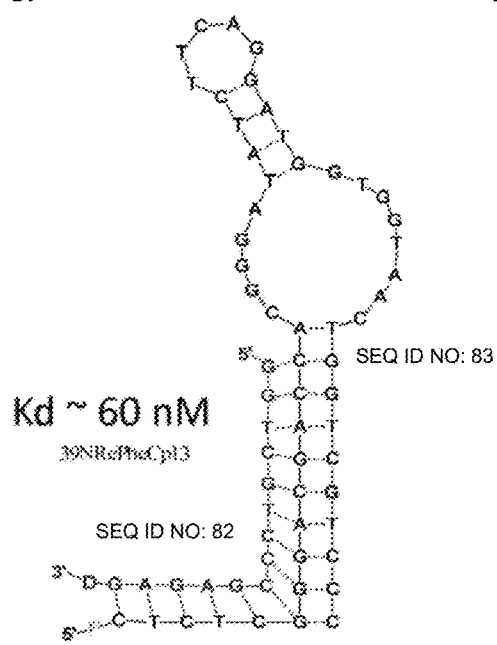
Figure 4H:
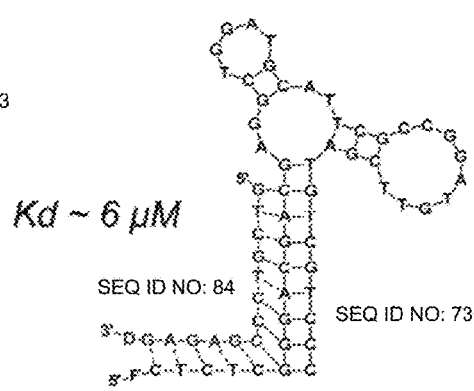
Figure 4I:
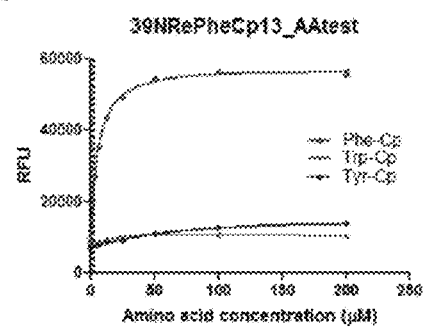
Figure 4J:
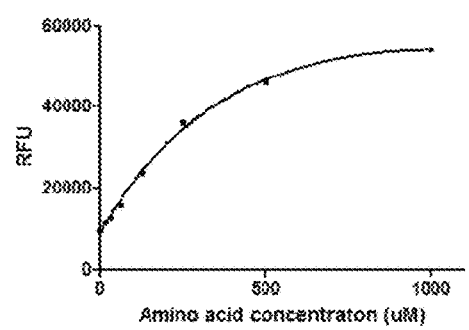

The first target was chosen based on the desire to compare results of a standard SELEX protocol without addition of any receptor, for a target that can be representative of a "typical" small organic molecule. The amino acid, tyrosine, was selected based on characteristics such as electron rich aromatic group, only one positive charge, and a mediocre ability to form highly organized hydrogen bonding networks. These characteristics can be representative of typical targets (e.g., dopamine, cocaine) that are expected to bind to aptamers in a low-to-mid micromolar range, as it is indeed the case with a reported 63-mer receptor with $K_d$~35 µM [17]. Tyrosine (see e.g., FIG. 3A) can also be an interesting target from the clinical chemistry perspective. Increase in tyrosine levels can indicate inborn metabolic errors (e.g., different types of tyrosinemia).

Figure 2:
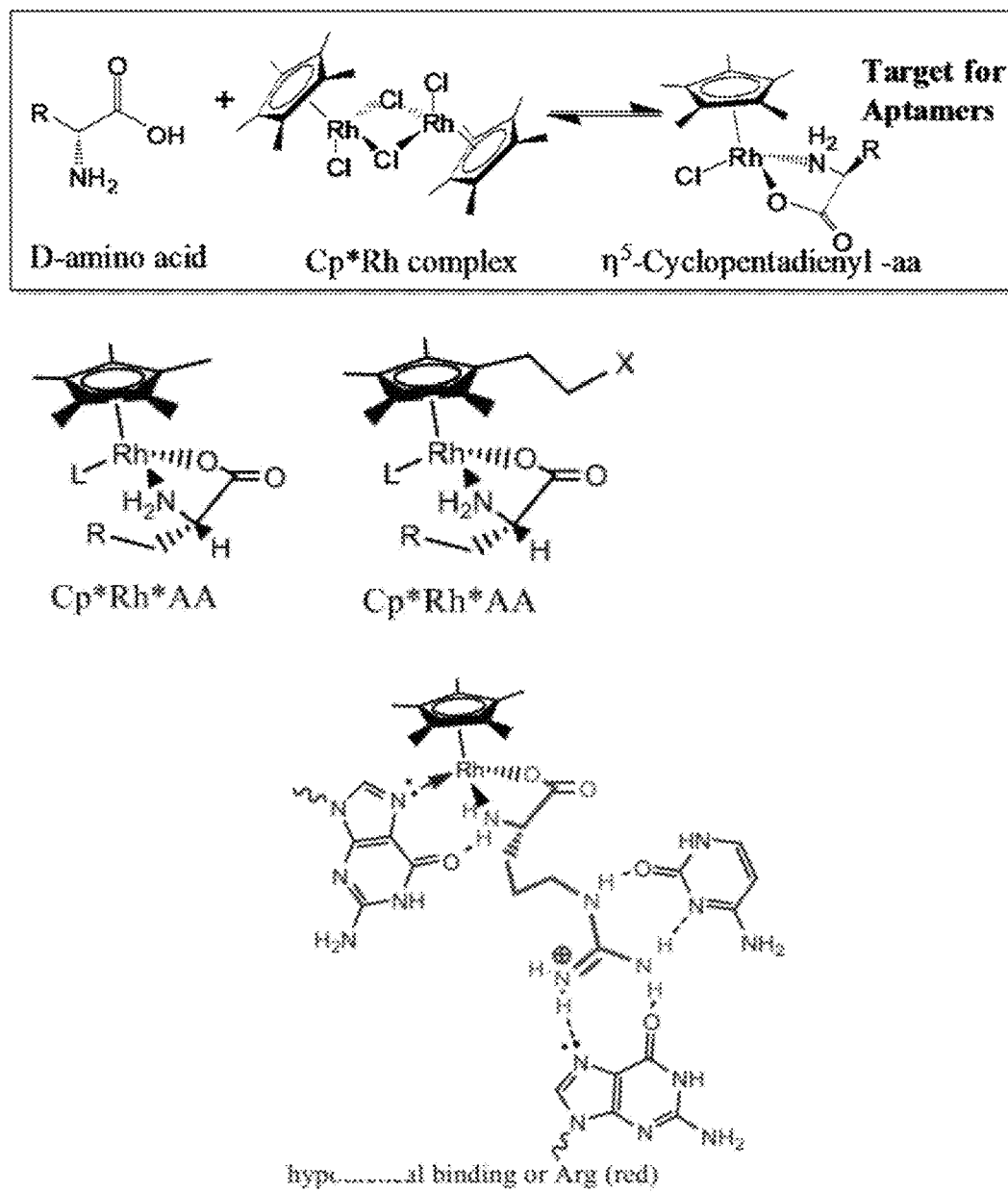
FIG. 2 is an illustration of the mechanism for a Cp*Rh (III) complex used to in situ derivatize all bi- and tri-dentate ligands, such as amino acids, amino sugars, peptides, diols. Also illustrated is Cp*Rh(III) complex binding to arginine.

Cp*Rh(III) was selected as a synthetic receptor for tyrosine (see e.g., FIG. 2, ref. [18] in the context of cross-reactive arrays for classification of amino acids, peptides, and amino sugars). This complex would add to the existing functionalities within tyrosine: a metal-ion coordination site, an additional hydrophobic surface, and would eliminate several rotational freedoms present in free tyrosine as well as the negative charge of carboxylate. A parallel selection was performed, as a control, without the addition of Cp*Rh(III). N(30) library was used to ensure full coverage of receptor space in both selections. Because the complex should not be selective for amino acids, the selectivity should originate from the aptamer.

Further, as other amino acids would compete for binding, in a typical application an excess of complex would convert all amino acids in highly diluted bodily fluids into complexes, with the aptamer picking up only one of them.

During selection, the Cp*Rh(III) was added at a concentration of 50 pM at the affinity elution step in the presence of 1 mM tyrosine. These conditions ensured that the receptor was over 90% in the complex based on an estimated association constants of amino acids with the receptor. Counter-selection was performed by adding the receptor in the absence of tyrosine to the elution buffer. These conditions reduced opportunities for favoring aptamers in selection that would bind to the receptor in the absence of target.

Intermittent counter selections with tyrosine were also introduced to maximize binding to complex itself. After eleven rounds of selection, the cloned pool was analyzed and significant convergence was observed, with Cp*Rh(III)*Tyr binding motif (see e.g., FIG. 3B). The selection directly led to an aptamer in the form that was suitable for a competitive assay with oligonucleotide (see e.g., FIG. 3C). The sensor showed near-absolute selectivity for the complex over its individual components and over tested examples of natural amino acids, but for the small response to phenylalanine (see e.g., FIG. 3E). The half-saturation point in the selection buffer for a sensor in a competitive assay was between 250-300 nM, which allowed the determination of calculated $K_d$ for the complex of 22-25 nM. This value is approximately an order of magnitude higher than the tightest binding aptamer against any amino acid (cf., arginine) [19]. In parallel, SELEX was performed in the absence of a receptor, but under otherwise identical conditions and no sensors capable of sensing tyrosine were isolated according to this conventional approach.

Because Cp*Rh(III) is a non-specific receptor, other amino acids and potential ligands could compete in mixtures. But the high affinity of a sensor can enable detection of small changes of concentration of target in complex mixtures at high dilutions (500-1000).

To demonstrate this principle, tyrosine was added to healthy sera at concentrations that would be characteristic for tyrosinemia. Upon dilution of serum 1:100-200 in detection buffer, the sensor was clearly able to distinguish spiked from non-spiked samples. Similar results were obtained with urine.

The approach as described herein specifically targets the complexes of synthetic receptors and their ligands rather than individual components of the complex, rendering the approach different from more traditional incorporation of modified bases or cofactors into aptamers. This approach can provide for detection of small concentrations of amino acids in the presence of an excess of ligand (e.g., a highly diluted sample of a biological fluid containing an amino acid).

Human serum, which contains numerous compounds forming complexes with a receptor, was obtained and serial diluted (before and after spiking it with 1 mM tyrosine). The samples mimic dilutions of healthy serum and serum characteristic of tyrosinemia. The two at dilutions of 1:80 and 1:160 were clearly distinguishable (see e.g., FIG. 3F). The data indicates that an increase in tyrosine concentration characteristic for a disease at 1:100 dilution can be detected in the presence of an excess Cp*Rh(III), without any derivatization and in the presence of numerous agents that would otherwise interfere.

The protocols described in this example can also be used for an array of aptamers to read compositions of amino acids in highly diluted urine samples. The assay, as described herein is the first of its kind in clinical chemistry that target complexes with high-specificity.

In situ derivatization, with completely non-specific organometallic receptors, such as Cp*Rh(III), can be used in selection of aptamers to shift their selectivity and sensitivity into practically useful ranges, by a combination of a solution-phase SELEX and counter selection against individual components. More specifically, based on demonstrations with tyrosine, a long standing problem has been solved: detection of a change in an amino acid concentration in serum (or other bodily fluids) with a simple dilute-and-measure assay.

Example 3: Aptameric Sensor with Arginine as Target

The following example describes high-affinity and high-specificity, low complexity aptameric sensors targeting arginine using the procedure as described in Examples 1-2. Arginine was the target molecule, Cp*Rh was used as the receptor, and the sensor was based on AKArg-1. The sensor was highly selective over other amino acids including similar citrulline (see e.g., FIG. 4).

In situ derivatization, with completely non-specific organometallic receptors, such as Cp*Rh(III), can be used in selection of aptamers to shift their selectivity and sensitivity into practically useful ranges, by a combination of a solution-phase SELEX and counter selection against individual components. More specifically, based on demonstrations with arginine, a long standing problem has been solved: detection of a change in an amino acid concentration in serum (or other bodily fluids) with a simple dilute-and-measure assay.

Example 4: Aptameric Sensor with Glucose as Target

The following example describes the high-affinity and high-specificity, low complexity aptameric sensors, targeting glucose.

Numerous attempts to isolate glucose binding aptamers resulted in multiple candidate receptors that were somewhat responsive to fluorophore derivatized receptors at higher millimolar concentrations (>50 mM), but were difficult to reproduce. The control experiments, in which fluorescein would be attached to a double helical structure, yielded similar magnitudes of responses, leading to the conclusion that the aptamers isolated, even if real, would not have been suitable analytical and nanotechnology applications.

Interactions between boronic acids and diols can be used as a basis for construction of glucose-responsive sensors. Here, a glucose-selective bis-boronic receptor (see e.g., FIG. 5A), with $K_d$ for glucose of ~500 μM, was chosen. The bis-boronic receptor can be selective for glucose over other sugars. The bis-boronic receptor can operate at physiological conditions. The transduction of a binding event of the Shinkai's receptor to glucose into a fluorescent signal, should provide an important internal control for any isolated aptamer. It is expected that fluorescence indicating the formation of a complex should match any changes in aptameric sensor response.

The Shinkai's receptor was synthesized from a bis-aldehyde. During selection, the receptor was added at concentrations of 50 μM at the affinity elution step in the presence of 40 mM glucose; these conditions ensured that the receptor was over 90% in the complex. Counter-selection was performed by adding the receptor in the absence of glucose to the elution buffer. Counter-selection for glucose was not performed separately because the response of aptamers to glucose would have been considered beneficial on its own. Through these conditions, opportunities for favoring aptamers in selection that would bind to the receptor in the absence of glucose were minimized (see FIG. 5D; FIG. 5E). As a result, after 13 cycles a series of aptamers were isolated, that, when turned into sensors (see e.g., FIG. 5B, FIG. 5C) behaved as predicted and responded to an increase in glucose concentrations.

Figure 5A:
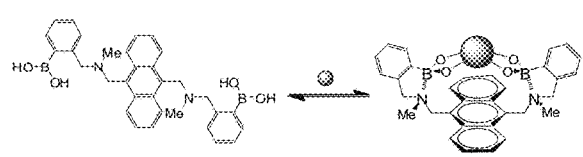
FIG. 5A is an illustration of the mechanism of the complexation of Shinkai's sensor, an example of boronic acid-based sensing of glucose (or other sugars), with glucose (presented as a sphere).
Figure 5B:
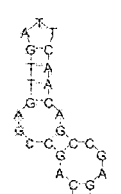
FIG. 5B is an illustration of an example of an aptamer that binds only to glucose.
Figure 5C:
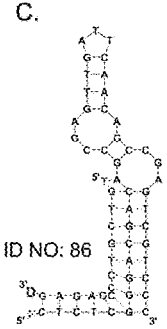
FIG. 5C is an illustration of the structure of sensor based on the aptamer in FIG. 5B (where F represents fluorescein and D represents dabcyl).
Figure 5D:
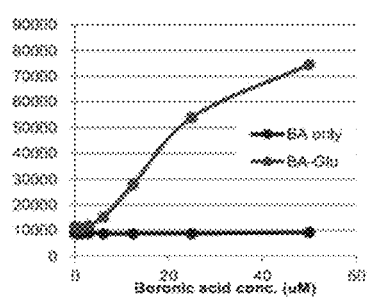
FIG. 5D is a line and scatter plot showing response of the sensor of FIG. 5C to BA only or BA-Glu.
Figure 5E:
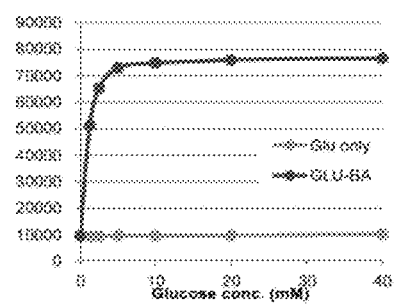
FIG. 5E is a line and scatter plot showing response of the sensor of FIG. 5C to Glu only or BA-Glu
Figure 5F:
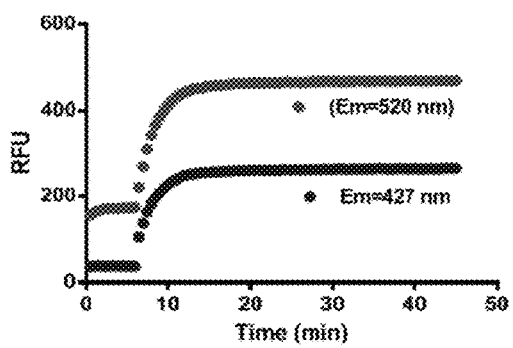
FIG. 5F is a plot showing the response of the sensor of FIG. 5C binding to glucose at 520 correlated with the response of the same sensor binding to glucose at 427 nm.
Figure 5G:
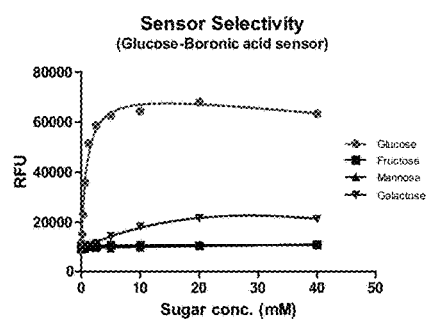
FIG. 5G is a line and scatter plot showing the response of the sensor from FIG. 5C to glucose and other sugars, in the presence of 50 µM Shinkai's sensor.
Figure 5H:
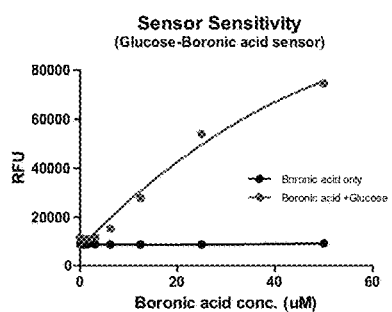
FIG. 5H is a line and scatter plot showing the response to boronic acid sensor (Shinkai's) in the presence and absence of 40 mM glucose.
Figure 5I:
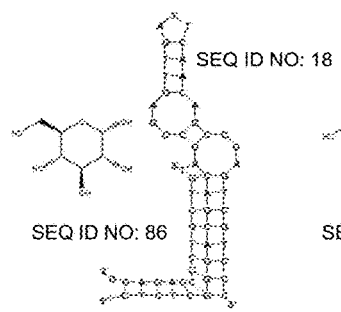
FIG. 5I illustrates an aptamer sensor, which is shown specific for glucose in FIG. 5L.
Figure 5J:
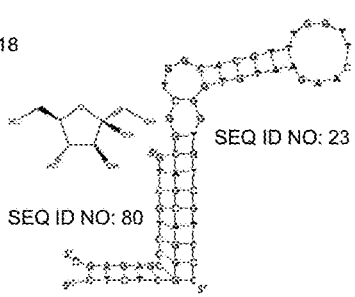
FIG. 5J illustrates an aptamer sensor, which is shown specific for fructose in FIG. 5M.
Figure 5K:
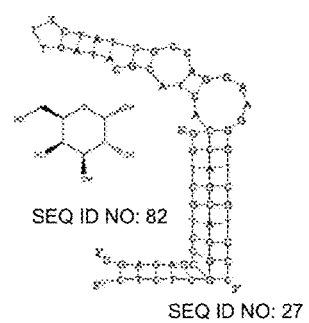
FIG. 5K illustrates an aptamer sensor, which is shown specific for galactose in FIG. 5N.
Figure 5L:
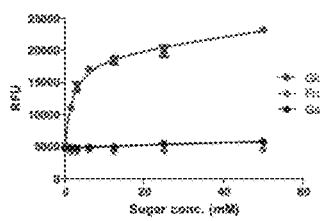
Figure 5M:
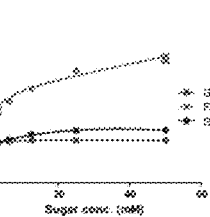
Figure 5N:
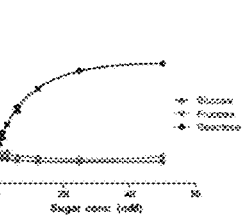
Figures 6A, 6B:
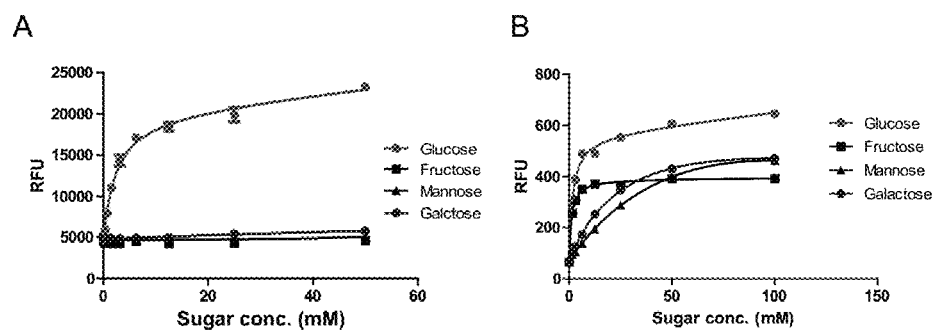
FIG. 6A-FIG. 6B are line and scatter plot comparisons of selectivity and sensitivity of a (Shinka's) boronic acid sensor with and without aptamer.

A predominant aptameric glucose sensor in shown in FIG. 5B, based on YKG-1. The response of this sensor at 520 nm to the addition of glucose in the presence of receptor correlated with the response of receptor binding to glucose at 427 nm (see FIG. 5F). The selectivity for glucose was improved. The symmetrical structure of the receptor, the unusual shape of a binding isotherm, and binding of more than one equivalent of complex at saturating conditions in titration experiments of YKG-1 support the binding of two boronic acid-glucose complexes to one aptamer.

Sensors specific for glucose (see e.g., FIG. 5I, FIG. 5L), fructose (see e.g., FIG. 5J, FIG. 5M), and galactose (see e.g., FIG. 5K, FIG. 5N) were also identified.

In situ derivatization with a receptor designed to have some degree of specificity, such as Shinkai's sensor, can be used in the selection of aptamers to shift their selectivity and sensitivity into practically useful ranges, by a combination of a solution-phase SELEX and counter selection against individual components.

Example 5: Aptameric Sensors with Unpaired Bases

The following example shows a series of aptamers having a nucleic acid sequence with one or more unpaired bases such that a metal complex can bind a pocket formed by the one or more unpaired bases and also binds the target amino acid. An exemplary binding site is formed by the G-A mismatch surrounded by binding base pairs (e.g., G-C, G-T, A-T, A-U or analogs) as shown below (see FIG. 7A):

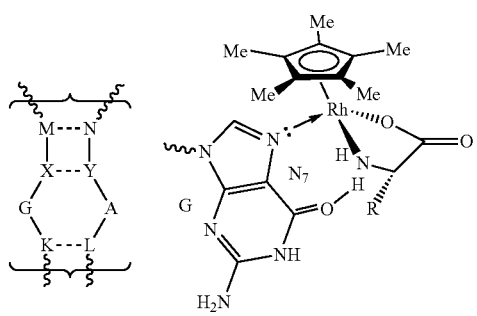

A series of aptamers were formed having an unbound nucleic acid pocket (see e.g., FIG. 7B-G). FIG. 7B-G shows a Cp*Rh(III)-amino acid binding aptamer in sensor form along with the amino acid for which initial selection was performed (e.g., Tyr for FIG. 7B. Phe for FIG. 7C, Citrulline in FIG. 7D, Gln in FIG. 7E). In some aptamers, a motif was recognized straight from folding programs, such as in FIG. 7B-E. In some aptamers, a motif can be recognized from primary sequence (i.e., motif does not necessarily show in folding program, as in two Lys sensors), such as in FIG. 7F-G. In some aptamers, an unbound nucleic acid pocket binds Cp*Rh (compare FIG. 7B-G), but can also bind other metals (compare Cu2+ in FIG. 7H).

The following examples show a series of aptamers having at least two unpaired bases forming a pocket that binds a metal complex or an amino acid target molecule.

An exemplary motif having a plurality of unpaired bases forming a pocket that binds a metal complex or an amino acid target molecule is shown in FIG. 8A. Exemplary aptamers include an Arg selective aptamer (see e.g., FIG. 8B); a Trp selective aptamer (see e.g., FIG. 8C); a Gly selective aptamer (see e.g., FIG. 9A); an Asn selective aptamer (see e.g., FIG. 9C); and a Gly non-specific aptamer (see e.g., FIG. 9C).

The following examples shows an aptamer having multiple folding configurations (compare FIG. 10A and FIG. 10B), which is selective for Leu over Ile and has a plurality of unpaired bases forming a plurality of pockets, one of more of which pockets can bind a metal complex and also an amino acid target molecule. A Cp*Rh(III) can bind more than one site, such as additional G's that can be targeted.

Example 6: Use of Aptameric Sensors with Unpaired Bases

The following example shows an aptamer with unpaired bases that is reactive for Phe and cross-reactive for Trp, along with use thereof.

Figure 11B:
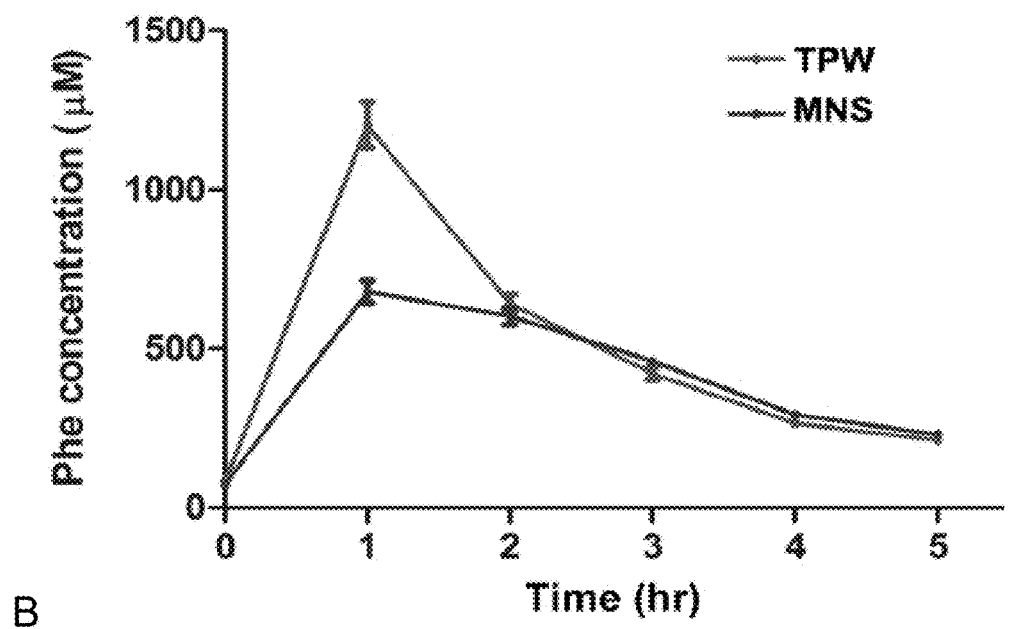

An aptamer a plurality of unpaired bases and reactive for Phe and cross-reactive for Trp is shown in FIG. 11A. This aptamer was used to detected Phe concentration (μM) as a function of time (hr) in serum samples from capillary blood of a female subject (TWP) and a male subject (MNS) that took 100 mg of phenylanine per kg body weight by mouth at time zero (see e.g., FIG. 11B). The phenylalanine concentration in blood rises significantly at this dosage (see 1 hr in FIG. 11B). Every hour, blood was measured for the phenylalanine concentration. In a healthy subject, the enzymes that break down phenylalanine (e.g., phenylalanine hydroxylase (PAH) or BH4-cofactor, alone or together) are stimulated and break down phenylalanine resulting in decreased concentration (see 2-5 hr in FIG. 11B). In subjects with PKU this does not happen, as PKU is caused by mutations in the degrading enzymes.

An aptamer a plurality of unpaired bases and reactive for Phe is shown in FIG. 12A. This aptamer sensor mixture (not including Cp*Rh) was incubated with concentrations of amino acids (Phe, Tyr, Trp, Gly) and fluorescence (RFU) measured (see e.g., FIG. 12B).

Figure 12D:
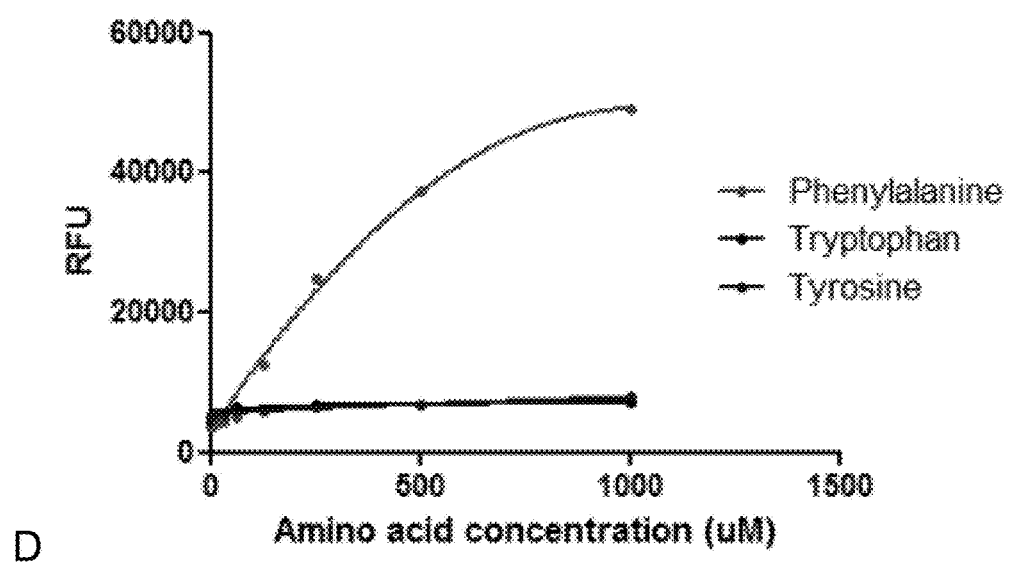

An aptamer a plurality of unpaired bases and reactive for Phe is shown in FIG. 12C. This aptamer sensor mixture (not including Cp*Rh) was incubated with concentrations of amino acids (Phe, Trp, Tyr) and fluorescence (RFU) measured (see e.g., FIG. 12D).

---

SEQUENCE LISTING

SEQ ID NO: 1
5' primer end of library oligonucleotides
CTCTCGGGACGAC

SEQ ID NO: 2
3' primer end of library oligonucleotides
GTCGTCCC

SEQ ID NO: 3
Aptamer against glucose-boronic acid complex
Short binding form
GACAGCCGAGTGCATTCAACAGCCGAGTC SEQ ID NO: 4
Glucose-BA_01
CTCGGGACGACAGCCGAGTTCAGGGATTCCCTAACAGCCGAGTCGTCCC SEQ ID NO: 5
Glucose-BA_07
CTCGGGACGACAGCCGAGTTATGACATTCAATAACAGCCGAGTCGTCCC

SEQUENCE LISTING

SEQ ID NO: 6
Glucose-BA_08
CTCGGGACGACCAGCCGAGATTTTGCATAAAAACAGCCGAGGTCGTCCC

SEQ ID NO: 7
Glucose-BA_09
CTCGGGACGACCAGCCGAGATAGGTCGTTCTATCAGCCGAGGTCGTCCC

SEQ ID NO: 8
Glucose-BA_10
CTCGGGACGACAACCGAGTAGGATACTAAGCATCCAGCGGAGTCGTCCC

SEQ ID NO: 9
Glucose-BA_11
CTCGGGACGACAGCCGAGGAAACAAACTTTTTTCCAGCCGAGTCGTCCC

SEQ ID NO: 10
Glucose-BA_12
CTCGGGACGACCGCGGGAGCAATGCGATGACGAAGGACGGGGTCGTCCC

SEQ ID NO: 11
Glucose-BA_13
CTCGGGACGACCGGAGCTCCTGCGATTGACTAAAAGGAAGGTCGTCCC

SEQ ID NO: 12
Glucose-BA_14
CTCGGGACGACAGCCGAGTCAAAGTTTAACTTGACAGCCGAGTCGTCCC

SEQ ID NO: 13
Glucose-BA_15
CTCGGGACGACGGGGAACGTTTTCGTGGATGAGCTGGCGACGTCGTCCC

SEQ ID NO: 14
Glucose-BA_16
CTCGGGACGACGGGGGAGAGTATTGGATGACCGCAGGGACCGTCGTCCC

SEQ ID NO: 15
Glucose-BA_17
CTCGGGACGACGGGGGGAACATTGTGATCTCGTTAGAGCACGTCGTCCC

SEQ ID NO: 16
GLUBA02
CTCTCGGGACGACGGACCGTTAGGGGAGCCAGTGCGCGATGACGTCGTCCC

SEQ ID NO: 17
GLUBA09
CTCTCGGGACGACAGCCGAGTTCAGGGAcTTCCCTAACAGCCGAGTCGTCCC

SEQ ID NO: 18
GLUBA09_M1
CTCTCGGGACGACAGCCGAGTTGATTCAACAGCCGAGTCGTCCC

SEQ ID NO: 19
GLUBA17
CTCTCGGGACGACAGCCGAGCACTACATTAGTTGGGCAGCCGAGTCGTCCC

SEQ ID NO: 20
GLUBAN3W10
CTCTCGGGACGACGACCGTAGGGGTAGCTGTATATGCGGATGAGTCGTCCC

SEQ ID NO: 21
GLUBAN3W11
CTCTCGGGACGACAGGGGGTAGGGGGCCCGGACTGTTAAGGGTGTCGTCCC

SEQ ID NO: 22
GLUBAN3W19
CTCTCGGGACGACGGGACCAACCGGGATGAGCATAAGTGCGACGTCGTCCC

SEQ ID NO: 23
FrucBA02
CTCTCGGGACGACGGCTGGCACGTTTGGTTCAAGAATGTGGGTGTCGTCCC

SEQ ID NO: 24
FrucBA02_M1
CTCTCGGGACGACGGCTGGCACGTTGAATGTGGGTGTCGTCCC

SEQ ID NO: 25
FrucBA05
CTCTCGGGACGACGGACAGAGGTTCGAGCGTGCGCTCTAGGAAGTCGTCCC

SEQ ID NO: 26
GalacBA01
CTCTCGGGACGACCCAGGTGTCCTGCTTCTCAGTAGTAGGTTAGTCGTCCC

SEQ ID NO: 27
GalacBA04
CTCTCGGGACGACCACTACGCATAGTTTCTATCGCCAGGAAGGGTCGTCCC

SEQ ID NO: 28
GalacBA06
CTCTCGGGACGACCGAGTAGGTGTCCTGGATGCAGGTTTGGAGGTCGTCCC

SEQ ID NO: 29
BAOnly01
CTCTCGGGACGACCAGGTGGGGCTGCTCAAGTGGAGGTTCCTCGTCGTCCC

SEQ ID NO: 30
BAOnly03
CTCTCGGGACGACCAGAGGGGCCTCAAATGTGGGGTGTTGCTCGTCGTCCC

SEQ ID NO: 31
Aptamer against Arginine-Cp*Rh complex
Short binding form
GACGACACGGGCGTCCCTTATCACAAGGAGAGTGAGTC SEQ ID NO: 32
Arginine-Cp*Rh_02
CTCTCGGGACGACGGGTGTCCCTGTGGACCTGTACATAGGAGAGTCGTCCC SEQ ID NO: 33
Arginine-Cp*Rh_03
CTCTCGGGACGACGCGGGTGTCCCTTGGTAAACCAAGGAGAGTGTCGTCCC SEQ ID NO: 34
Arginine-Cp*Rh_04
CTCTCGGGACGACGGCTAGGAGAGGTGTCCGGGTGTCCCAGGTGTCGTCCC SEQ ID NO: 35
Arginine-Cp*Rh_05
CTCTCGGGACGACCCACGAGAGACTCCAAACGATTGCCGTCCC SEQ ID NO: 36
ARG01_Cp
CTCTCGGGACGACGACACGGGCGTCCCTTCACAAGGAGAGTGAGTCGTCCC SEQ ID NO: 37
AspaCp01
CTCTCGGGACGACGGCACTTGTTGCGTGAAGCGTATGCGAATAGTCGTCCC SEQ ID NO: 38
AspaCp03
CTCTCGGGACGACGGGCCACGTTTTCCAGGTACTTTCTAAGGGGTCGTCCC

SEQUENCE LISTING

SEQ ID NO: 39
AspaCp04
CTCTCGGGACGACGGGCCTTCGGTGGCTGAGCATAGCGATGGGGTCGTCCC

SEQ ID NO: 40
CIT30N02_Cp*Rh
CTCTCGGGACGACGGCGGGGAAACAGCTGCAAAATGTGGAGTAGTCGTCCC

SEQ ID NO: 41
GlutaCp02
CTCTCGGGACGACGGCGGGTGAATGCACACTTAGCAGAGAGTAGTCGTCCC

SEQ ID NO: 42
GlutaCp15
CTCTCGGGACGACGGCGGGGAAAGGACCCTAGTTCCTGGTGTAGTCGTCCC

SEQ ID NO: 43
Aptamer against Glycine-Cp*Rh complex
Short binding form
GACGGGCTAGGCGTGGGTGTAAAGGCACAGGGGTC SEQ ID NO: 44
Glycine-Cp*Rh_01
TCGGGACGACGGGCTAGGCGTGGGTGTAAAGGCACAGGGGTCGTCCCGA SEQ ID NO: 45
Gly-Cp sensor
CTCTCGGGACGACGGGCTAGGCGTGGGTGTAAAGGCACAGGGGTCGTCCC SEQ ID NO: 46
Gly-Cp sensor +1 bp
CTCTCGGGACGACGGGCTAGGCGTGGGTGTAAAGGCACAGGGGTCGTCCCG SEQ ID NO: 47
GLYHW-Cp*Rh_06
CTCTCGGGACGACGGGTCAGTTAGACCGTGAGGCTTCCGAATAGTCGTCCC SEQ ID NO: 48
LeuCp01
CTCTCGGGACGACGGCGGGGGTCCCAGCGTTGCATGGTGTGTAGTCGTCCC SEQ ID NO: 49
LeuCp04
CTCTCGGGACGACGGCGGGCGCGTGATCGGAGAGAAAGGTGTAGTCGTCCC SEQ ID NO: 50
LeuCp17
CTCTCGGGACGACGGCGGGCGCGTATGTATATCATAAGGTGTAGTCGTCCC SEQ ID NO: 51
LysCp05
CTCTCGGGACGACGCGGTGTGGATCCCTCGTAGAAGGAGTAGTGTCGTCCC SEQ ID NO: 52
LysCp*Rh18
CTCTCGGGACGACGGGTGGGAGCGATTCGAGCTACTCAGGTATGTCGTCCC SEQ ID NO: 53
PACp*Rh01
CTCTCGGGACGACGGACGCTAATCTTACAAGGGCGTAGTGTATGTCGTCCC SEQ ID NO: 54
PACp*Rh02
CTCTCGGGACGACCGCCGATAATCTCACAAGGGCGTATCAAAGGTCGTCCC SEQ ID NO: 55
PACp*Rh03
CTCTCGGGACGACGGGTAGGGATGTCTAATCCCGGCGGGAGCTGTCGTCCC SEQ ID NO: 56
HPheA104
CTCTCGGGACGACCGCGTTTCCCAAGAAAGCAAGTTTTGGTTGGTCGTCCC SEQ ID NO: 57
HTrp03
CTCTCGGGACGACCGCGGTAGTCTTAACCTAAAGCGGTGTCAGGTCGTCCC SEQ ID NO: 58
Aptamer against Tyrosine-Cp*Rh complex
Short binding form
GACGGCCCGATCTCAGAGTAGTC SEQ ID NO: 59
Tyrosine-Cp*Rh_02
TCTCGGGACGACggcccgaatgtgtaagtaGTCGTCCC SEQ ID NO: 60
Tyrosine-Cp*Rh_03
TCTCGGGACGACggcccgatgttccagagtaGTCGTCCC SEQ ID NO: 61
Tyrosine-Cp*Rh_04
TCTCGGGACGACggcccgatgatgtattcgagtaGTCGTCCC SEQ ID NO: 62
Tyrosine-Cp*Rh_05
CTCGGGACGACggcccgtagatattagtaGTCGTCCC SEQ ID NO: 63
Tyrosine-Cp*Rh_06
TCTCGGGACGACggcccgcattaattagtaGTCGTCCC SEQ ID NO: 64
Tyrosine-Cp*Rh_07
TCTCGGGACGACggcccgaaactgagtaGTCGTCCC SEQ ID NO: 65
Tyrosine-Cp*Rh_08
TCTCGGGACGACggcccgagcactaggagtaGTCGTCCC SEQ ID NO: 66
Tyrosine-Cp*Rh_09
TCTCGGGACGACggcccgatagtagagtaGTCGTCCC SEQ ID NO: 67
Tyrosine-Cp*Rh_10
CTCTCGGGACGACggcccgagataatcaagtaGTCGTCCC SEQ ID NO: 68
Tyrosine-Cp*Rh_11
CTCTCGGGACGACggcccgaacatatgtaagtaGTCGTCCC SEQ ID NO: 69
Tyrosine-Cp*Rh_12
CTCTCGGGACGACggcccgatatgtaattagtaGTCGTCCC SEQ ID NO: 70
Tyrosine-Cp*Rh_13
CTCTCGGGACGACggcccgacatcatcatcagtatatagagtaGTCGTCCC SEQ ID NO: 71
Tyr-Cp*Rh (38 nt)
CTCTCGGGACGACGGCCCGATCTCAGAGTAGTCGTCCC SEQ ID NO: 72
HTyrs07
CTCTCGGGACGACCAAGCGAGTAGTAACACGGCCCGACACTGGGTCGTCC
C SEQ ID NO: 73
Cu(II)_Phe01
CTCTCGGGACGACGAGGCTGGATGCATTCGCCGGATGTTCGATGTCGTCC
C SEQ ID NO: 74
Cu(II)-Phe10
CTCTCGGGACGACAAGGTCCCTTTCGTAGATCGAGGAAGTATTGTCGTCC
C SEQ ID NO: 75
Cu(II)-Phe10_49nt
CTCTCGGGACGACAGGTCCCTTTCGTAGATCGAGGAAGTATGTCGTCCC

What is claimed is:

1. A method for isolating an aptamer specific for a complex comprising a target molecule, the method comprising:
   providing a target molecule;
   providing a derivatization agent;
   contacting the target molecule and the derivatization agent to form a target complex;
   providing an oligonucleotide library comprising a plurality of aptamer candidates;
   contacting the target complex and the oligonucleotide library; and
   isolating an aptamer that binds to the target complex.

2. The method of claim 1, wherein isolating the aptamer that binds to the target complex comprises removal of aptamer candidates that do not bind to the target complex.

3. The method of claim 2, further comprising:
   eluting the aptamer from the bound target complex under increasing stringency; and
   isolating an eluted aptamer having high affinity for the target complex.

4. The method of claim 1, comprising systematic evolution of ligands by exponential enrichment (SELEX).

5. The method of claim 1, wherein the aptamer does not substantially bind the non-complexed target molecule.

6. The method of claim 1, wherein the aptamer does not substantially bind the non-complexed derivatization agent.

7. The method of claim 1, further comprising counter-selecting an aptamer against the derivatization agent alone or against the target molecule alone.

8. The method of claim 1, wherein the oligonucleotide library comprises randomly generated oligonucleotide sequences of a fixed length flanked by a constant 5' end and a constant 3' end, the constant 5' end and the constant 3' end functioning as a primer.

9. The method of claim 1, wherein the aptamer is a DNA, RNA, or XNA molecule.

10. The method of claim 1, wherein the aptamer comprises at least about 15 oligonucleotides up to about 100 oligonucleotides.

11. The method of claim 1, wherein the aptamer comprises equilibrium constant ($K_d$) of about 1 pM up to about 10.0 μM; about 1 pM up to about 1.0 μM; about 1 pM up to about 100 nM; about 100 pM up to about 10.0 μM; about 100 pM up to about 1.0 μM; about 100 pM up to about 100 nM; or about 1.0 nM up to about 10.0 μM; about 1.0 nM up to about 1.0 μM; about 1 nM up to about 200 nM; about 1.0 nM up to about 100 nM; about 500 nM up to about 10.0 μM; or about 500 nM up to about 1.0 μM.

12. The method of claim 1, wherein the target molecule comprises a small molecule, a protein, or a nucleic acid.

13. The method of claim 1, wherein the target molecule comprises a small molecule selected from the group consisting of a carbohydrate molecule, a fatty acid molecule, a steroid molecule, an amino acid, a lead-like small molecule, a drug-like small molecule, and a derivative or a combination thereof.

14. The method of claim 1, wherein the target molecule comprises a carbohydrate molecule selected from the group consisting of glucose, dextrose, fructose, galactose, sucrose, maltose, lactose, polyol, polyhydric alcohol, polyalcohol, glycitol, methanol, glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol.

15. The method of claim 1, wherein the target molecule comprises a lipid molecule selected from the group consisting of a fatty acid, a steroid, a sphingolipid, or a phospholipid.

16. The method of claim 1, wherein the target molecule comprises a steroid molecule selected from the group consisting of a caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, and docosahexaenoic acid, cholestane, a cholane, a pregnane, an androstane, a gonane, an estrane, cholesterol, estradiol, testosterone, progesterone, medrogestone, β-sitosterol, dexamethasone, sphingosine-phosphate, sphingomyelin, ganglioside, and phosphatidyl-choline, or derivatives thereof.

17. The method of claim 1, wherein the target molecule comprises an amino acid selected from the group consisting of histidine, isoleucine, leucine, lysine, methionine, phenylalanine, threonine, tryptophan, valine, alanine, arginine, asparagine, aspartic acid, cysteine, glutamic acid, glutamine, glycine, proline, serine, tyrosine, selenocysteine, pyrrolysine, lanthionine, 2-aminoisobutyric acid, dehydroalanine, N-formylmethionine, gamma-amino-butyric acid (GABA), hydroxyproline, carnitine, ornithine, S-adenosylmethionine, citrulline, beta alanine (3-aminopropanoic acid), canavanine, mimosine, aspartame, 5-hydroxytryptophan, L-dihydroxyphenylalanine, and eflornithine.

18. The method of claim 1, wherein the derivatization agent comprises a metal ion complex, a cyclic oligosaccharide, or a boronic acid.

19. The method of claim 1, wherein:
   the target molecule comprises an amino acid and the derivatization agent comprises a metal ion complex;
   the target molecule comprises a fatty acid, a steroid, a hydrophobic lead-like compound, or a hydrophobic drug-like compound and the derivatization agent comprises a cyclic oligosaccharide; or
   the target molecule comprises a carbohydrate and the derivatization agent comprises a boronic acid.

20. The method of claim 1, wherein the derivatization agent comprises Cp*Rh(III) or a metal ion complex selected from Ni(II), Cu(II), Zn(II), or Co(III) bound to a bidentate, tridentate, or tetradentate ligand.

21. The method of claim 1, wherein the derivatization agent comprises a cyclic oligosaccharide, the cyclic oligosaccharide comprising a cyclodextrin derivative.

22. The method of claim 1, wherein the derivatization agent comprises a boronic acid, the boronic acid comprising a bis-boronic acid, an aromatic boronic acid, an amino boronic acid, or an aromatic amino boronic acid.

23. The method of claim 1, wherein isolating an aptamer that binds to the target complex comprises:
   isolating an aptamer that binds to the target complex and has a nucleic acid sequence comprising one or more unpaired nucleic acid bases when the aptamer is folded into a double stranded configuration, wherein the one or more unpaired nucleic acid bases form a binding pocket such that the aptamer can bind the derivatization agent and the target molecule.

* * * * *